US 9,586,949 B2

United States Patent
Zou et al.

(10) Patent No.: US 9,586,949 B2
(45) Date of Patent: Mar. 7, 2017

(54) AZA-HETEROARYL COMPOUNDS AS PI3K-GAMMA INHIBITORS

(71) Applicant: Incyte Corporation, Wilmington, DE (US)

(72) Inventors: Ge Zou, Wilmington, DE (US); Andrew P. Combs, Kennett Square, PA (US); Andrew W. Buesking, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 15/019,144

(22) Filed: Feb. 9, 2016

(65) Prior Publication Data
US 2016/0229843 A1    Aug. 11, 2016

Related U.S. Application Data

(60) Provisional application No. 62/113,995, filed on Feb. 9, 2015.

(51) Int. Cl.
| *C07D 413/04* | (2006.01) |
| *C07D 401/14* | (2006.01) |
| *C07D 413/14* | (2006.01) |
| *C07D 417/14* | (2006.01) |
| *C07D 471/04* | (2006.01) |

(52) U.S. Cl.
CPC ......... *C07D 413/04* (2013.01); *C07D 401/14* (2013.01); *C07D 413/14* (2013.01); *C07D 417/14* (2013.01); *C07D 471/04* (2013.01)

(58) Field of Classification Search
None
See application file for complete search history.

(56) References Cited

U.S. PATENT DOCUMENTS

| 4,269,846 | A | 5/1981 | Huang et al. |
| 5,521,184 | A | 5/1996 | Zimmermann |
| 8,680,108 | B2 | 3/2014 | Li et al. |
| 8,759,359 | B2 | 6/2014 | Combs et al. |
| 8,940,752 | B2 | 1/2015 | Li et al. |
| 9,062,055 | B2 | 6/2015 | Li et al. |
| 9,096,600 | B2 | 8/2015 | Li et al. |
| 9,108,984 | B2 | 8/2015 | Combs et al. |
| 9,126,948 | B2 | 9/2015 | Combs et al. |
| 9,193,721 | B2 | 11/2015 | Combs et al. |
| 9,199,982 | B2 | 12/2015 | Li et al. |
| 2013/0261101 | A1 | 10/2013 | Combs et al. |
| 2014/0249132 | A1 | 9/2014 | Li et al. |
| 2014/0275127 | A1 | 9/2014 | Combs et al. |
| 2015/0284390 | A1 | 10/2015 | Li et al. |
| 2015/0361094 | A1 | 12/2015 | Li et al. |
| 2016/0000795 | A1 | 1/2016 | Scherle et al. |
| 2016/0022685 | A1 | 1/2016 | Li et al. |
| 2016/0024117 | A1 | 1/2016 | Li et al. |

FOREIGN PATENT DOCUMENTS

| WO | WO 00/09495 | 2/2000 |
| WO | WO 00/53595 | 9/2000 |
| WO | WO 01/14402 | 3/2001 |
| WO | WO 01/64655 | 9/2001 |
| WO | WO 01/85724 | 11/2001 |
| WO | WO 03/024967 | 3/2003 |
| WO | WO 03/035065 | 5/2003 |
| WO | WO 03/035644 | 5/2003 |
| WO | WO 03/037347 | 5/2003 |
| WO | WO 03/068225 | 8/2003 |
| WO | WO 03/099771 | 12/2003 |
| WO | WO 2004/005281 | 1/2004 |
| WO | WO 2004/046120 | 6/2004 |
| WO | WO 2004/056786 | 7/2004 |
| WO | WO 2004/078943 | 9/2004 |
| WO | WO 2004/080980 | 9/2004 |
| WO | WO 2005/012288 | 2/2005 |
| WO | WO 2005/028444 | 3/2005 |
| WO | WO 2005/118580 | 12/2005 |

(Continued)

OTHER PUBLICATIONS

Ruckle et al. Nature, 2006, 5, 903-918.*
Villard et al. Journal of Organic Chemistry, 2012, 77, 1507-1519.*
U.S. Appl. No. 60/578,491, filed Jun. 10, 2004, Ren.
Bala et al., "Highy efficient water-mediated approach to access benzazoles: metal catalyst and base-free synthesis of 2-substituted benzimidazoles, benzoxazoles, and benzothiazoles," Molecular Diversity, Mar. 2015, 19(2): 263-272.
Barber et al., "PI3Kgamma inhibition blocks glomerulonephritis and extends lifespan in a mouse model of systemic lupus," Nat Med., Sep. 2005, 11(9): 933-5.
Berge, Journal of Pharmaceutical Science, 66, 2 (1977).
Berod et al., "PI3Kγ deficiency delays the onset of experimental autoimmune encephalomyelitis and ameliorates its clinical outcome," Eur J Immunol, Mar. 2011, 41(3): 833-44.
Blom et al., "Optimizing Preparative LC/MS Configurations and Methods for Parallel Synthesis Purification," J. Comb. Chem., 2003, 5: 670-683.

(Continued)

*Primary Examiner* — Yevegeny Valenrod
(74) *Attorney, Agent, or Firm* — Fish & Richardson P.C.

(57) ABSTRACT

The present invention provides aza-heteroaryl derivatives of Formula I:

and pharmaceutically acceptable salts thereof, wherein X, Y, Z, A, W, $R^4$, $R^5$, and $R^6$ are defined herein, that inhibit the activity of phosphoinositide 3-kinases-gamma (PI3Kγ) and are useful in the treatment of diseases related to the activity of PI3Kγ including, for example, autoimmune diseases, cancer, cardiovascular diseases, and neurodegenerative diseases.

26 Claims, No Drawings

(56) References Cited

FOREIGN PATENT DOCUMENTS

| WO | WO 2007/019416 | 2/2007 |
|---|---|---|
| WO | WO 2007/019417 | 2/2007 |
| WO | WO 2009/005551 | 1/2009 |
| WO | WO 2009/016118 | 2/2009 |
| WO | WO 2009/079011 | 6/2009 |
| WO | WO 2009/123776 | 10/2009 |
| WO | WO 2009/158118 | 12/2009 |
| WO | WO 2010/135014 | 11/2010 |
| WO | WO 2011/099832 | 8/2011 |
| WO | WO 2011/123609 | 10/2011 |
| WO | WO 2011/149856 | 12/2011 |
| WO | WO 2012/051410 | 4/2012 |
| WO | WO 2012/074126 | 6/2012 |
| WO | WO 2012/170867 | 12/2012 |
| WO | WO 2013/129674 | 9/2013 |
| WO | WO 2013/180193 | 12/2013 |
| WO | WO 2014/149207 | 9/2014 |
| WO | WO 2014/153529 | 9/2014 |
| WO | WO 2014/182954 | 11/2014 |
| WO | WO 2015/008872 | 1/2015 |

OTHER PUBLICATIONS

Blom et al., "Preparative LC-MS Purification: Improved Compound-Specific Method Optimization," J. Comb. Chem., 2004, 6: 874-883.

Blom, "Two-Pump at-Column-Dilution Configuration for Preparative Liquid Chromatography-Mass Spectrometry," J. Comb. Chem., 2002, 4: 295-301.

Brock et al., "Roles of G beta gamma in membrane recruitment and activation of p110 gamma/p101 phosphoinositide 3-kinase gamma," J Cell Biol, Jan. 2003, 160(1): 89-99.

Camps et al., "Blockade of PI3Kγ suppresses joint inflammation and damage in mouse models of rheumatoid arthritis," Nature Medicine, Sep. 2005, 11(9): 936-943.

Cantley, "The phosphoinositide 3-kinase pathway," Science, May 2002, 296(5573): 1655-7.

Carter et al., "Prioritization of driver mutations in pancreatic cancer using cancer-specific high-throughput annotation of somatic mutations (CHASM)," Cancer Biol Ther, Sep. 2010, 10(6): 582-7.

Collier et al., "Structural Basis for Isoform Selectivity in a Class of Benzothiazole Inhibitors of Phosphoinositide 3-Kinase [gamma]," Journal of Medicinal Chemistry, Jan. 2015, 58(1): 517-521.

Comerford et al., "PI3Kγ drives priming and survival of autoreactive CD4(+) T cells during experimental autoimmune encephalomyelitis," PLoS One, 2012, 7(9): e45095.

Database Registry [online], Chemical Abstracts Service, Columbus, OH, US; Aug. 2012, CAS client services: XP002755356, Database accession No. 1391828-67-3.

Database Registry [online], Chemical Abstracts Service, Columbus, OH, US; Dec. 2011, Chemical Catalog; Supplier: Ukrorgsyntez ltd.: XP002755357, Database accession No. 1347088-14-5.

Database Registry [online], Chemical Abstracts Service, Columbus, OH, US; Dec. 2012, Chemical Catalog; Supplier: Aurora Fine Chemicals: XP002755355, Database accession No. 1411464-90-8.

Database Registry [online], Chemical Abstracts Service, Columbus, OH, US; Feb. 2014, Chemical Catalog; Supplier: Aurora Fine Chemicals: XP002755346, Database accession No. 1554931-95-1.

Database Registry [online], Chemical Abstracts Service, Columbus, OH, US; Feb. 2014, Chemical Catalog; Supplier: Aurora Fine Chemicals: XP002755347, Database accession No. 1540856-06-1.

Database Registry [online], Chemical Abstracts Service, Columbus, OH, US; Feb. 2014, Chemical Catalog; Supplier: Aurora Fine Chemicals: XP002755349, Database accession No. 1538237-68-1.

Database Registry [online], Chemical Abstracts Service, Columbus, OH, US; Feb. 2014, Chemical Catalog; Supplier: Aurora Fine Chemicals: XP002755350, Database accession No. 1536955-67-5.

Database Registry [online], Chemical Abstracts Service, Columbus, OH, US; Jan. 2014, Chemical Catalog; Supplier: Aurora Fine Chemicals: XP002755351, Database accession No. 1528719-88-1.

Database Registry [online], Chemical Abstracts Service, Columbus, OH, US; Jan. 2014, Chemical Catalog; Supplier: Aurora Fine Chemicals: XP002755352, Database accession No. 1526778-80-2.

Database Registry [online], Chemical Abstracts Service, Columbus, OH, US; Jan. 2014, Chemical Catalog; Supplier: Aurora Fine Chemicals: XP002755353, Database accession No. 1522493-70-4.

Database Registry [online], Chemical Abstracts Service, Columbus, OH, US; Jan. 2014, Chemical Catalog; Supplier: Aurora Fine Chemicals: XP002755354, Database accession No. 1520181-20-7.

Database Registry [online], Chemical Abstracts Service, Columbus, OH, US; Oct. 2005, Chemical Library; Supplier: interchim: XP002755358, Database accession No. 866138-38-7.

Database Registry [online], Chemical Abstracts Service, Columbus, OH, US; Oct. 2005, Chemical Library; Supplier: interchim: XP002755359, Database accession No. 864939-76-4.

Database Registry [online], Chemical Abstracts Service, Columbus, Ohio, US, Feb. 2010, Chemical Catalog; Supplier: Aurora Fine Chemicals: XP002755348, Database accession No. 1540777-22-7.

Doukas et al., "Aerosolized phosphoinositide 3-kinase gamma/delta inhibitor TG100-115 [3-[2,4-diamino-6-(3-hydroxyphenyl)pteridin-7-yl]phenol] as a therapeutic candidate for asthma and chronic obstructive pulmonary disease," J Pharmacol Exp Ther, Mar. 2009, 328(3): 758-65.

Doukas et al., "Phosphoinositide 3-kinase gamma/delta inhibition limits infarct size after myocardial ischemia/reperfusion injury," Proc Natl Acad Sci USA, Dec. 2006, 103(52): 19866-71.

El Khoury et al., "Ccr2 deficiency impairs microglial accumulation and accelerates progression of Alzheimer-like disease," Nat Med, Apr. 2007, 13(4): 432-8.

Falasca and Maffucci, "Targeting p110gamma in gastrointestinal cancers: attack on multiple fronts," Frontiers in Physiology, 2014, 5: 1-10.

Giri et al "Mechanism of amyloid peptide induced CCR5 expression in monocytes and its inhibition by siRNA for Egr-1," Am J Physiol Cell Physiol, Aug. 2005, 289(2): C264-76.

Gonzalez-Garcia et al., "Phosphatidylinositol 3-Kinase Inhibition Ameliorates Inflammation and Tumor Growth in a Model of Colitis-Associated Cancer," Gastroenterology, 2010, 138: 1373-1384.

Hanahan and Weinberg, "Hallmarks of Cancer: The Next Generation," Cell, 2011, 144: 646-674.

Hayer et al., "PI3Kgamma regulates cartilage damage in chronic inflammatory arthritis," FASEB J, Dec. 2009, 23(12): 4288-98.

International Search Report and Written Opinion in International Application No. PCT/US2016/017073, dated Apr. 15, 2016, 21 pages.

Jimenez et al., "The p85 regulatory subunit controls sequential activation of phosphoinositide 3-kinase by Tyr kinases and Ras," J Biol Chem, Nov. 2002, 277(44): 41556-62.

Kaneda et al., Cancer Res., 74 (Suppl 19: Abstact 3650).

Kumar et al., "Discovery and optimization of a new class of pyruvate kinase inhibitors as potential therapeutics for the treatment of methicillin-resistant*Staphylococcus aureus*infections," Bioorganic & Medicinal Chemistry, Jan. 2014, 22(5): 1708-1725.

Laffargue et al., "Phosphoinositide 3-kinase gamma is an essential amplifier of mast cell function," Immunity, Mar. 2002, 16(3): 441-51.

Li et al., "PI3Kγ inhibition alleviates symptoms and increases axon number in experimental autoimmune encephalomyelitis mice," Neuroscience, Dec. 2013, 253: 89-99.

Lupia et al., "Ablation of phosphoinositide 3-kinase-gmma reduces the severity of acute pancreatitis," Am J Pathol, Dec. 2004, 165(6): 2003-11.

Mamedov et al., "Acid-catalyzed rearrangement of 3-(beta-2-aminostyryl)quinoxalin-2(1H)ones—a new and efficient method for the synthesis of 2-benzimidazol-2-ylquinolines," Tetrahedron Letters, Dec. 2010, 51(50): 6503-6506.

Martin et al., "PI3Kγ mediates kaposi's sarcoma-associated herpesvirus vGPCR-induced sarcomagenesis," Cancer Cell, Jun. 2011, 19(6): 805-13.

(56) References Cited

OTHER PUBLICATIONS

Passos et al., "Involvement of phophoinositide 3-kinase gamma in the neuro-inflammatory response and cognitive impairments induced by beta-amyloid 1-40 peptide in mice," Brain Behav Immun, Mar. 2010, 24(3): 493-501.

Pinho et al., "Phosphoinositide-3 kinases critically regulate the recruitment and survival of eosinophils in vivo: importance for the resolution of allergic inflammation," J Leukoc Biol, May 2005, 77(5): 800-10.

Prete et al., "Defective dendritic cell migration and activation of adaptive immunity in PI3Kgamma-deficient mice," EMBO J, Sep. 2004, 23(17): 3505-15.

Randis et al., "Role of PI3Kdelta and PI3Kgamma in inflammatory arthritis and tissue localization of neutrophils," Eur J Immunol, May 2008, 38(5): 1215-24.

Remington's Pharmaceutical Sciences, 17th ed., Mack Publishing Company, Easton, Pa., 1985, p. 1418.

Rodrigues et al., "Absence of PI3Kgamma leads to increased leukocyte apoptosis and diminished severity of experimental autoimmune encephalomyelitis," J Neuroimmunol, May 2010, 222(1-2)90-4.

Schmid et al., "Receptor tyrosine kinases and TLR/IL1Rs unexpectedly activate myeloid cell PI3Kγ, a single convergent point promoting tumor inflammation and progression," Cancer Cell, Jun. 2011, 19(6): 715-27.

Schmidt et al., Cancer Res. 2012, 72 (Suppl 1: Abstract, 411).

Subramaniam et al., "Targeting nonclassical oncogenes for therapy in T-ALL," Cancer Cell, Apr. 2012, 21(4): 459-72.

T. W. Greene and P. G. M. Wuts, Protective Groups in Organic Synthesis, 3rd Ed., Wiley & Sons, Inc., New York (1999) **Too Voluminous to Provide.

Thomas et al., "Airway inflammation: chemokine-induced neutrophilia and the class I phosphoinositide 3-kinases," Eur J Immunol, Apr. 2005, 35(4): 1283-91.

Vaillard et al., "Synthesis of 6-substituted 2-pyrrolyl and Indolyl Benzoxazoles by Intramolecular O-Arylation in Photostimulated Reactions," The Journal of Organic Chemistry, Feb. 2012, 77(3): 1507-1519.

Vanhaesebroeck et al., "Signalling by PI3K isoforms: insights from gene-targeted mice," Trends Biochem Sci, Apr. 2005, 30(4): 194-204.

Vecchione et al., "Protection from angiotensin II-mediated vasculotoxic and hypertensive response in mice lacking PI3Kgamma," J Exp Med, Apr. 2005, 201(8): 1217-28.

Collier et al., "Discovery of Highly Isoform Selective Thiazolopiperidine Inhibitors of Phosphoinositide 3-Kinase γ," Journal of Medicinal Chemistry, 2015, 58: 5684-5688.

Cushing et al., "PI3Kδ and PI3Kγ as Targets for Autoimmune and Inflammatory Diseases," Journal of Medicinal Chemistry, 2012, 55: 8559-8581.

* cited by examiner

AZA-HETEROARYL COMPOUNDS AS PI3K-GAMMA INHIBITORS

This application claims the benefit of U.S. Ser. No. 62/113,995, filed Feb. 9, 2015, which is incorporated herein by reference in its entirety.

TECHNICAL FIELD

The present invention provides heterocyclic compounds that modulate the activity of phosphoinositide 3-kinases-gamma (PI3Kγ) and are useful in the treatment of diseases related to the activity of PI3Kγ including, for example, autoimmune diseases, cancer, cardiovascular diseases, and neurodegenerative diseases.

BACKGROUND

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4):194-204).

Expression of PI3Kγ is mainly restricted to hematopoietic system, although it can be also detected at lower level in endothelium, heart and brain. PI3Kγ knock-out or kinase dead knock in mice are normal and fertile and do not present any overt adverse phenotypes. Analysis at the cellular level indicates that PI3Kγ is required for GPCR ligand-induced PtdINs (3,4,5)P3 production, chemotaxis and respiratory burst in neutrophils. PI3Kγ-null macrophages and dendritic cell exhibit reduced migration towards various chemoattractants. T-cells deficient in PI3Kγ show impaired cytokine production in response to anti-CD3 or Con A stimulation. PI3Kγ working downstream of adenosine A3A receptor is critical for sustained degranulation of mast cells induced by FCεRI cross-linking with IgE. PI3Kγ is also essential for survival of eosinophils (Ruckle et al., Nat. Rev. Drug Discovery, 2006, 5, 903-918)

Given its unique expression pattern and cellular functions, the potential role of PI3Kγ in various autoimmune and inflammatory disease models has been investigated with genetic and pharmacological tools. In asthma and allergy models, PI3Kγ$^{-/-}$ mice or mice treated with PI3Kγ inhibitor showed a defective capacity to mount contact hypersensitivity and delayed-type hypersensitivity reactions. In these models, PI3Kγ was shown to be important for recruitment of neutrophils and eosinophils to airways and degranulation of mast cells (see e.g. Laffargue et al., Immunity, 2002, 16, 441-451; Prete et al., The EMBO Journal, 2004, 23, 3505-3515; Pinho et al., L. Leukocyte Biology, 2005, 77, 800-810; Thomas et al., Eur. J. Immunol. 2005, 35, 1283-1291; Doukas et al., J. Pharmacol. Exp Ther. 2009, 328, 758-765).

In two different acute pancreatitis models, genetic ablation of PI3Kγ significantly reduced the extent of acinar cell injury/necrosis and neutrophil infiltration without any impact on secretive function of isolated pancreatic acini (Lupia et al., Am. J. Pathology, 2004, 165, 2003-2011). PI3Kγ$^{-/-}$ mice were largely protected in four different models of rheumatoid arthritis (CIA, α-CII-IA, K/BxN serum transfer and TNF transgenic) and PI3Kγ inhibition suppressed the progression of joint inflammation and damage in the CIA and α-CII-IA models (see e.g., Camps et al., Nat. Medicine, 2005, 11, 939-943; Randis et al., Eur. J. Immunol, 2008, 38, 1215-1224; Hayer et al., FASB J., 2009, 4288-4298). In the MRL-lpr mouse model of human systemic lupus erythematous, inhibition of PI3Kγ reduced glomerulonephritis and prolonged life span (Barber et al., Nat. Medicine, 2005, 9, 933-935).

There is evidence suggesting that chronic inflammation due to infiltration by myeloid-derived cells is a key component in the progression of neurodegeneration diseases, such as Alzheimer's disease (AD) (Giri et al., Am. J. Physiol. Cell Physiol., 2005, 289, C264-C276; El Khoury et al., Nat. Med., 2007, 13, 432-438). In line with this suggestion, PI3Kγ inhibition was shown to attenuate Aβ(1-40)-induced accumulation of activated astrocytes and microglia in the hippocampus and prevent the peptide-induced congnitive deficits and synaptic dysfunction in a mouse model of AD (Passos et al., Brain Behav. Immun. 2010, 24, 493-501). PI3Kγ deficiency or inhibition also was shown to delay onset and alleviate symptoms in experimental autoimmune encephalomyelitis in mice, a mouse model of human multiple sclerosis, which is another form of neurodegeneration disease (see e.g., Rodrigues et al., J. Neuroimmunol. 2010, 222, 90-94; Berod et al., Euro. J. Immunol. 2011, 41, 833-844; Comerford et al., PLOS one, 2012, 7, e45095; Li et al., Neuroscience, 2013, 253, 89-99).

Chronic inflammation has been formally recognized as one of the hallmarks for many different types of cancers. Accordingly, selective anti-inflammatory drugs represent a novel class of anti-cancer therapies (Hanahan and Weinberg, Cell, 2011, 144, 646-674). Since PI3Kγ is reported to mediate various inflammatory processes, its role as an immune oncology target has also been investigated. A recent study reported that PI3Kγ deficiency suppressed tumor growth in the syngeneic models of lung cancer, pancreatic cancer and melanoma (LLC, PAN02 and B16). PI3Kγ deficiency or inhibition also inhibited tumor growth in a spontaneous breast cancer model (Schmid et al., Cancer Cell, 2011, 19, 715-727). A further study reported that PI3Kγ deficiency could ameliorate inflammation and tumor growth in mice having colitis-associated colon cancer, (Gonzalez-Garcia et al., Gastroenterology, 2010, 138, 1373-1384). Detailed mechanistic analysis indicates that tumor infiltration by CD11b$^+$ myeloid cells can cause protumorigenic inflammation at tumor sites and PI3Kγ in the myeloid cells is critical in mediating signaling of various chemoattractants in bring the cells to the tumor (Schmid et al., Cancer Cell, 2011, 19, 715-727). Other studies suggest that PI3Kγ is also required for differentiation of naive myeloid cells into M2 macrophages at tumor sites. M2 macrophages promote tumor growth and progression by secreting immunosuppressive factors such arginase 1, which depletes the tumor microenvironment of arginine, thereby promoting T-cell death and NK cell inhibition (Schmidt et al., *Cancer Res.* 2012, 72 (*Suppl* 1: *Abstract,* 411; Kaneda et al., *Cancer Res.,* 74 (*Suppl* 19: *Abstract* 3650)).

In addition to its potential role in promoting protumorigenic microenvironment, PI3Kγ may play a direct role in cancer cells. PI3Kγ is reported to be required for signaling from the Kaposi's sarcoma-associated herpevirus encoded vGPCR oncogene and tumor growth in a mouse model of sarcoma (Martin et al., *Cancer Cell,* 2011, 19, 805-813). PI3Kγ was also suggested to be required for growth of T-ALL (Subramanjam et al., *Cancer Cell,* 2012, 21, 459-472), PDAC and HCC cells (Falasca and Maffucci, *Frontiers in Physiology,* 2014, 5, 1-10). Moreover, in a survey of driver mutations in pancreatic cancer, PI3Kγ gene was found to contain second highest scoring predicted driven mutation (R839C) among the set of genes not previously identified as a driver in pancreatic cancer (Carter et al., *Cancer Biol. Ther.* 2010, 10, 582-587).

Finally, PI3Kγ deficiency also has been reported to offer protection to experimental animals in different cardiovascular disease models. For examples, lack of PI3Kγ would reduce angiotension-evoked smooth muscle contraction and, therefore, protect mice from angiotension-induced hypertension (Vecchione et al., *J. Exp. Med.* 2005, 201, 1217-1228). In rigorous animal myocardial infarction models, PI3Kγ inhibition provided potent cardioprotection, reducing infarct development and preserving myocardial function (Doukas et al., *Proc. Natl. Acad. Sci. USA,* 2006, 103, 19866-19871).

For these reasons, there is a need to develop new PI3Kγ inhibitors that can be used for the treatment of diseases such as cancer, autoimmune disorders, and inflammatory and cardiac diseases. This application is directed to this need and others.

SUMMARY

The present invention related to, inter alia, compounds of Formula I:

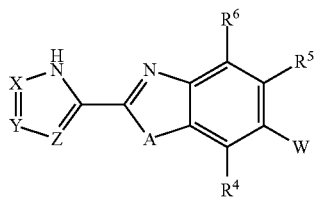

or pharmaceutically acceptable salts thereof, wherein constituent members are defined herein.

The present invention further provides pharmaceutical compositions comprising a compound of Formula I, or a pharmaceutically acceptable salt thereof, and a pharmaceutically acceptable carrier.

The present invention further provides methods of inhibiting an activity of PI3Kγ kinase comprising contacting the kinase with a compound of Formula I, or a pharmaceutically acceptable salt thereof.

The present invention further provides methods of treating a disease or a disorder associated with abnormal PI3Kγ kinase expression or activity in a patient by administering to a patient a therapeutically effective amount of a compound of Formula I, or a pharmaceutically acceptable salt thereof.

The present invention further provides a compound of Formula I, or a pharmaceutically acceptable salt thereof, for use in any of the methods described herein.

The present invention further provides use of a compound of Formula I, or a pharmaceutically acceptable salt thereof, for the preparation of a medicament for use in any of the methods described herein.

DETAILED DESCRIPTION

The present invention provides, inter alia, a compound of Formula I:

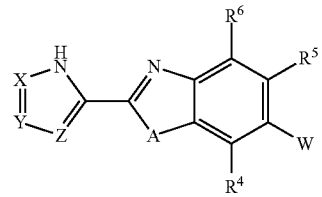

or a pharmaceutically acceptable salt thereof, wherein:

X is N or $CR^1$;

Y is N or $CR^2$;

Z is N or $CR^3$;

$R^1$, $R^2$, and $R^3$ are each independently selected from H, halo, CN, $NO_2$, $C_{1-6}$ alkyl, $C_{2-6}$ alkenyl, $C_{2-6}$ alkynyl, $C_{1-6}$ haloalkyl, $Cy^2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)OR^{b1}$, $NR^{c1}C(O)OR^{a1}$, $NR^{c1}C(O)NR^{c1}R^{d1}$, —$NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2 or 3 independently selected $R^{10}$ groups; or alternatively, $R^1$ and $R^2$, taken together with the carbon atoms to which they are attached, form a phenyl, $C_{3-6}$ cycloalkyl, or a 5-6-membered heteroaryl ring, which is optionally substituted by 1, 2, or 3 independently selected $R^{11}$ groups; or alternatively, $R^2$ and $R^3$, taken together with the carbon atoms to which they are attached, form a phenyl or a 5-6-membered heteroaryl ring, which is optionally substituted by 1, 2, or 3 independently selected $R^{11}$ groups;

A is O, S, or $CR^7$=$CR^8$;

$R^4$, $R^5$, and $R^6$ are each independently selected from H, OH, $NO_2$, CN, halo, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^7$ and $R^8$ are independently selected from H, halo, CN, $C_{1-6}$ alkyl, $C_{1-6}$ haloalkyl, OH, $C_{1-6}$ alkoxy, and $C_{1-6}$ haloalkoxy;

W is halo or Cy;

Cy is phenyl, naphthyl, 5-10 membered heteroaryl, or 4-10 membered heterocycloalkyl, each of which is optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $Cy^1$, —($C_{1-4}$ alkylene)-$Cy^1$, CN, $NO_2$, $OR^a$, $SR^a$, $P(O)R^aR^b$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl as the substituent of Cy is further substituted by 1 or 2 independently selected $R^g$ groups;

each $R^{10}$ is independently selected from halo, CN, $NO_2$, $Cy^2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, —$NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

each $R^{11}$ is independently selected from halo, CN, $NO_2$, $C_{1-6}$ alkyl, $C_{2-6}$ alkenyl, $C_{2-6}$ alkynyl, $C_{1-6}$ haloalkyl, $OR^{a2}$, $SR^{a2}$, $C(O)OR^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2 or 3 independently selected $R^{12}$ groups;

each $R^{12}$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^a$, $R^c$, and $R^d$ is independently selected from H, $C_{1-6}$ alkyl, $C_{2-6}$ alkenyl, $C_{2-6}$ alkynyl, $C_{1-4}$ haloalkyl, $Cy^1$, and —($C_{1-4}$ alkylene)-$Cy^1$; wherein said $C_{1-6}$ alkyl, $C_{2-6}$ alkenyl, and $C_{2-6}$ alkynyl are each optionally substituted with 1, 2, 3, or 4 independently selected $R^g$ groups;

each $R^b$ is independently selected from $C_{1-6}$ alkyl, $C_{2-6}$ alkenyl, $C_{2-6}$ alkynyl, $C_{1-4}$ haloalkyl, $Cy^1$, and —($C_{1-4}$ alkylene)-$Cy^1$; wherein said $C_{1-6}$ alkyl, $C_{2-6}$ alkenyl, and $C_{2-6}$ alkynyl are each optionally substituted with 1, 2, 3, or 4 independently selected $R^g$ groups; or alternatively, any $R^c$ and $R^d$ attached to the same N atom, together with the N atom to which they are attached, form a 4-6 membered heterocycloalkyl group or a 5-6 membered heteroaryl group, each optionally substituted with 1, 2, or 3 independently selected $R^g$ groups;

each $R^e$ is independently selected from H, CN, $C_{1-6}$ alkyl, $C_{1-6}$ haloalkyl, $C_{1-6}$ alkylthio, $C_{1-6}$ alkyl sulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^{a1}$, $R^{c1}$ and $R^{d1}$ are independently selected from H, $C_{1-6}$ alkyl, $C_{2-6}$ alkenyl, $C_{2-6}$ alkynyl, $C_{1-4}$ haloalkyl, and $Cy^3$; wherein said $C_{1-6}$ alkyl, $C_{2-6}$ alkenyl, and $C_{2-6}$ alkynyl are each optionally substituted with 1, 2 or 3 independently selected $R^{12}$ groups;

each $R^{b1}$ is independently selected from $C_{1-6}$ alkyl, $C_{2-6}$ alkenyl, $C_{2-6}$ alkynyl, $C_{1-4}$ haloalkyl, and $Cy^3$; wherein said $C_{1-6}$ alkyl, $C_{2-6}$ alkenyl, and $C_{2-6}$ alkynyl are each optionally substituted with 1, 2 or 3 independently selected $R^{12}$ groups;

or alternatively, any $R^{c1}$ and $R^{d1}$ attached to the same N atom, together with the N atom to which they are attached, form a 4-, 5-, 6- or 7-membered heterocycloalkyl group optionally substituted with 1, 2 or 3 independently selected $R^{12}$ groups;

each $R^{a2}$, $R^{c2}$, and $R^{d2}$ is independently selected from H, $C_{1-6}$ alkyl, $C_{2-6}$ alkenyl, $C_{2-6}$ alkynyl, and $C_{1-4}$ haloalkyl; wherein said $C_{1-6}$ alkyl, $C_{2-6}$ alkenyl, and $C_{2-6}$ alkynyl are each optionally substituted with 1, 2 or 3 independently selected $R^{12}$ groups;

each $R^{b2}$ is independently selected from $C_{1-6}$ alkyl, $C_{2-6}$ alkenyl, $C_{2-6}$ alkynyl, and $C_{1-4}$ haloalkyl; wherein said $C_{1-6}$ alkyl, $C_{2-6}$ alkenyl, and $C_{2-6}$ alkynyl are each optionally substituted with 1, 2 or 3 independently selected $R^{12}$ groups;

or alternatively, any $R^{c2}$ and $R^{d2}$ attached to the same N atom, together with the N atom to which they are attached, form a 4-, 5-, 6- or 7-membered heterocycloalkyl group optionally substituted with 1, 2 or 3 independently selected $R^{12}$ groups;

each $Cy^1$ is independently selected from phenyl, 5-6 membered heteroaryl, $C_{3-7}$ cycloalkyl, and 4-6 membered heterocycloalkyl, each optionally substituted by 1, 2, 3, or 4 independently selected $R^g$ groups;

each $Cy^2$ is independently selected from phenyl, $C_{3-7}$ cycloalkyl, 5-6 membered heteroaryl, and 4-6 membered heterocycloalkyl; wherein said phenyl, 5-6 membered heteroaryl, $C_{3-7}$ cycloalkyl, and 4-6 membered heterocycloalkyl are each optionally substituted with 1, 2 or 3 independently selected $R^{11}$ groups;

each $Cy^3$ is independently selected from phenyl, $C_{3-7}$ cycloalkyl, 5-6 membered heteroaryl, and 4-6 membered heterocycloalkyl; wherein said phenyl, 5-6 membered heteroaryl, $C_{3-7}$ cycloalkyl, and 4-6 membered heterocycloalkyl are each optionally substituted with 1, 2 or 3 independently selected $C_{1-4}$ alkylene-$R^{12}$ or $R^{12}$ groups; and each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkyl sulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments:

X is N or $CR^1$;

Y is N or $CR^2$;

Z is N or $CR^3$;

$R^1$, $R^2$, and $R^3$ are each independently selected from H, halo, CN, $NO_2$, $C_{1-6}$ alkyl, $C_{2-6}$ alkenyl, $C_{2-6}$ alkynyl, $C_{1-6}$ haloalkyl, $Cy^2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2 or 3 independently selected $R^{10}$ groups; or alternatively, $R^1$ and $R^2$, taken together with the carbon atoms to which they are attached, form a phenyl or a 5-6-membered heteroaryl ring, which is optionally substituted by 1, 2, or 3 independently selected $R^{11}$ groups; or alternatively, $R^2$ and $R^3$, taken together with the carbon atoms to which they are attached, form a phenyl or a 5-6-membered heteroaryl ring, which is optionally substituted by 1, 2, or 3 independently selected $R^{11}$ groups;

A is O, S, or $CR^7=CR^8$;

$R^4$, $R^5$, and $R^6$ are each independently selected from H, OH, $NO_2$, CN, halo, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^7$ and $R^8$ are independently selected from H, halo, CN, $C_{1-6}$ alkyl, $C_{1-6}$ haloalkyl, OH, $C_{1-6}$ alkoxy, and $C_{1-6}$ haloalkoxy;

W is halo or Cy;

Cy is phenyl, naphthyl, 5-10 membered heteroaryl, or 4-10 membered heterocycloalkyl, each of which is optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $Cy^1$, —($C_{1-4}$ alkylene)-$Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^{10}$ is independently selected from halo, CN, $NO_2$, $Cy^2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2 R^{b1}$, and $S(O)_2NR^{c1}R^{d1}$;

each is independently selected from halo, CN, $NO_2$, $C_{1-6}$ alkyl, $C_{2-6}$ alkenyl, $C_{2-6}$ alkynyl, $C_{1-6}$ haloalkyl, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2 or 3 independently selected $R^{12}$ groups;

each $R^{12}$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^a$, $R^c$, and $R^d$ is independently selected from H, $C_{1-6}$ alkyl, $C_{2-6}$ alkenyl, $C_{2-6}$ alkynyl, $C_{1-4}$ haloalkyl, $Cy^1$, and —($C_{1-4}$ alkylene)-$Cy^1$; wherein said $C_{1-6}$ alkyl, $C_{2-6}$ alkenyl, and $C_{2-6}$ alkynyl are each optionally substituted with 1, 2, 3, or 4 independently selected $R^g$ groups;

each $R^b$ is independently selected from $C_{1-6}$ alkyl, $C_{2-6}$ alkenyl, $C_{2-6}$ alkynyl, $C_{1-4}$ haloalkyl, $Cy^1$, and —($C_{1-4}$ alkylene)-$Cy^1$; wherein said $C_{1-6}$ alkyl, $C_{2-6}$ alkenyl, and $C_{2-6}$ alkynyl are each optionally substituted with 1, 2, 3, or 4 independently selected $R^g$ groups; or alternatively, any $R^c$ and $R^d$ attached to the same N atom, together with the N atom to which they are attached, form a 4-6 membered heterocycloalkyl group or a 5-6 membered heteroaryl group, each optionally substituted with 1, 2, or 3 independently selected $R^g$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^{a1}$, $R^{c1}$ and $R^{d1}$ are independently selected from H, $C_{1-6}$ alkyl, $C_{2-6}$ alkenyl, $C_{2-6}$ alkynyl, $C_{1-4}$ haloalkyl, and $Cy^3$; wherein said $C_{1-6}$ alkyl, $C_{2-6}$ alkenyl, and $C_{2-6}$ alkynyl are each optionally substituted with 1, 2 or 3 independently selected $R^{12}$ groups;

each $R^{b1}$ is independently selected from $C_{1-6}$ alkyl, $C_{2-6}$ alkenyl, $C_{2-6}$ alkynyl, $C_{1-4}$ haloalkyl, and $Cy^3$; wherein said $C_{1-6}$ alkyl, $C_{2-6}$ alkenyl, and $C_{2-6}$ alkynyl are each optionally substituted with 1, 2 or 3 independently selected $R^{12}$ groups; or alternatively, any $R^{c1}$ and $R^{d1}$ attached to the same N atom, together with the N atom to which they are attached, form a 4-, 5-, 6- or 7-membered heterocycloalkyl group optionally substituted with 1, 2 or 3 independently selected $R^{12}$ groups;

each $R^{a2}$, $R^{c2}$, and $R^{d2}$ is independently selected from H, $C_{1-6}$ alkyl, $C_{2-6}$ alkenyl, $C_{2-6}$ alkynyl, and $C_{1-4}$ haloalkyl; wherein said $C_{1-6}$ alkyl, $C_{2-6}$ alkenyl, and $C_{2-6}$ alkynyl are each optionally substituted with 1, 2 or 3 independently selected $R^{12}$ groups;

each $R^{b2}$ is independently selected from $C_{1-6}$ alkyl, $C_{2-6}$ alkenyl, $C_{2-6}$ alkynyl, and $C_{1-4}$ haloalkyl; wherein said $C_{1-6}$ alkyl, $C_{2-6}$ alkenyl, and $C_{2-6}$ alkynyl are each optionally substituted with 1, 2 or 3 independently selected $R^{12}$ groups; or alternatively, any $R^{c2}$ and $R^{d2}$ attached to the same N atom, together with the N atom to which they are attached, form a 4-, 5-, 6- or 7-membered heterocycloalkyl group optionally substituted with 1, 2 or 3 independently selected $R^{12}$ groups;

each $Cy^1$ is independently selected from phenyl, 5-6 membered heteroaryl, $C_{3-7}$ cycloalkyl, and 4-6 membered heterocycloalkyl, each optionally substituted by 1, 2, 3, or 4 independently selected $R^g$ groups;

each $Cy^2$ is independently selected from phenyl, $C_{3-7}$ cycloalkyl, 5-6 membered heteroaryl, and 4-6 membered heterocycloalkyl; wherein said phenyl, 5-6 membered heteroaryl, $C_{3-7}$ cycloalkyl, and 4-6 membered heterocycloalkyl are each optionally substituted with 1, 2 or 3 independently selected $R^{11}$ groups;

each $Cy^3$ is independently selected from phenyl, $C_{3-7}$ cycloalkyl, 5-6 membered heteroaryl, and 4-6 membered heterocycloalkyl; wherein said phenyl, 5-6 membered heteroaryl, $C_{3-7}$ cycloalkyl, and 4-6 membered heterocycloalkyl are each optionally substituted with 1, 2 or 3 independently selected $C_{1-4}$ alkylene-$R^{12}$ or $R^{12}$ groups; and each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^1$ is H, OH, $NO_2$, CN, halo, $C_{1-6}$ alkyl, $C_{1-6}$ haloalkyl, $C_{1-6}$ alkoxy, $C_{1-4}$ haloalkoxy, phenyl, $C_{3-6}$ cycloalkyl, 5-6 membered heteroaryl, or 4-6 membered heterocycloalkyl.

In some embodiments, $R^1$ is H, OH, methyl, ethyl, cyclopropyl, phenyl, or a tetrahydrofuran ring.

In some embodiments, $R^1$ is H, ethyl, cyclopropyl, phenyl, or a tetrahydrofuran ring.

In some embodiments, $R^2$ is H, OH, $NO_2$, CN, halo, $C_{1-6}$ alkyl, $C_{1-6}$ haloalkyl, $C_{1-6}$ alkoxy, $C_{1-4}$ haloalkoxy, phenyl, $C_{3-6}$ cycloalkyl, 5-6 membered heteroaryl, or 4-6 membered heterocycloalkyl.

In some embodiments, $R^2$ is H, methyl, or phenyl.

In some embodiments, $R^1$ and $R^2$, together with the carbon atoms to which they are attached, form a phenyl ring, which is optionally substituted by 1, 2, or 3 independently selected $R^{11}$ groups.

In some embodiments, $R^1$ and $R^2$, together with the carbon atoms to which they are attached, form a phenyl ring, which is optionally substituted by 1, 2, or 3 $R^{11}$ groups independently selected from halo, $C_{1-6}$ alkyl, and $C_{1-6}$ haloalkyl.

In some embodiments, $R^1$ and $R^2$, together with the carbon atoms to which they are attached, form a phenyl ring, which is optionally substituted by 1 or 2 $R^{11}$ groups independently selected from F, Cl, Br, $CH_3$, and $CF_3$.

In some embodiments, $R^1$ and $R^2$, together with the carbon atoms to which they are attached, form a $C_{3-6}$ cycloalkyl ring, which is optionally substituted by 1, 2, or 3 independently selected $R^{11}$ groups.

In some embodiments, $R^1$ and $R^2$, together with the carbon atoms to which they are attached, form an unsubstituted $C_{3-6}$ cycloalkyl ring.

In some embodiments, $R^1$ and $R^2$, together with the carbon atoms to which they are attached, form a cyclohexyl ring, which is optionally substituted by 1, 2, or 3 independently selected $R^{11}$ groups.

In some embodiments, $R^1$ and $R^2$, together with the carbon atoms to which they are attached, form an unsubstituted cyclohexyl ring.

In some embodiments, $R^3$ is H, methyl, or ethyl.

In some embodiments, $R^3$ is H.

In some embodiments, $R^4$, $R^5$, and $R^6$ are each H.

In some embodiments, W is halo.

In some embodiments, W is Br.

In some embodiments, W is Cy.

In some embodiments, Cy is phenyl or 6-membered heteroaryl, each of which is optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $Cy^1$, —($C_{1-4}$ alkylene)-$Cy^1$, CN, $NO_2$, $OR^a$, $SR^a$, $P(O)R^aR^b$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl as the substituent of Cy is further substituted by 1 or 2 independently selected $R^g$ groups.

In some embodiments, Cy is phenyl or 6-membered heteroaryl, each of which is optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $Cy^1$, —($C_{1-4}$ alkylene)-$Cy^1$, CN, $NO_2$, $OR^a$, $SR^a$, $C(O)R^b$, $C(O)$ $NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, Cy is 6-membered heteroaryl, which is optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, $Cy^1$, —($C_{1-4}$ alkylene)-$Cy^1$, CN, $NO_2$, $OR^a$, $SR^a$, $P(O)R^aR^b$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl as the substituent of Cy is further substituted by 1 or 2 independently selected $R^g$ groups.

In some embodiments, Cy is 6-membered heteroaryl, which is optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, $Cy^1$, —($C_{1-4}$ alkylene)-$Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, Cy is a pyridine ring, which is optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, $Cy^1$, —($C_{1-4}$ alkylene)-$Cy^1$, CN, $NO_2$, $OR^a$, $SR^a$, $P(O)R^aR^b$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl as the substituent of the pyridine ring is further substituted by 1 or 2 independently selected $R^g$ groups.

In some embodiments, Cy is a pyridine ring, which is optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, $Cy^1$, —($C_{1-4}$ alkylene)-$Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)$ $NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, Cy is a pyridine ring, which is optionally substituted by 1 or 2 substituents independently selected from halo, $C_{1-6}$ alkyl, $C_{1-6}$ haloalkyl, CN, $OR^a$, $P(O)R^aR^b$, $NR^cR^d$, $NR^cC(O)R^b$, $NR^cC(O)NR^cR^d$, $NR^cS(O)_2R^b$, $NR^cS(O)_2NR^cR^d$, $S(O)_2R^b$, and $S(O)_2NR^cR^d$; wherein the $C_{1-6}$ alkyl as the substituent of the pyridine ring is further substituted by 1 or 2 independently selected $R^g$ groups.

In some embodiments, Cy is a pyridine ring, which is optionally substituted by 1 or 2 substituents independently selected from halo, $C_{1-6}$ alkyl, $C_{1-6}$ haloalkyl, CN, $OR^a$, $NR^cR^d$, $NR^cC(O)R^b$, $NR^cC(O)NR^cR^d$, $NR^cS(O)_2R^b$, $NR^cS(O)_2NR^cR^d$, $S(O)_2R^b$, and $S(O)_2NR^cR^d$.

In some embodiments, Cy is a pyridine ring, which is optionally substituted by 1, 2, 3, or 4 substituents independently selected from halo, $C_{1-6}$ alkyl, $C_{1-6}$ haloalkyl, CN, $OR^a$, $P(O)R^aR^b$, $NR^cR^d$, $NR^cC(O)R^b$, $NR^cS(O)_2R^b$, $NR^cS(O)_2NR^cR^d$, $S(O)_2R^b$, and $S(O)_2NR^cR^d$; wherein the $C_{1-6}$ alkyl as the substituent of the pyridine ring is further substituted by 1 or 2 independently selected $R^g$ groups.

In some embodiments, Cy is a pyridine ring, which is optionally substituted by 1, 2, 3, or 4 substituents independently selected from halo, $C_{1-6}$ alkyl, $C_{1-6}$ haloalkyl, CN, $OR^a$, $NR^cR^d$, $NR^cC(O)R^b$, $NR^cS(O)_2R^b$, $NR^cS(O)_2NR^cR^d$, $S(O)_2R^b$, and $S(O)_2NR^cR^d$.

In some embodiments, each $R^g$ group is independently selected from halo, OH, carboxy, $C_{1-6}$ alkyl, and $C_{1-6}$ haloalkyl.

In some embodiments:

each $R^a$ is independently selected from H and $C_{1-6}$ alkyl; wherein said $C_{1-6}$ alkyl is optionally substituted with 1, 2, 3, or 4 independently selected $R^g$ groups;

each $R^c$ and $R^d$ is independently selected from H, $C_{1-6}$ alkyl, and $Cy^1$; wherein said $C_{1-6}$ alkyl is optionally substituted with 1, 2, 3, or 4 independently selected $R^g$ groups;

each $R^b$ is independently selected from $C_{1-6}$ alkyl and $Cy^1$; wherein said $C_{1-6}$ alkyl is optionally substituted with 1, 2, 3, or 4 independently selected $R^g$ groups;

each $Cy^1$ is independently selected from phenyl and 6-membered heterocycloalkyl, each optionally substituted by 1 or 2 independently selected $R^g$ groups; and each $R^g$ group is, independently, $C_{1-6}$ alkyl or halo.

In some embodiments, Cy is a pyridine ring, which is optionally substituted by 1 or 2 groups independently selected from F, Cl, CN, —CF$_3$, —OH, —OCH$_3$, —OCH(CH$_3$)$_2$, —OCHF$_2$, —NH$_2$, —N(CH$_3$)$_2$, —S(O)$_2$CH$_3$, —S(O)$_2$N(CH$_3$)$_2$, —NHC(O)CH$_3$, —N(CH$_3$)S(O)$_2$CH$_2$CH$_3$, —NHS(O)$_3$CH$_2$CF$_3$, P(O)(CH$_3$)$_2$, methylene, methylsulfonyl, ethylsulfonylamino, isopropylsulfonylamino, piperazinylsulfonylamino, morpholinylsulfonylamino, piperdinylsulfonylamino, phenylsulfonylamino, and (dimethylamino)sulfonylamino; wherein said phenylsulfonylamino is optionally substituted by F; said piperazinylsulfonylamino is optionally substituted by CH$_3$; and said methylene is substituted by 1 or 2 groups selected from OH, F, and C(O)OH.

In some embodiments, Cy is a pyridine ring, which is optionally substituted by 1 or 2 groups independently selected from F, Cl, CN, —OH, —OCH$_3$, —OCH(CH$_3$)$_2$, —OCHF$_2$, —N(CH$_3$)$_2$, —S(O)$_2$CH$_3$, —S(O)$_2$N(CH$_3$)$_2$, —NHC(O)CH$_3$, ethylsulfonylamino, isopropylsulfonylamino, piperazinylsulfonylamino, morpholinylsulfonylamino, piperdinylsulfonylamino, phenylsulfonylamino, and (dimethylamino)sulfonylamino; wherein said phenylsulfonylamino is optionally substituted by F; and said piperazinylsulfonylamino is optionally substituted by CH$_3$.

In some embodiments,

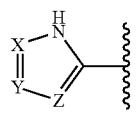

is

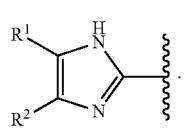

In some embodiments,

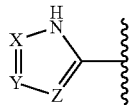

is

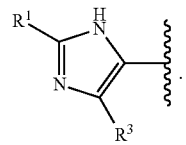

In some embodiments,

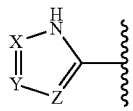

is

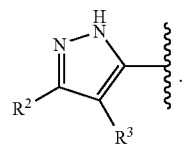

In some embodiments,

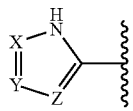

is

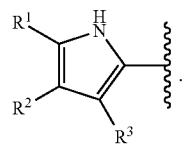

In some embodiments, A is O.
In some embodiments, A is S.
In some embodiments, A is CH═CH.
In some embodiments:

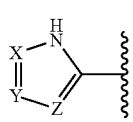

is:

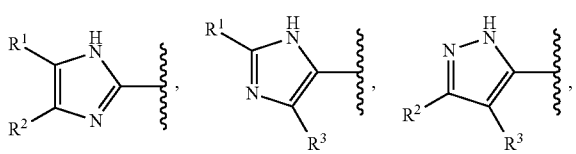

or

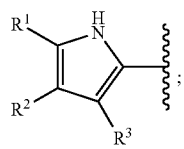

A is O, S, or CH=CH;

R¹ and R² are each independently selected from H, OR$^{a1}$, NO$_2$, CN, halo, C$_{1-6}$ alkyl, C$_{1-6}$ haloalkyl, and Cy²;

R³ is H, methyl, or ethyl;

or R¹ and R², together with the carbon atoms to which they are attached, form a phenyl ring, which is optionally substituted by 1, 2, or 3 independently selected R$^{11}$ groups;

R⁴, R⁵, and R⁶ are each H;

W is Br or Cy;

Cy is 6-membered heteroaryl, which is optionally substituted by 1, 2, or 3 substituents independently selected from halo, C$_{1-6}$ alkyl, C$_{2-6}$ alkenyl, C$_{2-6}$ alkynyl, C$_{1-6}$ haloalkyl, Cy¹, —(C$_{1-4}$ alkylene)-Cy¹, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

each Cy² is independently selected from phenyl, C$_{3-7}$ cycloalkyl, 5-6 membered heteroaryl, and 4-6 membered heterocycloalkyl;

each R$^{11}$ is independently selected from halo, C$_{1-6}$ alkyl, and C$_{1-6}$ haloalkyl;

each R$^{a1}$ is independently selected from H, C$_{1-6}$ alkyl, and C$_{1-4}$ haloalkyl;

each R$^a$, R$^c$, and R$^d$ is independently selected from H, C$_{1-6}$ alkyl, C$_{2-6}$ alkenyl, C$_{2-6}$ alkynyl, C$_{1-4}$ haloalkyl, Cy¹, and —(C$_{1-4}$ alkylene)-Cy¹; wherein said C$_{1-6}$ alkyl, C$_{2-6}$ alkenyl, and C$_{2-6}$ alkynyl are each optionally substituted with 1, 2, 3, or 4 independently selected R$^g$ groups;

each R$^b$ is independently selected from C$_{1-6}$ alkyl, C$_{2-6}$ alkenyl, C$_{2-6}$ alkynyl, C$_{1-4}$ haloalkyl, Cy¹, and —(C$_{1-4}$ alkylene)-Cy¹; wherein said C$_{1-6}$ alkyl, C$_{2-6}$ alkenyl, and C$_{2-6}$ alkynyl are each optionally substituted with 1, 2, 3, or 4 independently selected R$^g$ groups;

or any R$^c$ and R$^d$ together with the N atom to which they are attached form a 4-6 membered heterocycloalkyl group or a 5-6 membered heteroaryl group, each optionally substituted with 1, 2, or 3 independently selected R$^g$ groups;

each R$^e$ is independently selected from H and C$_{1-6}$ alkyl;

each Cy¹ is independently selected from phenyl, 5-6 membered heteroaryl, C$_{3-7}$ cycloalkyl, and 4-6 membered heterocycloalkyl, each optionally substituted by 1, 2, 3, or 4 independently selected R$^g$ groups; and each R$^g$ is independently selected from OH, NO$_2$, CN, halo, C$_{1-6}$ alkyl, C$_{2-6}$ alkenyl, C$_{2-6}$ alkynyl, C$_{1-6}$ haloalkyl, cyano-C$_{1-3}$ alkyl, HO—C$_{1-3}$ alkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino.

In some embodiments:

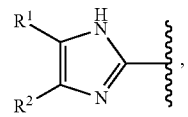

is:

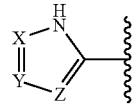

or

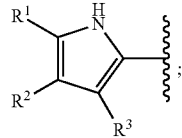

A is O, S, or CH=CH;

R¹ and R² are each independently selected from H, OR$^{a1}$, NO$_2$, CN, halo, C$_{1-6}$ alkyl, C$_{1-6}$ haloalkyl, and Cy²;

R³ is H, methyl, or ethyl;

or R¹ and R², together with the carbon atoms to which they are attached, form a phenyl ring, which is optionally substituted by 1, 2, or 3 independently selected R$^{11}$ groups;

R⁴, R⁵, and R⁶ are each H;

W is Br or Cy;

Cy is a pyridine ring, which is optionally substituted by 1 to 2 substituents independently selected from halo, C$_{1-6}$ alkyl, C$_{1-6}$ haloalkyl, CN, NO$_2$, OR$^a$, C(O)R$^b$, C(O)NR$^c$R$^d$, C(O)OR$^a$, NR$^c$R$^d$, NR$^c$C(O)R$^b$, NR$^c$C(O)OR$^a$, NR$^c$C(O)NR$^c$R$^d$, NR$^c$S(O)$_2$R$^b$, NR$^c$S(O)$_2$NR$^c$R$^d$, S(O)$_2$R$^b$, and S(O)$_2$NR$^c$R$^d$;

each Cy² is independently selected from phenyl, C$_{3-7}$ cycloalkyl, 5-6 membered heteroaryl, and 4-6 membered heterocycloalkyl;

each R$^{11}$ is independently selected from halo, C$_{1-6}$ alkyl, and C$_{1-6}$ haloalkyl;

each R$^{a1}$ is independently selected from H, C$_{1-6}$ alkyl, and C$_{1-4}$ haloalkyl;

each R$^a$ is independently selected from H and C$_{1-6}$ alkyl; wherein said C$_{1-6}$ alkyl is optionally substituted with 1, 2, 3, or 4 independently selected R$^g$ groups;

each R$^c$ and R$^d$ is independently selected from H, C$_{1-6}$ alkyl, and Cy¹; wherein said C$_{1-6}$ alkyl is optionally substituted with 1, 2, 3, or 4 independently selected R$^g$ groups;

each R$^b$ is independently selected from C$_{1-6}$ alkyl and Cy¹; wherein said C$_{1-6}$ alkyl is optionally substituted with 1, 2, 3, or 4 independently selected R$^g$ groups;

each Cy¹ is independently selected from phenyl and 6-membered heterocycloalkyl, each optionally substituted by 1 or 2 independently selected R^g groups; and each R^g is independently selected from OH, NO₂, CN, halo, C_{1-6} alkyl, C_{2-6} alkenyl, C_{2-6} alkynyl, C_{1-6} haloalkyl, C_{1-6} alkoxy, C_{1-6} haloalkoxy, amino, C_{1-6} alkylamino, di(C_{1-6} alkyl)amino, thio, C_{1-6} alkylthio, C_{1-6} alkylsulfinyl, C_{1-6} alkylsulfonyl, carbamyl, C_{1-6} alkylcarbamyl, di(C_{1-6} alkyl)carbamyl, carboxy, C_{1-6} alkylcarbonyl, C_{1-6} alkoxycarbonyl, C_{1-6} alkylcarbonylamino, C_{1-6} alkylsulfonylamino, aminosulfonyl, C_{1-6} alkylaminosulfonyl, di(C_{1-6} alkyl)aminosulfonyl, aminosulfonylamino, C_{1-6} alkylaminosulfonylamino, di(C_{1-6} alkyl)aminosulfonylamino, aminocarbonylamino, C_{1-6} alkylaminocarbonylamino, and di(C_{1-6} alkyl)aminocarbonylamino.

In some embodiments:

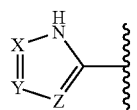

is:

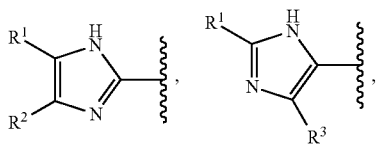

or

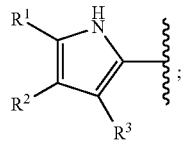

A is O, S, or CH=CH;

R¹ is H, ethyl, cyclopropyl, phenyl, or a tetrahydrofuran ring;

R² is H, methyl, or phenyl; or

R¹ and R², together with the carbon atoms to which they are attached, form a phenyl ring, which is optionally substituted by 1 or 2 independently selected R¹¹ groups.

R³ is H;

R⁴, R⁵, and R⁶ are each H;

W is Br or Cy;

Cy is a pyridine ring, which is optionally substituted by 1 or 2 substituents independently selected from halo, C_{1-6} alkyl, C_{1-6} haloalkyl, CN, OR^a, NR^cR^d, NR^cC(O)R^b, NR^cC(O)NR^cR^d, NR^cS(O)₂R^b, NR^cS(O)₂NR^cR^d, S(O)₂R^b, and S(O)₂NR^cR^d;

each R¹¹ is independently selected from halo, C_{1-6} alkyl, and C_{1-6} haloalkyl;

each R^a is independently selected from H and C_{1-6} alkyl; wherein said C_{1-6} alkyl is optionally substituted with 1, 2, 3, or 4 independently selected R^g groups;

each R^c and R^d is independently selected from H, C_{1-6} alkyl, and Cy¹; wherein said C_{1-6} alkyl is optionally substituted with 1, 2, 3, or 4 independently selected R^g groups;

each R^b is independently selected from C_{1-6} alkyl and Cy¹; wherein said C_{1-6} alkyl is optionally substituted with 1, 2, 3, or 4 independently selected R^g groups;

each Cy¹ is independently selected from phenyl and 6-membered heterocycloalkyl, each optionally substituted by 1 or 2 independently selected R^g groups; and each R^g is, independently, C_{1-6} alkyl or halo.

In some embodiments:

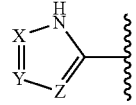

is:

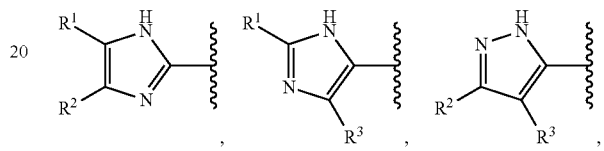

or

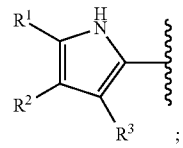

A is O, S, or CH=CH;

R¹ is H, methyl, ethyl, cyclopropyl, phenyl, or a tetrahydrofuran ring;

R² is H, methyl, propyl, or phenyl; or

R¹ and R², together with the carbon atoms to which they are attached, form a phenyl ring or cyclohexene ring, which is optionally substituted by 1 or 2 independently selected R¹¹ groups.

R³ is H;

R⁴, R⁵, and R⁶ are each H;

W is Br or Cy;

Cy is a phenyl ring, a piperazine ring, a pyridine ring, a pyrimidine ring, an imidazole ring, an indazole ring, or a 1H-pyrazolo[4,3-b]pyridine ring, each of which is optionally substituted by 1 or 2 substituents independently selected from halo, C_{1-6} alkyl, C_{1-6} haloalkyl, Cy¹, —(C_{1-2} alkylene)-Cy¹, CN, OR^a, P(O)R^aR^b, NR^cR^d, NR^cC(O)R^b, NR^cC(O)NR^cR^d, NR^cS(O)₂R^b, NR^cS(O)₂NR^cR^d, S(O)₂R^b, and S(O)₂NR^cR^d;

each R¹¹ is independently selected from halo, C_{1-6} alkyl, and C_{1-6} haloalkyl;

each R^a is independently selected from H and C_{1-6} alkyl; wherein said C_{1-6} alkyl is optionally substituted with 1, 2, 3, or 4 independently selected R^g groups;

each R^c and R^d is independently selected from H, C_{1-6} alkyl, and Cy¹; wherein said C_{1-6} alkyl is optionally substituted with 1, 2, 3, or 4 independently selected R^g groups;

each R^b is independently selected from C_{1-6} alkyl and Cy¹; wherein said C_{1-6} alkyl is optionally substituted with 1, 2, 3, or 4 independently selected R^g groups;

each Cy¹ is independently selected from phenyl and 6-membered heterocycloalkyl, each optionally substituted by 1 or 2 independently selected R^g groups; and each $R^g$ is, independently, OH, $C_{1-6}$ alkyl, $C_{1-4}$ haloalkyl, halo, or carboxy.

In some embodiments:

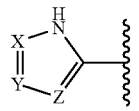

is:

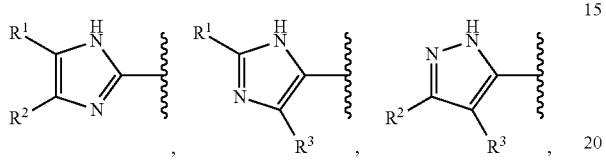

or

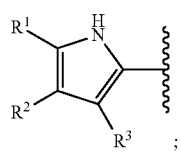

A is O, S, or CH=CH;

$R^1$ is H, ethyl, cyclopropyl, phenyl, or a tetrahydrofuran ring;

$R^2$ is H, methyl, or phenyl.

$R^1$ and $R^2$, together with the carbon atoms to which they are attached, form a phenyl ring, which is optionally substituted by 1 or 2 groups independently selected from F, Br, $CH_3$, and $CF_3$;

$R^3$ is H;

$R^4$, $R^5$, and $R^6$ are each H;

W is Br or Cy; and

Cy is a pyridine ring, which is optionally substituted by 1 or 2 groups independently selected from F, Cl, CN, —OH, —$OCH_3$, —$OCH(CH_3)_2$, —$OCHF_2$, —$N(CH_3)_2$, —$S(O)_2CH_3$, —$S(O)_2N(CH_3)_2$, —$NHC(O)CH_3$, ethylsulfonylamino, isopropylsulfonylamino, piperazinylsulfonylamino, morpholinylsulfonylamino, piperdinylsulfonylamino, phenylsulfonylamino, and (dimethylamino)sulfonylamino; wherein said phenylsulfonylamino is optionally substituted by F; and said piperazinylsulfonylamino is optionally substituted by $CH_3$.

In some embodiments:

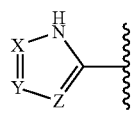

is:

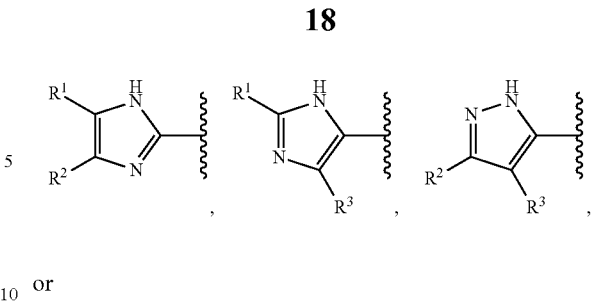

or

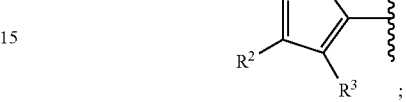

A is O, S, or CH=CH;

$R^1$ is H, methyl, ethyl, cyclopropyl, phenyl, or a tetrahydrofuran ring;

$R^2$ is H, methyl, propyl, or phenyl;

$R^1$ and $R^2$, together with the carbon atoms to which they are attached, form a phenyl ring or cyclohexene ring, which is optionally substituted by 1 or 2 groups independently selected from F, Br, $CH_3$, and $CF_3$;

$R^3$ is H;

$R^4$, $R^5$, and $R^6$ are each H;

W is Br or Cy; and

Cy is a phenyl ring, a piperazine ring, a pyridine ring, a pyrimidine ring, an imidazole ring, an indazole ring, or a 1H-pyrazolo[4,3-b]pyridine ring, each of which is optionally substituted by 1 or 2 groups independently selected from F, Cl, CN, —OH, —$OCH_3$, —$OCH(CH_3)_2$, —$OCHF_2$, —$NH_2$, —$N(CH_3)_2$, —$S(O)_2CH_3$, —$S(O)_2N(CH_3)_2$, —$NHC(O)CH_3$, —$CF_3$, dimethylphosphoryl, methyl, ethyl, benzyl, methylsulfonyl, ethylsulfonyl, pyrrolidinylsulfonyl, ethylsulfonylamino, ethylsulfonyl-N($CH_3$)—, isopropylsulfonylamino, piperazinylsulfonylamino, morpholinylsulfonylamino, piperdinylsulfonylamino, phenylsulfonylamino, and (dimethylamino)sulfonylamino; wherein said methyl, methylsulfonyl, pyrrolidinylsulfonyl, phenylsulfonylamino, piperazinylsulfonylamino are each optionally substituted by 1 or 2 groups independently selected from F, $CH_3$, OH, $CF_3$, and C(O)OH.

In any of the previous embodiments, the compound is a compound of Formula II:

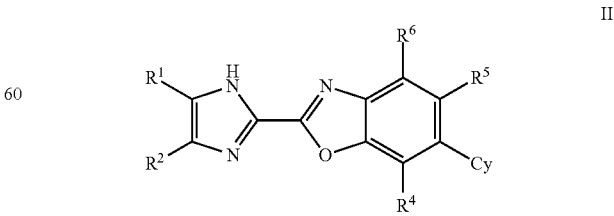

or a pharmaceutically acceptable salt thereof.

In any of the previous embodiments, the compound is a compound of Formula III:

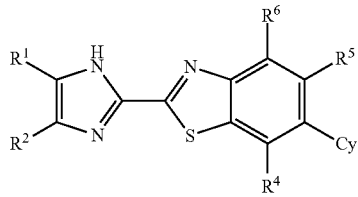

III or a pharmaceutically acceptable salt thereof.

In any of the previous embodiments, the compound is a compound of Formula IV:

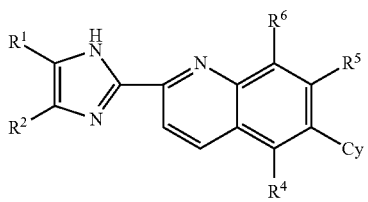

IV or a pharmaceutically acceptable salt thereof.

In any of the previous embodiments, the compound is a compound of Formula V:

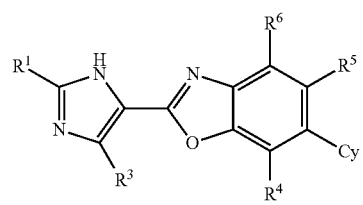

V or a pharmaceutically acceptable salt thereof.

In any of the previous embodiments, the compound is a compound of Formula VI:

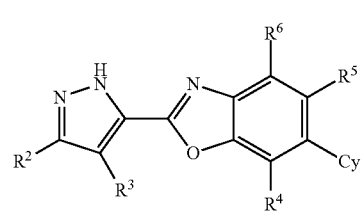

or a pharmaceutically acceptable salt thereof.

In any of the previous embodiments, the compound is a compound of Formula VII:

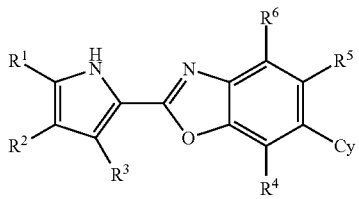

VII or a pharmaceutically acceptable salt thereof.

In any of the previous embodiments, the compound is a compound of Formula IIa, IIb, IIIa, IVa, or VIIa:

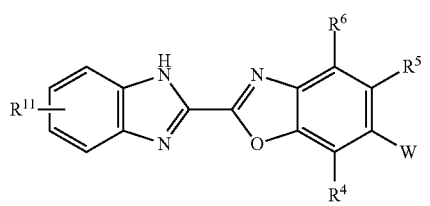

IIa

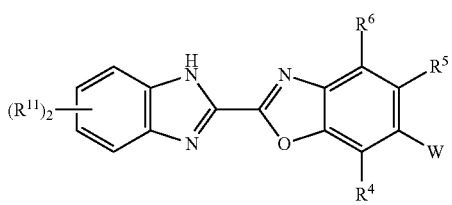

IIb

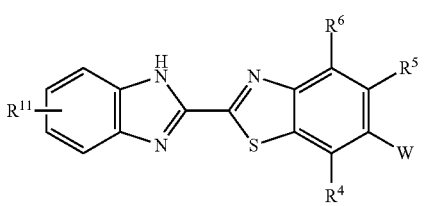

IIIa

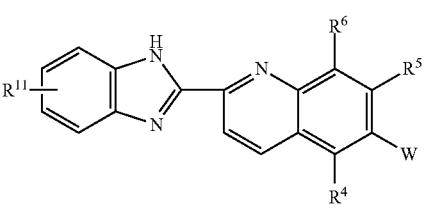

IVa

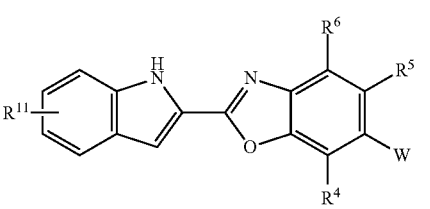

VIIa or a pharmaceutically acceptable salt thereof.

In any of the previous embodiments, the compound is a compound of Formula IIc, IId, IIe, IIIb, IIIc, IVb, IVc, VIIb, or VIIc,

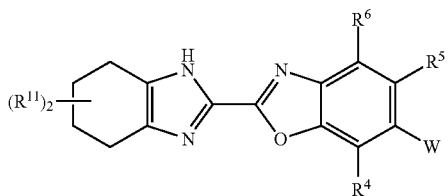
IIc

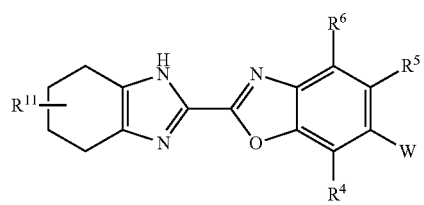
IId

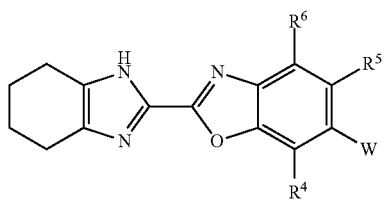
IIe

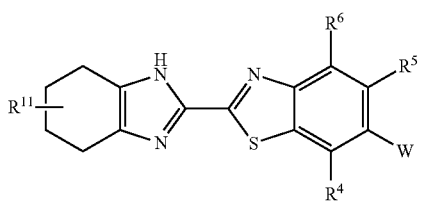
IIIb

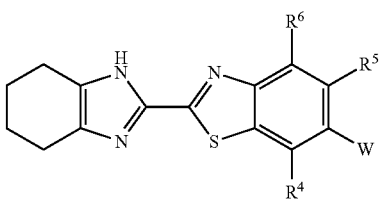
IIIc

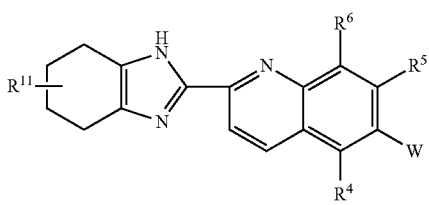
IVb

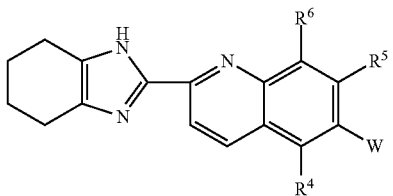
IVc

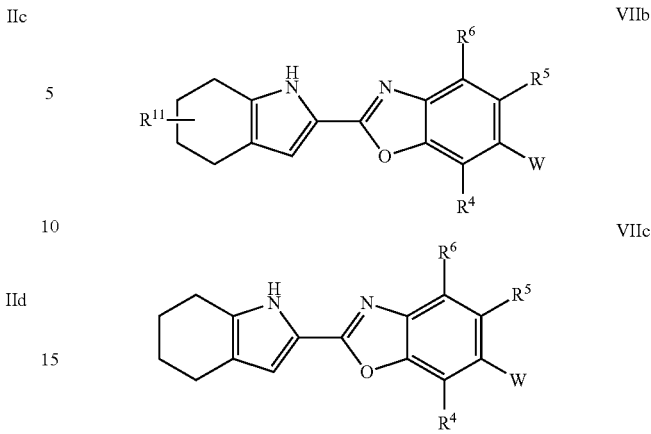
VIIb

VIIc or a pharmaceutically acceptable salt thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and iso-propoxy), butoxy (e.g., n-butoxy and tert-butoxy), and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms. Examples of alkoxycarbonyl groups include, but are not limited to, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms. Examples of alkylcarbonyl groups include, but are not limited to, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to 10 carbon atoms. In some embodiments, the aryl group is phenyl or naphthyl.

As used herein, the term "carbamyl" to a group of formula —C(O)NH$_2$.

As used herein, the term "carbonyl", employed alone or in combination with other terms, refers to a —C(=O)— group, which may also be written as C(O).

As used herein, the term "carboxy" refers to a —C(O)OH group.

As used herein, the term "cyano-$C_{1-3}$ alkyl" refers to a group of formula —($C_{1-3}$ alkylene)-CN.

As used herein, the term "HO—$C_{1-3}$ alkyl" refers to a group of formula —($C_{1-3}$ alkylene)-OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, "halo" refers to F, Cl, Br, or I. In some embodiments, a halo is F, Cl, or Br.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$). In some embodiments, the cycloalkyl is a $C_{3-10}$ monocyclic or bicyclic cyclocalkyl. In some embodiments, the cycloalkyl is a $C_{3-7}$ monocyclic cyclocalkyl. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, or cyclohexyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 monocyclic heteroaryl having 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, or S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom as a divalent substituent, forming a carbonyl group when attached to a carbon (e.g., C=O), or attached to a heteroatom forming a sulfoxide or sulfone group.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. In some embodiments, the compound has the (R)-configuration. In some embodiments, the compound has the (S)-configuration.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Synthesis

As will be appreciated, the compounds provided herein, including salts thereof, can be prepared using known organic synthesis techniques and can be synthesized according to any of numerous possible synthetic routes.

Compounds described herein, wherein W is Cy, can be prepared as shown in Scheme I. The intermediate (i), where $X^1$ is halo, can be coupled with (ii), where M is a boronic acid, boronic ester, or an appropriately substituted metal such as Sn(Bu)$_4$ or Zn, under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give an amino derivative (iii). M-W (ii) can also be an amine containing heterocycle (where M is H and is attached to the amine nitrogen of heterocycle W) with coupling to the halide of (i) being performed by heating with a base or under Buchwald/Hartwig conditions (e.g., in the presence of a palladium(0) catalyst, such as tetrakis(triphenylphosphine)palladium(0) and a base (e.g., an alkoxide base)) to give derivative (iii). The amino derivative can be coupled to either a heterocyclic aldehyde (iv) under standard conditions (e.g., Pb(OAc)$_2$) or to a trihalo heterocycle (v), (e.g., where $X^1$ is a halogen, such as F or Cl) to give compounds of Formula I. Alternatively, the $X^1$ amino group of (i) can be coupled to either a heterocyclic aldehyde (iv) under standard conditions (e.g., Pb(OAc)$_2$) or to a trihalo heterocycle (v), (e.g., where $X^1$ is a halogen, such as F or Cl) to give a bicycloheteroarl derivative (vi). The NH of the heterocycle (vi) can be optionally protected (e.g., SEM-Cl and base) to give a N-protected derivative (vii) which can be coupled with (ii), where M is a boronic acid, boronic ester, or an appropriately substituted metal such as Sn(Bu)$_4$ or Zn, under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), or where M-W (ii) can also be an amine containing heterocycle (where M is H and is attached to the amine nitrogen of heterocycle W) with coupling to the halide of (i) being performed by heating with a base or under Buchwald/Hartwig conditions (e.g., in the presence of a palladium(0) catalyst, such as tetrakis(triphenylphosphine)palladium(0) and a base (e.g., an alkoxide base)) can give a derivative (x) which can be deprotected to yield compounds of Formula I. Alternatively, conversion of the halide of intermediate (vii) to a metal M (e.g., M is B(OR)$_2$, SnR$_3$, Zn) under standard conditions can give intermediates (viii) which can undergo Suzuki, Stille or Negishi couplings with appropriate halo-derivatives W—$X^1$ (ix) can afford protected intermediates (x) or upon N-deprotection (e.g., reaction with a strong acid, such as TFA) compounds of Formula I.

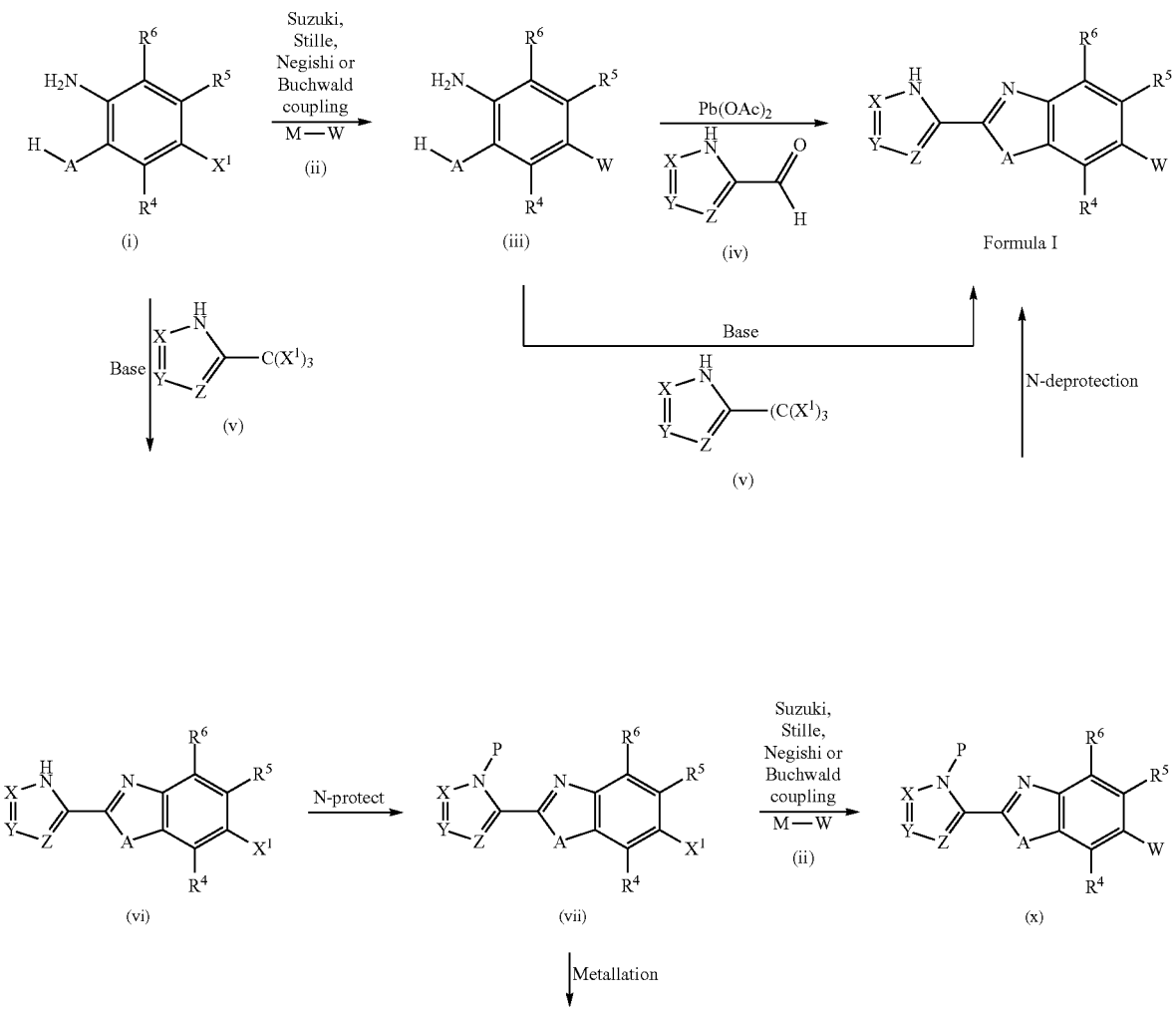

Scheme I

-continued

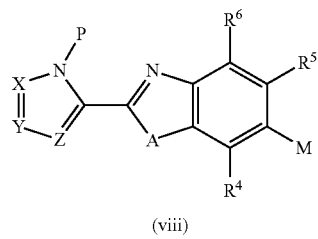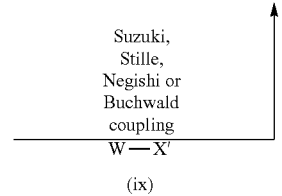

(viii)

(ix)

Compounds described herein, wherein W is Cy and Z is N, can be prepared as shown in Scheme II. The heterocycle (i), where $X^1$ is halo, can be coupled with (ii), where M is a boronic acid, boronic ester, or an appropriately substituted metal such as $Sn(Bu)_4$ or Zn, under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative (iii). M-W (ii) can also be an amine containing heterocycle (where M is H and is attached to the amine nitrogen of heterocycle W) with coupling to the halide of (i) being performed by heating with a base or under Buchwald/Hartwig conditions (e.g., in the presence of a palladium(0) catalyst, such as tetrakis(triphenylphosphine)palladium(0) and a base (e.g., an alkoxide base)) to give a derivative (iii). The heterocycle (iii) can be oxidized with suitable reagents, such as $SeO_2$, or reacted with 1,1-dimethoxy-N,N-dimethylmethanamine to give olefin which can be subsequently oxidized with a suitable reagent, such as $NaIO_4$, to give an aldehyde (iv). The aldehyde (iv) can be coupled with a suitable diamine (v) under standard conditions (e.g., $PhI(CF_3CO_2)_2$) to afford compounds of Formula I. Alternatively, heterocycle (i) can be oxidized with suitable reagents, such as $SeO_2$, or reacted with 1,1-dimethoxy-N,N-dimethylmethanamine to give olefin which can be subsequently oxidized with a suitable reagent, such as $NaIO_4$, to give an aldehyde (vi). The aldehyde (vi), where $X^1$ is halo, can be coupled with (ii), where M is a boronic acid, boronic ester, or an appropriately substituted metal such as $Sn(Bu)_4$ or Zn, under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative (vii). M-W (ii) can also be an amine containing heterocycle (where M is H and is attached to the amine nitrogen of heterocycle W) with coupling to the halide of (vi) being performed by heating with a base or under Buchwald/Hartwig conditions (e.g., in the presence of a palladium(0) catalyst, such as tetrakis(triphenylphosphine)palladium(0) and a base (e.g., an alkoxide base)) to give derivative (vii). The aldehyde (vii) can be coupled with a suitable diamine (v) under standard conditions (e.g., $PhI(CF_3CO_2)_2$) to afford compounds of Formula I.

Scheme II

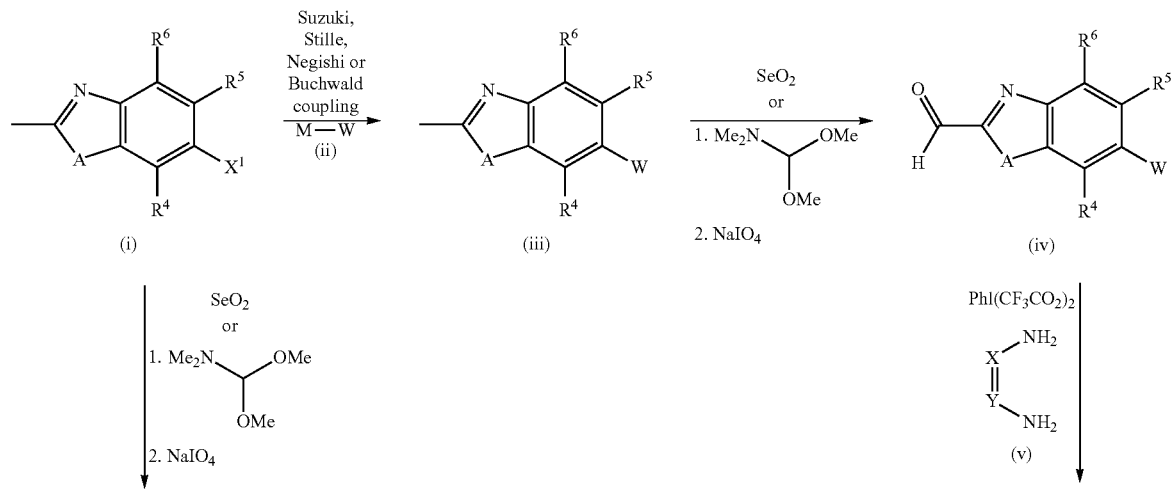

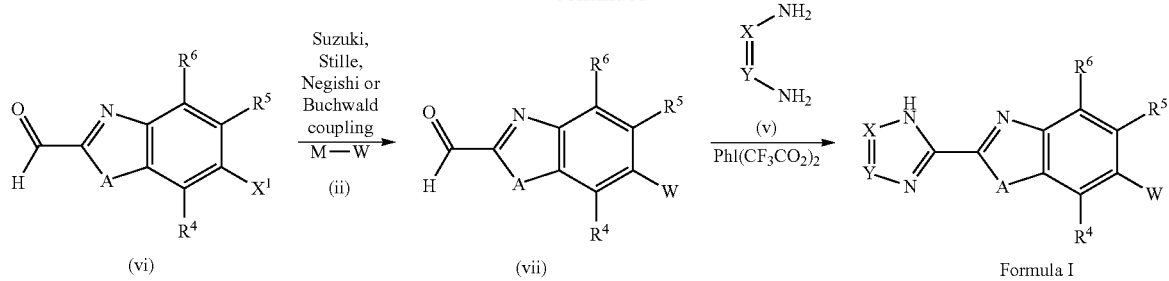

Compounds described herein, wherein W is substituted pyridin-3-yl, can be synthesized as shown in Scheme III. The halo intermediate (vii) of Scheme I can be coupled with an appropriate pyridylboronic acid using standard Suzuki reaction conditions to give an amino compound (i). Acylation, sulfonylation, alkylation, or arylation can be performed under standard conditions with appropriate reagents (e.g., R'—X, where X=halogen) to afford N-protected derivatives which upon deprotection give compounds of Formula I.

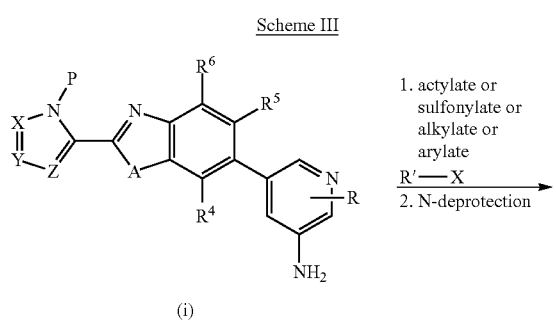

Intermediates for synthesizing compounds described herein, wherein Z in N, can be prepared as shown in Scheme IV. A diamine (i) can be coupled with an amidate (ii) NH=(OMe)C(X$^1$)$_3$ (where X$^1$=Br, Cl, or I) and a base, such as NaOH) to afford a trihalo heterocyclic intermediate (iii). Compounds of the invention can be synthesized from intermediates (iii) using the methods described in Scheme I.

Intermediates for synthesizing compounds described herein can be prepared as shown in Scheme V. A dibromide (i) can be coupled with an aldehyde (ii) and NaOAc/NH$_4$OH to afford a trihalo-imidazole intermediate (iii). A diketone (iv) can be coupled with hydrazine (v) to afford a trihalo-pyrazole intermediate (vi). An ester (vii) can be coupled with an amidine (viii) and to afford a trihalo-triazole intermediate (ix). Compounds of the invention can be synthesized from intermediates (iii, vi and ix) using the methods described in Scheme I.

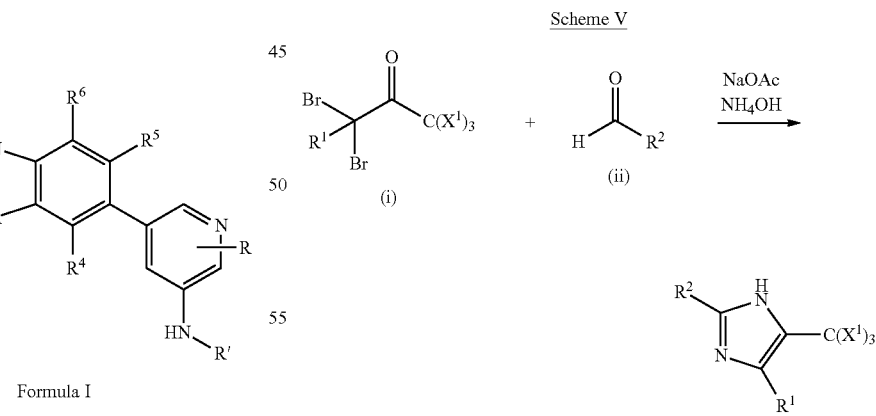

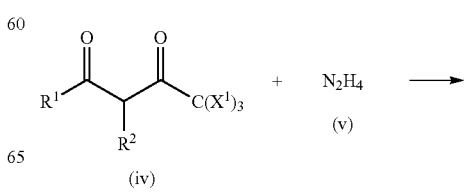

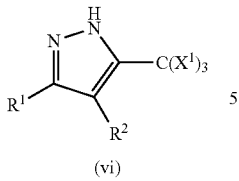

(vi)

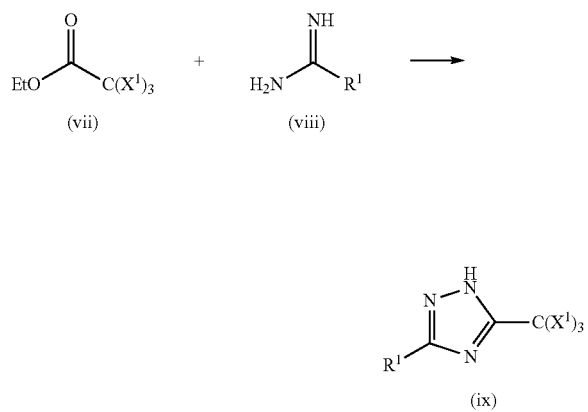

Compounds described herein, wherein Z is N, can be prepared as shown in Scheme VI. An aldehyde (i) from Scheme I can be oxidized under standard conditions (e.g., KMnO4) to its carboxylic acid (ii) and then coupled to an aminoketone (iii) using standard amide coupling agents (e.g., HBTU, HATU or EDC) to give an amide which can cyclize to an imidazole upon treatment with AcOH and NH4OAc to afford compounds of Formula I.

Scheme VI

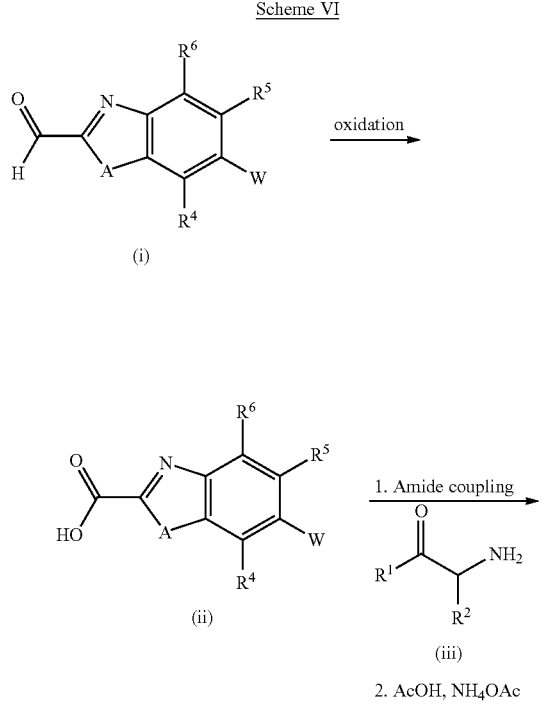

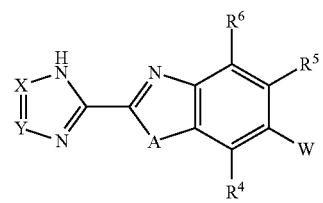

Formula I

Compounds described herein, wherein W is Cy and Z is N, can be prepared as shown in Scheme VII. The heterocycle (i), where $X^1$ is halo, can be coupled with (ii), where M is a boronic acid, boronic ester, or an appropriately substituted metal such as $Sn(Bu)_4$ or Zn, under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0)), to give a derivative (iii). M-W (ii) can also be an amine containing heterocycle (where M is H and is attached to the amine nitrogen of heterocycle W) with coupling to the halide of (i) being performed by heating with a base or under Buchwald/Hartwig conditions (e.g., in the presence of a palladium(0) catalyst, such as tetrakis(triphenylphosphine)palladium(0) and a base (e.g., an alkoxide base)) to give a derivative (iii). The heterocycle (iii) can be oxidized with suitable reagents, such as $SeO_2$, or reacted with 1,1-dimethoxy-N,N-dimethylmethanamine to give olefin which can be subsequently oxidized with a suitable reagent, such as $NaIO_4$, to give an aldehyde (iv). The aldehyde (iv) can be coupled with a suitable diketone (v) under standard conditions (e.g., NH4OAc in HOAc) to afford compounds of Formula I. Alternatively, heterocycle (i) can be oxidized with suitable reagents, such as $SeO_2$, or reacted with 1,1-dimethoxy-N,N-dimethylmethanamine to give olefin which can be subsequently oxidized with a suitable reagent, such as $NaIO_4$, to give an aldehyde (vi). The aldehyde (vi), where $X^1$ is halo, can be coupled with a suitable diketone (v) under standard conditions (e.g., NH4OAc in HOAc) to afford heterocycle (vii). The heterocycle (vii) can be coupled with (ii), where M is a boronic acid, boronic ester, or an appropriately substituted metal such as $Sn(Bu)_4$ or Zn, under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0)), to afford compounds of Formula I. M-W (ii) can also be an amine containing heterocycle (where M is H and is attached to the amine nitrogen of heterocycle W) with coupling to the halide of (vi) being performed by heating with a base or under Buchwald/Hartwig conditions (e.g., in the presence of a palladium(0) catalyst, such as tetrakis(triphenylphosphine)palladium(0) and a base (e.g., an alkoxide base)) to afford compounds of Formula I.

Scheme VII

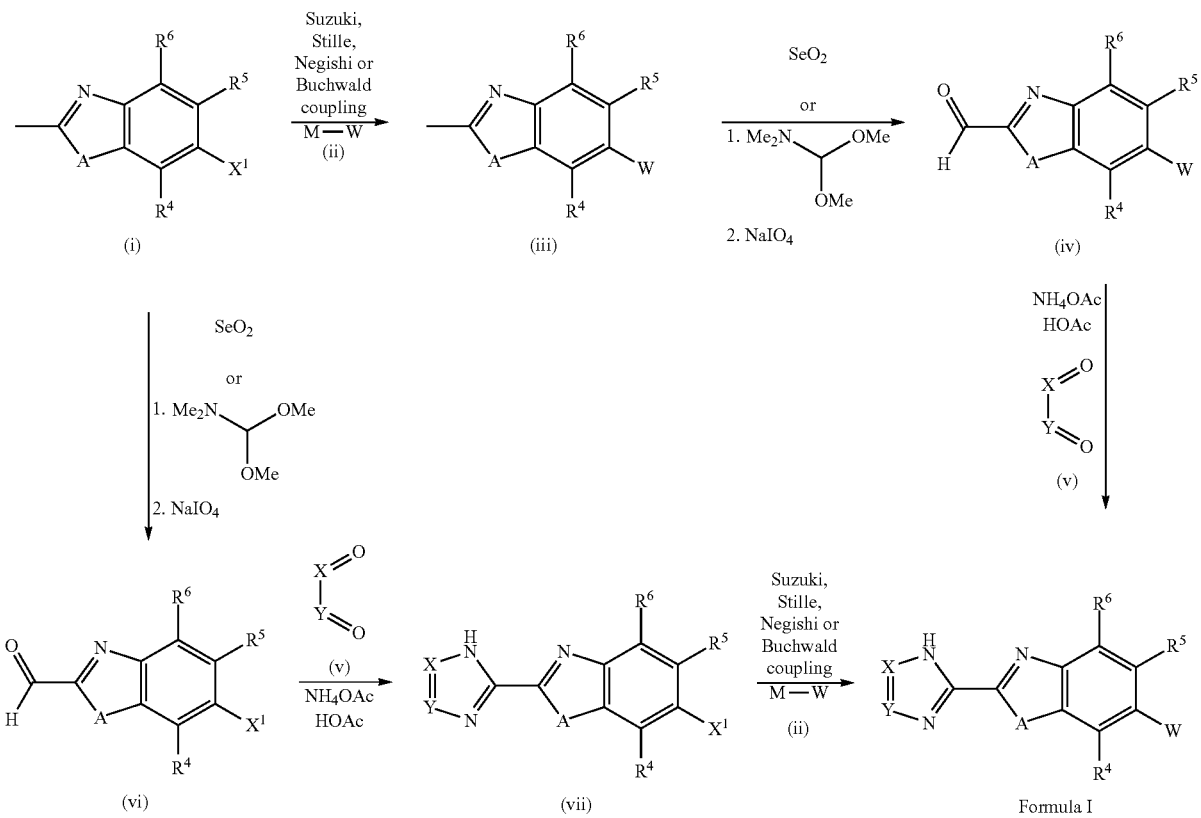

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Methods of Use

The compounds or salts described herein inhibit activity of PI3Kγ kinase. Accordingly, the compounds or salts described herein can be used in methods of inhibiting PI3Kγ kinase by contacting the kinase with any one or more of the compounds, salts, or compositions described herein. In some embodiments, the compounds or salts can be used in methods of inhibiting activity of PI3Kγ in an individual in need of said inhibition by administering a inhibiting amount of a compound or salt of described herein. In some embodiments, modulating is inhibiting. In some embodiments, the contacting is in vivo. In some embodiments, the contacting is ex vivo.

In some embodiments, the PI3Kγ includes a mutation. A mutation can be a replacement of one amino acid for another, or a deletion of one or more amino acids. In such embodiments, the mutation can be present in the kinase domain of the PI3Kγ.

In some embodiments, the compound or salt further inhibits PI3KΛ.

The compounds or salts described herein can be selective. By "selective" is meant that the compound binds to or inhibits PI3Kγ with greater affinity or potency, respectively, compared to at least one other kinase. In some embodiments, the compounds of the invention are selective inhibitors of PI3Kγ over PI3Kδ, PI3Kα, and PI3Kβ. In some embodiments, the compounds of the invention are selective inhibitors of PI3Kγ over PI3Kα and PI3Kβ. In some embodiments, selectivity can be at least about 2-fold, 3-fold, 5-fold, 10-fold, at or 20-fold over PI3Kδ as measured by the assays described herein. In some embodiments, selectivity can be tested at the $K_m$ ATP concentration of each enzyme. In some embodiments, the selectivity of compounds of the invention can be determined by cellular assays associated with particular PI3K kinase activity.

Another aspect of the present invention pertains to methods of treating a kinase PI3Kγ-associated disease or disorder in an individual (e.g., patient) by administering to the individual in need of such treatment a therapeutically effective amount or dose of one or more compounds of the present invention or a pharmaceutical composition thereof. A PI3Kγ-associated disease or disorder can include any disease, disorder or condition that is directly or indirectly linked to expression or activity of the PI3Kγ, including overexpression and/or abnormal activity levels.

In some embodiments, the disease or disorder is an autoimmune disease or disorder, cancer, cardiovascular disease, or neurodegenerative disease.

In some embodiments, the disease or disorder is lung cancer (e.g., non-small cell lung cancer), melanoma, pancreatic cancer, breast cancer, prostate cancer, liver cancer, color cancer, endometrial cancer, bladder cancer, skin cancer, cancer of the uterus, renal cancer, gastric cancer, or sarcoma. In some embodiments, the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

In some embodiments, the disease or disorder is acute myeloid leukemia (e.g., acute monocytic leukemia), small lymphocytic lymphoma, chronic lymphocytic leukemia (CLL), chronic myelogenous leukemia (CML), multiple myeloma, T-cell actute lymphoblasic leukemia (T-ALL), cutaneous T-cell lymphoma, large granular lymphocytic leukemia, mature (peripheral) t-cell neoplasm (PTCL), anaplastic large cell lymphoma (ALCL), or lymphoblastic lymphoma. In some embodiments, the mature (peripheral) t-cell neoplasm (PTCL) is T-cell prolymphocytic leukemia, T-cell granular lymphocytic leukemia, aggressive NK-cell leukemia, mycosis fungoides/Sezary syndrome, naplastic large cell lymphoma (T-cell type), enteropathy type T-cell lymphoma, adult T-cell leukemia/lymphoma, or angioimmunoblastic T-cell lymphoma In some embodiments, the anaplastic large cell lymphoma (ALCL) is systemic ALCL or primary cutaneous ALCL.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

In some embodiments, the non-Hodgkin's lymphoma (NHL) is relapsed NHL, refractory NHL, recucurrent follicular NHL, indolent NHL (iNHL), or aggressive NHL (aNHL).

In some embodiments, the diffuse large B cell lymphoma is activated B-cell like (ABC) diffuse large B cell lymphoma, or germinal center B cell (GCB) diffuse large B cell lymphoma.

In some embodiments, the Burkitt's lymphoma is endemic Burkitt's lymphoma, sporadic Burkitt's lymphoma, or Burkitt's-like lymphoma In some embodiments, the disease or disorder is rheumatoid arthritis, multiple sclerosis, systemic lupus erythematous, asthma, allergy, pancreatitis, psoriasis, anaphylaxis, glomerulonephritis, inflammatory bowel disease (e.g., Crohn's disease and ulcerative colitis), thrombosis, meningitis, encephalitis, diabetic retinopathy, benign prostatic hypertrophy, myasthenia gravis, Sjögren's syndrome, osteoarthritis, restenosis, or atherosclerosis.

In some embodiments, disease or disorder is heart hypertropy, cardiac myocyte dysfunction, chronic obstructive pulmonary disease (COPD), elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft rejection, glomerulosclerosis, progressive renal fibrosis, idiopathic thrombocytopenic purpura (ITP), autoimmune hemolytic anemia, vasculitis, systemic lupus erythematosus, lupus nephritis, pemphigus, or membranous nephropathy.

In some embodiments, the disease or disorder is Alzheimer's disease, central nervous system trauma, or stroke.

In some embodiments, the idiopathic thrombocytopenic purpura (ITP) is relapsed ITP or refractory ITP.

In some embodiments, the vasculitis is Behçet's disease, Cogan's syndrome, giant cell arteritis, polymyalgia rheumatica (PMR), Takayasu's arteritis, Buerger's disease (thromboangiitis obliterans), central nervous system vasculitis, Kawasaki disease, polyarteritis nodosa, Churg-Strauss syndrome, mixed cryoglobulinemia vasculitis (essential or hepatitis C virus (HCV)-induced), Henoch-Schönlein purpura (HSP), hypersensitivity vasculitis, microscopic polyangiitis, Wegener's granulomatosis, or anti-neutrophil cytoplasm antibody associated (ANCA) systemic vasculitis (AASV).

The present invention further provides a compound described herein, or a pharmaceutically acceptable salt thereof, for use in any of the methods described herein.

The present invention further provides use of a compound described herein, or a pharmaceutically acceptable salt thereof, for the preparation of a medicament for use in any of the methods described herein.

As used herein, the term "contacting" refers to the bringing together of indicated moieties in an in vitro system or an in vivo system. For example, "contacting" a PI3K with a compound of the invention includes the administration of a compound of the present invention to an individual or patient, such as a human, having a PI3K, as well as, for example, introducing a compound of the invention into a sample containing a cellular or purified preparation containing the PI3K.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" can refer to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as Bcr-Abl, Flt-3, EGFR, HER2, JAK, c-MET, VEGFR, PDGFR, cKit, IGF-1R, RAF and FAK kinase inhibitors such as, for example, those described in WO 2006/056399. Other agents such as therapeutic antibodies can be used in combination with the compounds of the present invention for treatment of PI3K-associated diseases, disorders or conditions. The one or more additional pharmaceutical agents can be administered to a patient simultaneously or sequentially.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present invention and are presented as a non limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevecu, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the invention can be used in combination with one or more other kinase inhibitors including imatinib, particularly for treating patients resistant to imatinib or other kinase inhibitors.

In some embodiments, the compounds of the invention can be used in combination with a chemotherapeutic in the treatment of cancer, and may improve the treatment response as compared to the response to the chemotherapeutic agent alone, without exacerbation of its toxic effects. In some embodiments, the compounds of the invention can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a PI3K inhibitor of the present invention with an additional agent.

In some embodiments, the compounds of the invention can be used in combination with a targeted agent provided herein.

In some embodiments, the compounds of the invention can be used in combination with one or more immune-oncology agents. In some embodiments, the immune-oncology agent is selected from the group consisting of CTLA4, PD1, and PDL biologics.

In some embodiments, the compounds of the invention can be used in combination with one or more metabolic enzyme inhibitors. In some embodiments, the metabolic enzyme inhibitor is an inhibitor of IDO1, TDO, or arginase.

The agents can be combined with the present compound in a single or continuous dosage form, or the agents can be administered simultaneously or sequentially as separate dosage forms.

In some embodiments, a corticosteroid such as dexamethasone is administered to a patient in combination with the compounds of the invention where the dexamethasone is administered intermittently as opposed to continuously.

In some further embodiments, combinations of the compounds of the invention with other therapeutic agents can be administered to a patient prior to, during, and/or after a bone marrow transplant or stem cell transplant.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the invention contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the invention contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the invention.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed herein.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Accordingly, the present invention includes PI3K assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}$H (also written as D for deuterium), $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro PI3K labeling and competition assays, compounds that incorporate $^{3}$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^{3}$H, $^{14}$C, $^{125}$I, $^{35}$S and $^{82}$Br.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of PI3K-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. The compounds of the Examples have been found to be PI3Kγ inhibitors according to at least one assay described herein.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Hague, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 μm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, J. Comb. Chem., 6, 874-883 (2004)). Typically, the flow rate used with the 30×100 mm column was 60 mL/minute.

pH=10 purifications: Waters XBridge $C_{18}$ 5 μm, 19×100 mm column, eluting with mobile phase A: 0.15% NH$_4$OH in water and mobile phase B: acetonitrile; the flow rate was 30 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, J. Comb. Chem., 6, 874-883 (2004)). Typically, the flow rate used with 30×100 mm column was 60 mL/minute.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

2-(1H-Imidazol-2-yl)-6-(5-methoxypyridin-3-yl)benzo[d]oxazole trifluoroacetate

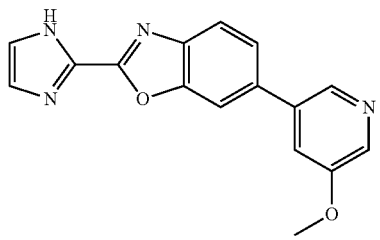 [SMILES: COc1cncc(-c2ccc3nc(-c4ncc[nH]4)oc3c2)c1]

Step 1. 2-Amino-5-(5-methoxypyridin-3-yl)phenol

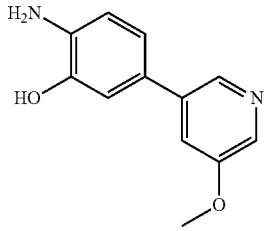 [SMILES: COc1cncc(-c2ccc(N)c(O)c2)c1]

A 1-dram vial was charged with 2-amino-5-bromophenol [Combi-Blocks, SS-6172] (0.13 g, 0.71 mmol), 3-methoxy-5-(4,4,5,5-tetramethyl-1,3,2-dioxaborolan-2-yl)pyridine [Aldrich, 636029] (0.2 g, 0.8 mmol), and 1,4-dioxane (8 mL). Cesium fluoride (300 mg, 2 mmol) in water (2 mL) was added, and the solution was degassed with $N_2$ for 5 min. 4-(Di-tert-butylphosphino)-N,N-dimethylaniline-dichloropalladium (2:1) (200 mg, 0.2 mmol) was added, and the solution was degassed for an additional 5 min. The reaction mixture was heated at 90° C. for 2 h. The reaction mixture was cooled to room temperature, diluted with dichloromethane (50 mL), and filtered through diatomaceous earth. The filtrate was acidified with 1 N HCl (2×10 mL), the aqueous layer was washed neutralized with 1 M NaOH (20 mL) and extracted with dichloromethane (2×30 mL). The organic layers were combined, washed with brine (10 mL), dried over sodium sulfate, filtered and concentrated under reduced pressure. The brown residue (0.13 g) was directly used in the next step without further purification. LCMS calculated for $C_{12}H_{13}N_2O_2$ $(M+H)^+$: m/z=217.1. found: 217.1.

Step 2. 2-(1H-Imidazol-2-yl)-6-(5-methoxypyridin-3-yl)benzo[d]oxazole trifluoroacetate A 1-dram vial was charged with imidazole-2-carboxaldehyde [Matrix, 037577] (0.012 g, 0.13 mmol) and 2-amino-5-(5-methoxypyridin-3-yl)phenol (0.025 g, 0.12 mmol) in ethanol (2 mL, 30 mmol). The solution was stirred at 90° C. for 2 h. After cooling to room temperature the ethanol was evaporated with $N_2$ and the resultant residue was dissolved in dimethyl sulfoxide (2 mL) and lead tetraacetate (0.062 g, 0.14 mmol) was added. After stirring at room temperature for 1 h, the resulting mixture was diluted with dichloromethane (15 mL), washed with brine (10 mL), and concentrated via under reduced pressure. The crude product was purified by prep HPLC on a C-18 column eluting with a water:acetonitrile gradient buffered at pH 2 with 0.1% trifluoroacetic acid, to afford the title compound as a light brown amorphous solid (0.016 mg, 47%). LCMS calculated for $C_{16}H_{13}N_4O_2$ $(M+H)^+$: m/z=293.3. found: 293.3 $^1$H NMR (400 MHz, MeOD) δ 8.75 (d, J=1.4 Hz, 3H), 8.51 (d, J=2.5 Hz, 1H), 8.31-8.25 (m, 1H), 8.21 (d, J=1.3 Hz, 1H), 7.99 (d, J=8.4 Hz, 1H), 7.89 (dd, J=8.4, 1.7 Hz, 1H), 7.58 (s, 2H), 4.10 (s, 3H).

Example 2

2-(1H-Imidazol-5-yl)-6-(5-methoxypyridin-3-yl)benzo[d]oxazole trifluoroacetate

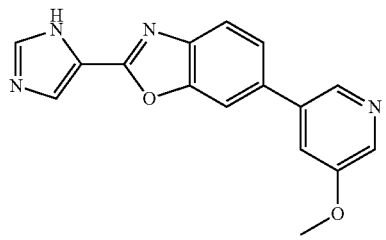 [SMILES: COc1cncc(-c2ccc3nc(-c4cnc[nH]4)oc3c2)c1]

This compound was synthesized according to the procedure of Example 1, substituting 1H-imidazole-5-carbaldehyde [Aldrich, 456128] for imidazole-2-carboxaldehyde. LCMS calculated for $C_{16}H_{13}N_4O_2$ $(M+H)^+$: m/z=293.3. found: 293.3 $^1$H NMR (400 MHz, MeOD) δ 8.73 (s, 1H), 8.56-8.41 (m, 2H), 8.24 (d, J=14.8 Hz, 2H), 8.15 (d, J=1.2 Hz, 1H), 7.91 (d, J=8.3 Hz, 1H), 7.84 (dd, J=8.3, 1.6 Hz, 1H), 4.10 (s, 3H).

Example 3

6-(5-Methoxypyridin-3-yl)-2-(1H-pyrrol-2-yl)benzo[d]oxazole trifluoroacetate

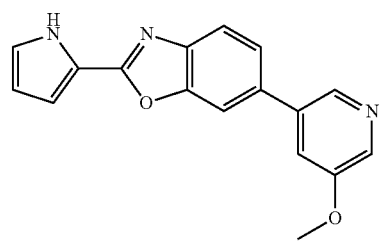 [SMILES: COc1cncc(-c2ccc3nc(-c4ccc[nH]4)oc3c2)c1]

This compound was synthesized according to the procedure of Example 1, substituting 1H-pyrrole-2-carbaldehyde [Aldrich, P73404] for imidazole-2-carboxaldehyde. LCMS calculated for $C_{17}H_{14}N_3O_2$ $(M+H)^+$: m/z=292.1. found: 292.2 $^1$H NMR (400 MHz, MeOD) δ 8.76 (d, J=1.6 Hz, 1H), 8.51 (d, J=2.6 Hz, 1H), 8.41-8.28 (m, 1H), 8.05 (t, J=1.1 Hz, 1H), 7.78 (d, J=1.1 Hz, 2H), 7.17-7.06 (m, 2H), 6.36 (dd, J=3.7, 2.6 Hz, 1H), 4.11 (s, 3H).

Example 4

2-(1H-Benzo[d]imidazol-2-yl)-6-(5-methoxypyridin-3-yl)benzo[d]oxazole trifluoroacetate

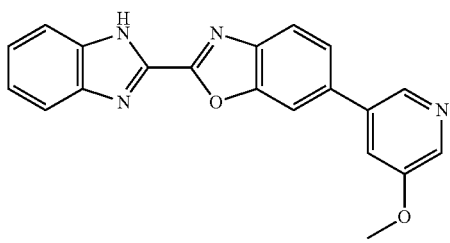 [SMILES: COc1cncc(-c2ccc3nc(-c4nc5ccccc5[nH]4)oc3c2)c1]

This compound was synthesized according to the procedure of Example 1, substituting 1H-benzo[d]imidazole-2-carbaldehyde [Ark Pharm, AK-25780] for imidazole-2-carboxaldehyde. LCMS calculated for $C_{20}H_{15}N_4O_2$ (M+H)$^+$: m/z=343.1. found: 343.1 $^1$H NMR (400 MHz, MeOD) δ 8.51 (d, J=1.8 Hz, 1H), 8.28 (d, J=2.7 Hz, 1H), 8.13 (d, J=1.4 Hz, 1H), 7.97 (d, J=8.3 Hz, 1H), 7.82 (dd, J=8.4, 1.6 Hz, 1H), 7.79-7.69 (m, 3H), 7.41 (dq, J=7.0, 3.9 Hz, 2H), 3.99 (s, 3H).

Example 5

2-(1H-Indol-2-yl)-6-(5-methoxypyridin-3-yl)benzo[d]oxazole trifluoroacetate

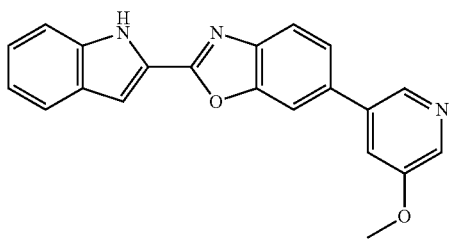 [SMILES: COc1cncc(-c2ccc3nc(-c4cc5ccccc5[nH]4)oc3c2)c1]

Step 1. 1H-Indole-2-carbaldehyde

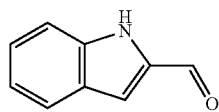 [SMILES: O=Cc1cc2ccccc2[nH]1]

A 10 mL vial was charged with 1H-indol-2-ylmethanol [Aldrich, 687226] (0.119 g, 0.810 mmol) and manganese (IV) oxide (0.2 g, 2 mmol) in dichloromethane (5 mL) and the mixture was stirred at room temperature overnight. The reaction mixture was filtered through diatomaceous earth. The filtrate was concentrated under reduced pressure to afford the crude product, which was taken to the following step without purification. LCMS calculated for $C_9H_8NO$ (M+H)$^+$: m/z=146.1. found: 146.1.

Step 2. 2-(1H-Indol-2-yl)-6-(5-methoxypyridin-3-yl)benzo[d]oxazole trifluoroacetate This compound was synthesized according to the procedure of Example 1, substituting 1H-indole-2-carbaldehyde for imidazole-2-carboxaldehyde. LCMS calculated for $C_{21}H_{16}N_3O_2$ (M+H)$^+$: m/z=342.1. found: 342.1 $^1$H NMR (400 MHz, MeOD) δ 8.69 (s, 1H), 8.43 (d, J=2.5 Hz, 1H), 8.20-8.14 (m, 1H), 8.10 (d, J=1.4 Hz, 1H), 7.87 (d, J=8.3 Hz, 1H), 7.80 (dd, J=8.3, 1.7 Hz, 1H), 7.69 (d, J=8.1 Hz, 1H), 7.52 (d, J=9.0 Hz, 1H), 7.40 (s, 1H), 7.33-7.26 (m, 1H), 7.16-7.09 (m, 1H), 4.07 (s, 3H).

Example 6

2-(1H-Benzo[d]imidazol-2-yl)-6-(5-methoxypyridin-3-yl)benzo[d]thiazole trifluoroacetate

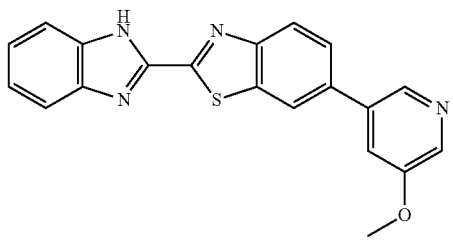

Step 1.
6-(5-Methoxypyridin-3-yl)-2-methylbenzo[d]thiazole

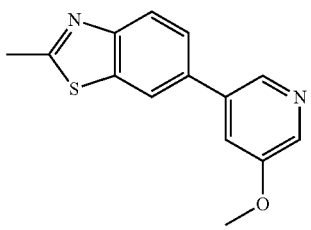

A 1-dram vial was charged with 6-bromo-2-methyl-1,3-benzothiazole [Aldrich, 756652] (0.081 g, 0.35 mmol), 3-methoxy-5-(4,4,5,5-tetramethyl-1,3,2-dioxaborolan-2-yl)pyridine (0.1 g, 0.4 mmol), and 1,4-dioxane (4 mL). Cesium fluoride (200 mg, 1 mmol) in water (1 mL) was added, and the solution was degassed with N$_2$ for 5 min. 4-(Di-tert-butylphosphino)-N,N-dimethylaniline-dichloropalladium (2:1) (38 mg, 0.053 mmol) was added, and the solution was degassed for an additional 5 min. The resulting mixture was heated at 90° C. for 2 h. The reaction mixture was cooled to room temperature, diluted with dichloromethane (25 mL), dried over sodium sulfate, and filtered through diatomaceous earth. The filtrate was concentrated under reduced pressure. The brown residue was purified by FCC on silica gel eluting with a hexane:ethyl acetate gradient to afford 6-(5-methoxypyridin-3-yl)-2-methylbenzo[d]thiazole (0.08 g, 90%). LCMS calculated for $C_{14}H_{13}N_2OS$, (M+H)$^+$: m/z=257.1. found: 257.1.

Step 2. 6-(5-Methoxypyridin-3-yl)benzo[d]thiazole-2-carbaldehyde

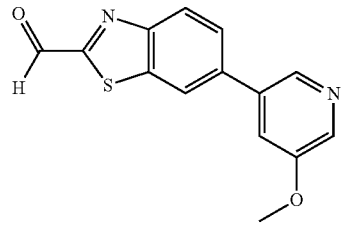

A 6 mL vial was charged with 6-(5-methoxypyridin-3-yl)-2-methyl-1,3-benzothiazole (0.040 g, 0.16 mmol) in 1,4-dioxane (2 mL). To the solution was added selenium dioxide (0.052 g, 0.47 mmol). The resulting suspension was stirred at 100° C. for 6 h. The reaction mixture was cooled to room temperature, diluted with dichloromethane (30 mL) and filtered through diatomaceous earth. The filtrate was concentrated via rotovap to afford the crude product, which was taken to the next step without purification. LCMS calculated for $C_{14}H_{11}N_2O_2S$ (M+H)$^+$: m/z=271.1. found: 271.1.

Step 3. 2-(1H-Benzo[d]imidazol-2-yl)-6-(5-methoxypyridin-3-yl)benzo[d]thiazole trifluoroacetate To a solution of 1,2-benzenediamine (0.021 g, 0.19 mmol) and 6-(5-methoxypyridin-3-yl)-1,3-benzothiazole-2-carbaldehyde (0.04 g, 0.2 mmol) in 1,4-dioxane (0.5 mL) was added [I,I-bis(trifluoroacetoxy)iodo]benzene (0.07 g, 0.2 mmol). The resultant mixture was stirred at room temperature for 15 min. The solvent was evaporated by $N_2$. The resulting residue was purified by prep HPLC on a C-18 column eluting with water:acetonitrile gradient buffered at pH 2 with 0.1% trifluoroacetic acid, to afford the title compound as a white solid (22 mg, 40%). LCMS calculated for $C_{20}H_{15}N_4OS$ (M+H)$^-$: m/z=359.1. found: 359.0 $^1$H NMR (400 MHz, MeOD) δ 8.75 (d, J=1.7 Hz, 1H), 8.56 (d, J=1.6 Hz, 1H), 8.48 (d, J=2.6 Hz, 1H), 8.29 (d, J=8.6 Hz, 1H), 8.27-8.23 (m, 1H), 7.99 (dd, J=8.6, 1.9 Hz, 1H), 7.72 (dd, J=6.2, 3.2 Hz, 2H), 7.39 (dd, J=6.2, 3.1 Hz, 2H), 4.10 (s, 3H).

Example 7

2-(1H-Benzo[d]imidazol-2-yl)-6-(5-methoxypyridin-3-yl)quinoline

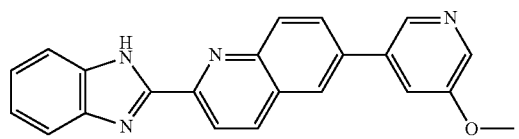 [SMILES: COc1cncc(-c2ccc3nc(-c4nc5ccccc5[nH]4)ccc3c2)c1]

Step 1. 6-(5-Methoxypyridin-3-yl)-2-methylquinoline

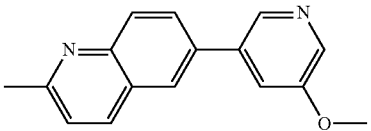

A 6 mL vial was charged with 6-bromo-2-methylquinoline [Aldrich, 649279] (0.079 g, 0.35 mmol), 3-methoxy-5-(4,4,5,5-tetramethyl-1,3,2-dioxaborolan-2-yl)pyridine (0.1 g, 0.4 mmol) and 1,4-dioxane (4 mL). Cesium fluoride (200 mg, 1 mmol) in water (1 mL) was added, and the solution was degassed with $N_2$ for 5 min. 4-(Di-tert-butylphosphino)-N,N-dimethylaniline-dichloropalladium (2:1) (38 mg, 0.053 mmol) was added, and the solution was further degassed for 5 min. The resultant mixture was heated at 90° C. for 2 h. The reaction mixture was cooled to room temperature, diluted with dichloromethane (25 mL), and filtered through diatomaceous earth. The filtrate was concentrated under reduced pressure. The brown residue was purified by FCC on silica gel eluting with a hexane:ethyl acetate gradient to afford 6-(5-methoxypyridin-3-yl)-2-methylquinoline (0.07 g, 80%). LCMS calculated for $C_{16}H_{15}N_2O$, (M+H)$^+$: m/z=251.1. found: 251.1.

Step 2. 6-(5-Methoxypyridin-3-yl)quinoline-2-carbaldehyde

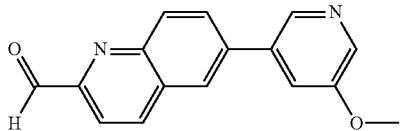 [SMILES: COc1cncc(-c2ccc3nc(C=O)ccc3c2)c1]

A 6 mL vial was charged with 6-(5-methoxypyridin-3-yl)-2-methylquinoline (0.05 g, 0.2 mmol) in 1,4-dioxane (2 mL). To the solution was added selenium dioxide (0.07 g, 0.6 mmol). The resulting suspension was stirred at 100° C. for 6 h. The reaction mixture was cooled to room temperature, diluted with dichloromethane (30 mL) and filtered through diatomaceous earth. The filtrate was concentrated under reduced pressure to afford the crude product, which was taken to the next step without purification. LCMS calculated for $C_{16}H_{13}N_2O_2$ (M+H)$^+$: m/z=265.1. found: 265.1.

Step 3. 2-(1H-Benzo[d]imidazol-2-yl)-6-(5-methoxypyridin-3-yl)quinoline

The title compound was synthesized according to an experimental procedure analogous to Example 6, Step 2, substituting 6-(5-methoxypyridin-3-yl)quinoline-2-carbaldehyde for 6-(5-methoxypyridin-3-yl)benzo[d]thiazole-2-carbaldehyde. LCMS calculated for $C_{22}H_{17}N_4O$ (M+H)$^-$: m/z=353.1. found: 353.2.

Example 8

2-(6-Bromo-1H-benzo[d]imidazol-2-yl)-6-(5-methoxypyridin-3-yl)benzo[d]oxazole

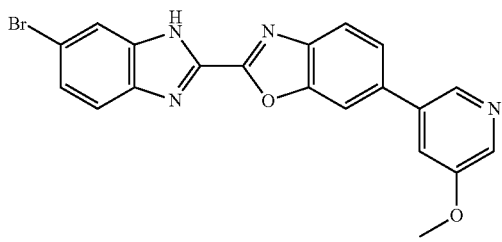 [SMILES: COc1cncc(-c2ccc3nc(-c4nc5ccc(Br)cc5[nH]4)oc3c2)c1]

Step 1. 6-(5-Methoxypyridin-3-yl)-2-methylbenzo[d]oxazole

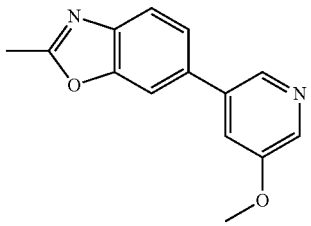 [SMILES: COc1cncc(-c2ccc3nc(C)oc3c2)c1]

To a solution of 2-amino-5-(5-methoxypyridin-3-yl)phenol (0.06 g, 0.3 mmol), pyridine (0.04 mL, 0.6 mmol), ytterbium(III) triflate (0.02 g, 0.03 mmol), in dimethyl sulfoxide (3 mL) was added trimethylorthoacetate (0.1 mL, 0.8 mmol). The resultant mixture was heated to 100° C. for 3 h. After the reaction mixture was cooled to room temperature, water (10 mL) and ethyl acetate (20 mL) was added. The organic layers were separated. The aqueous layer was extracted with ethyl acetate (2×10 mL). The organic layers were combined, dried over sodium sulfate, filtered, and concentrated via rotovap. The crude residue was purified with FCC to afford 6-(5-methoxypyridin-3-yl)-2-methylbenzo[d]oxazole (0.04 g, 60%). LCMS for $C_{14}H_{13}O_2N_2$ $(M+H)^+$: calculated m/z=241.1. found 241.1.

Step 2. (E)-2-(6-(5-Methoxypyridin-3-yl)benzo[d]oxazol-2-yl)-N,N-dimethylethenamine

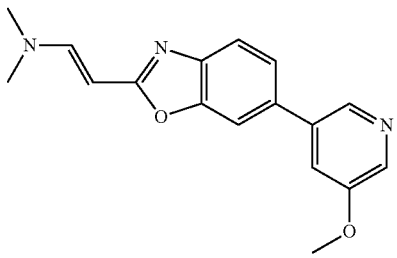 [SMILES: COc1cncc(-c2ccc3nc(/C=C/N(C)C)oc3c2)c1]

1.0 M Lithium methanolate in methanol (0.25 mL, 0.25 mmol) was added to a solution of 6-(5-methoxypyridin-3-yl)-2-methylbenzo[d]oxazole (400 mg, 2 mmol) in N,N-dimethylformamide (4 mL). The resultant mixture was heated to 100° C. for 0.5 h. To the mixture was added 1,1-dimethoxy-N,N-dimethylmethanamine (1.77 mL, 13.3 mmol) over 10 min. The reaction mixture was stirred at 95° C. overnight. The reaction mixture was then cooled to room temperature and water (100 mL) was added. The precipitate was collected by vacuum filtration, washed with water (3×100 mL), and dried in the filter funnel to provide the desired product (0.42 g, 80% yield). LCMS for $C_{17}H_{18}O_3N_2$ $(M+H)^+$: calculated m/z=296.1. found 296.1.

Step 3. 6-(5-Methoxypyridin-3-yl)benzo[d]oxazole-2-carbaldehyde

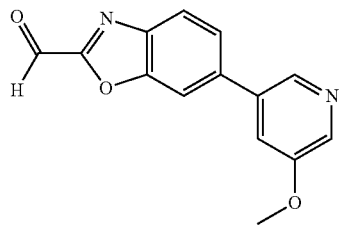 [SMILES: COc1cncc(-c2ccc3nc(C=O)oc3c2)c1]

(E)-2-[6-(5-Methoxypyridin-3-yl)-1,3-benzoxazol-2-yl]-N,N-dimethylethenamine (0.1 g, 0.3 mmol) was suspended in tetrahydrofuran (5 mL) and water (5 mL). To this suspension, sodium periodate (0.29 g, 1.4 mmol) was added and the mixture was stirred at 40° C. for 1 h. The reaction mixture was dilute with ethyl acetate/brine (3:1, 30 mL) and the organic layers were separated. The aqueous layer was extracted with ethyl acetate (2×10 mL). The combined organic layers were dried over sodium sulfate, filtered and concentrated under vacuum. The crude product was used in the next step without purification.

Step 4. 2-(6-Bromo-1H-benzo[d]imidazol-2-yl)-6-(5-methoxypyridin-3-yl)benzo[d]oxazole Sodium metabisulfite (0.011 g, 0.059 mmol) was added to a solution of 4-bromobenzene-1,2-diamine [Aldrich, 640441] (0.0088 g, 0.047 mmol) and 6-(5-methoxypyridin-3-yl)-1,3-benzoxazole-2-carbaldehyde (0.010 g, 0.039 mmol) in N,N-dimethylformamide (2 mL). The resultant mixture was heated at 80° C. for 3 h. After cooling to room temperature, the solvent was evaporated by $N_2$. The residue was suspended in methanol (5 mL), and filtered through diatomaceous earth. The filtrate was purified by prep-HPLC on a C-18 column eluting with a water:acetonitrile gradient buffered at pH 10 with 0.1% ammonium hydroxide, to afford the title compound as a white amorphous solid (0.002 g, 12%). LCMS for $C_{20}H_{14}O_2N_4Br$ (M+H)+: calculated m/z=421.0, 423.0. found: 421.0, 423.0.

Example 10

2-(5-Fluoro-1H-benzo[d]imidazol-2-yl)-6-(5-methoxypyridin-3-yl)benzo[d]oxazole

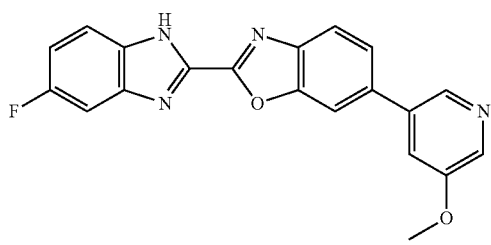 [SMILES: COc1cncc(-c2ccc3nc(-c4nc5cc(F)ccc5[nH]4)oc3c2)c1]

Step 1.
5-Fluoro-2-(trichloromethyl)-1H-benzo[d]imidazole

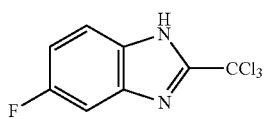

To a solution of 4-fluorobenzene-1,2-diamine [Aldrich, 653586] (0.03 g, 0.2 mmol) in acetic acid (1 mL) was added methyl 2,2,2-trichloroethanimidoate [Acros, AC16093-0250] (0.030 mL, 0.24 mmol) dropwise at room temperature. The mixture was stirred at room temperature for 2 h and poured into water (25 mL). The precipitate was separated by filtration and air-dried, which was directly used in the next step without purification.

Step 2. 2-(5-Fluoro-1H-benzo[d]imidazol-2-yl)-6-(5-methoxypyridin-3-yl)benzo[d]oxazole To a solution of 5-fluoro-2-(trichloromethyl)-1H-benzimidazole (0.03 g, 0.1 mmol) and 2-amino-5-(5-methoxypyridin-3-yl)phenol (0.024 g, 0.11 mmol) in ethanol (1 mL) was added triethylamine (0.047 mL, 0.34 mmol) dropwise over 1 min. After stirring at room temperature for 2 h, methanol (4 mL) was added. The resulting mixture was purified by prep-HPLC on a C-18 column eluting with a water:acetonitrile gradient buffered at pH 10 with 0.1% ammonium hydroxide, to afford the title compound as a white amorphous solid (0.020 g, 50%). LCMS for $C_{20}H_{14}N_4O_2F$ (M+H)+: calculated m/z=361.1. found: 361.1 $^1$H NMR (400 MHz, MeOD) δ 8.83 (d, J=1.5 Hz, 1H), 8.57 (d, J=2.5 Hz, 1H), 8.48-8.41 (m, 1H), 8.29 (d, J=1.5 Hz, 1H), 8.05 (d, J=8.4 Hz, 1H), 7.93 (dd, J=8.4, 1.7 Hz, 1H), 7.76 (dd, J=9.0, 4.7 Hz, 1H), 7.45 (dd, J=8.9, 2.4 Hz, 1H), 7.23 (td, J=9.4, 2.4 Hz, 1H), 4.14 (s, 3H).

Example 11

6-(5-Methoxypyridin-3-yl)-2-(5-methyl-1H-benzo[d]imidazol-2-yl)benzo[d]oxazole

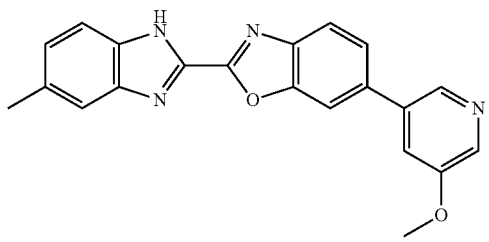 [SMILES: COc1cncc(-c2ccc3nc(-c4nc5cc(C)ccc5[nH]4)oc3c2)c1]

The title compound was synthesized according to an experimental procedure analogous to Example 10, substituting 5-methylbenzene-1,2-diamine [Aldrich, 339928] for 4-fluorobenzene-1,2-diamine. LCMS for $C_{21}H_{17}N_4O_2$ (M+H)+: calculated m/z=357.1. found: 357.1.

Example 12

6-(5-Methoxypyridin-3-yl)-2-(4-methyl-1H-benzo[d]imidazol-2-yl)benzo[d]oxazole

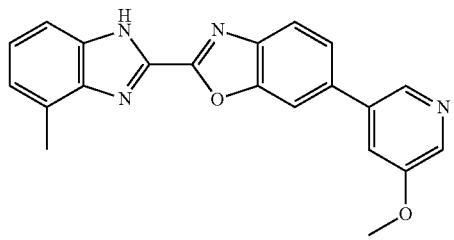 [SMILES: COc1cncc(-c2ccc3nc(-c4nc5c(C)cccc5[nH]4)oc3c2)c1]

The title compound was synthesized according to an experimental procedure analogous to Example 10, substituting 3-methylbenzene-1,2-diamine [Aldrich, 272361] for 4-fluorobenzene-1,2-diamine. LCMS for $C_{21}H_{17}N_4O_2$ (M+H)+: calculated m/z=357.1. found: 357.1 $^1$H NMR (400 MHz, MeOD) δ 8.80 (d, J=1.6 Hz, 1H), 8.52 (d, J=2.6 Hz, 1H), 8.41-8.33 (m, 1H), 8.25 (d, J=1.3 Hz, 1H), 8.03 (d, J=8.4 Hz, 1H), 7.90 (dd, J=8.4, 1.7 Hz, 1H), 7.57 (d, J=8.2 Hz, 1H), 7.40-7.31 (m, 1H), 7.24 (d, J=7.2 Hz, 1H), 4.12 (s, 3H), 2.69 (s, 3H).

Example 13

2-(1H-Benzo[d]imidazol-2-yl)-6-bromobenzo[d]oxazole

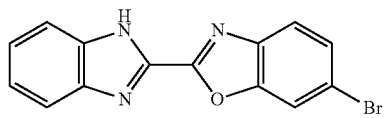 [SMILES: Brc1ccc2nc(-c3nc4ccccc4[nH]3)oc2c1]

Step 1. 2-(Trichloromethyl)-1H-benzo[d]imidazole

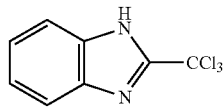

To a solution of 1,2-benzenediamine (2.6 g, 24 mmol) in acetic acid (60 mL), methyl 2,2,2-trichloroethanimidoate (3.1 mL, 25 mmol) was added dropwise at 10° C. The mixture was stirred at room temperature for 5 h, then poured into water (1.0 L). The precipitate was separated by filtration, air-dried, and was directly used for the next step without purification (4.75 g, 84%).

Step 2. 2-(1H-Benzo[d]imidazol-2-yl)-6-bromobenzo[d]oxazole

To a solution of 2-(trichloromethyl)-1H-benzimidazole (1.3 g, 5.6 mmol) and 2-amino-5-bromophenol (1.0 g, 5.0 mmol) in ethanol (10 mL) was added triethylamine (3.0 mL, 21 mmol) dropwise over 1 min. After stirring at room temperature for 2 h, the product was filtered and dried by air. The majority of the product was directly used as a synthetic intermediate without further purification. A small aliquot of the product was diluted in methanol (5 mL) and purified by prep HPLC on a C-18 column eluting with a water:acetonitrile gradient buffered at pH 10 with 0.1% ammonium hydroxide, to afford the title compound as a white amorphous solid. LCMS for $C_{14}H_9BrN_3O$ (M+H)+: calculated m/z=314.0, 316.0. found: 314.0, 316.0.

Example 14

5-(2-(1H-Benzo[d]imidazol-2-yl)benzo[d]oxazol-6-yl)pyridin-3-ol

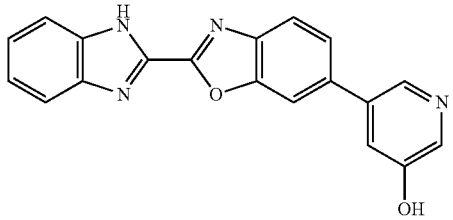 [SMILES: Oc1cncc(-c2ccc3nc(-c4nc5ccccc5[nH]4)oc3c2)c1]

Step 1. 3-Bromo-5-(tert-butyldimethylsilyloxy)pyridine

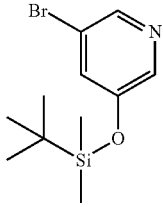

To a solution of 5-bromopyridin-3-ol (5 g, 30 mmol) [Ark Pharm, AK22149] and 1H-imidazole (4.0 g, 60 mmol) in dichloromethane (50 mL, 800 mmol), tert-butyldimethylsilyl chloride (4.8 g, 32 mmol) was added in portions at room temperature. The resultant solution was stirred at room temperature for 5 h. The reaction mixture was dilute with dichloromethane/brine (3:1, 20 mL). The organic layers were separated. The aqueous layer was extracted with dichloromethane (2×10 mL). The combined organic layers were dried over sodium sulfate, filtered, and concentrated under vacuum. The product was directly used in the next step without further purification.

Step 2. 6-Bromo-2-(1-((2-(trimethylsilyl)ethoxy)methyl)-1H-benzo[d]imidazol-2-yl)benzo[d]oxazole

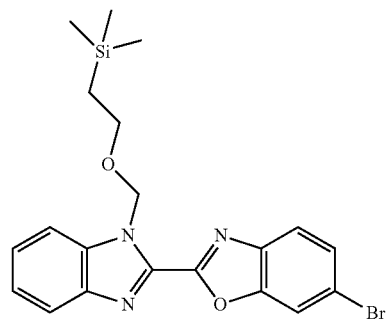 [SMILES: C[Si](C)(C)CCOCn1c(-c2nc3ccc(Br)cc3o2)nc2ccccc21]

A solution of 2-(1H-benzimidazol-2-yl)-6-bromo-1,3-benzoxazole (1.0 g, 3.2 mmol) in tetrahydrofuran (40 mL) at 0° C. was treated with 1.0 M potassium tert-butoxide in THF (3.8 mL, 3.8 mmol) and stirred at 0° C. for 30 min. The reaction mixture was treated with [β-(trimethylsilyl)ethoxy] methyl chloride (0.68 mL, 3.8 mmol) and stirred at 0° C. for 30 min. The reaction was quenched with sat. NH$_4$Cl solution (15 mL) and extracted into ethyl acetate (2×30 mL). The combined organic layers were dried over sodium sulfate, filtered, and concentrated under reduced pressure. The residue was purified by FCC (15-20% ethyl acetate in hexanes) to afford the desired product (1.2 g, 84%). LCMS for $C_{20}H_{23}O_2N_3SiBr$ (M+H)+: calculated m/z=444.1, 446.1. found 444.1, 446.1.

Step 3. 5-(2-(1-((2-(Trimethylsilyl)ethoxy)methyl)-1H-benzo[d]imidazol-2-yl)benzo[d]oxazol-6-yl)pyridin-3-ol

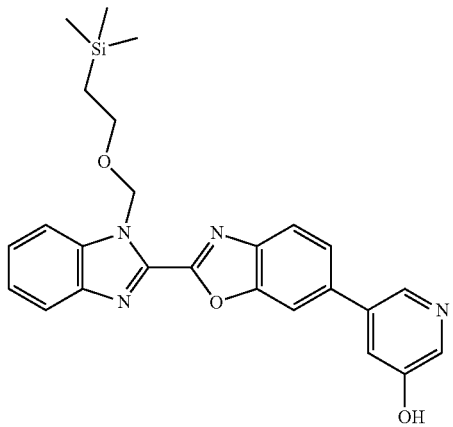 [SMILES: C[Si](C)(C)CCOCn1c(-c2nc3ccc(-c4cncc(O)c4)cc3o2)nc2ccccc21]

A suspension of dicyclohexyl(2',4',6'-triisopropylbiphenyl-2-yl)phosphine (8 mg, 0.02 mmol), potassium acetate (0.10 g, 1.0 mmol), tetrahydroxydiborane (0.091 g, 1.0 mmol), dicyclohexyl(2',4',6'-triisopropylbiphenyl-2-yl)phosphine-(2'-aminobiphenyl-2-yl)(chloro)palladium (1:1) (0.0066 g, 0.0084 mmol) and 6-bromo-2-(1-{[2-(trimethylsilyl)ethoxy]methyl}-1H-benzimidazol-2-yl)-1,3-benzoxazole (0.150 g, 0.338 mmol) in ethanol (4 mL) was degassed and heated at 85° C. for 2 h. After cooling to room temperature, 1.8 M potassium carbonate in water (0.56 mL, 1.0 mmol) was added followed by 3-bromo-5-{[tert-butyl (dimethyl)silyl]oxy}pyridine (98 mg, 0.34 mmol) in ethanol. The resultant mixture was heated at 90° C. for 2 h. After cooling to room temperature, the mixture was diluted with dichloromethane (50 mL), dried over sodium sulfate, filtered through a short plug of silica gel and concentrated via rotovap. The residue was purified by FCC to afford the title compound (0.10 g, 64%). LCMS for $C_{25}H_{27}O_3N_4Si$ (M+H)+: calculated m/z=458.2. found 458.2.

Step 4. 5-(2-(1H-Benzo[d]imidazol-2-yl)benzo[d]oxazol-6-yl)pyridin-3-ol

To a solution of 5-(2-(1-((2-(trimethylsilyl)ethoxy)methyl)-1H-benzo[d]imidazol-2-yl)benzo[d]oxazol-6-yl)pyridin-3-ol (0.02 g, 0.04 mmol) in dichloromethane (0.5 mL) was added trifluoroacetic acid (0.5 mL). The mixture was stirred at 40° C. for 0.5 h. After evaporation of the solvents by $N_2$, the resulting residue was dissolved in methanol and 10% ammonium hydroxide (1 mL) was added. After stirring at room temperature for 0.5 h, the mixture was diluted with methanol/N,N-dimethylformamide (1:1, 4 mL), filtered and the filtrate was purified by HPLC on a C-18 column eluting with a water:acetonitrile gradient buffered at pH 10 with 0.1% ammonium hydroxide, to afford the title compound as a white solid (0.007 g, 49%). LCMS for $C_{19}H_{13}O_2N_4$ (M+H)+: calculated m/z=329.1. found 329.1.

Example 15

2-(1H-Benzo[d]imidazol-2-yl)-6-(5-isopropoxypyridin-3-yl)benzo[d]oxazole

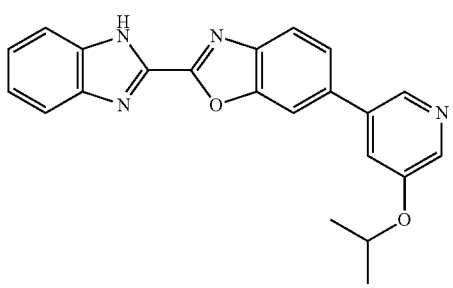 [SMILES: CC(C)Oc1cncc(-c2ccc3nc(-c4nc5ccccc5[nH]4)oc3c2)c1]

Step 1. 6-(5-Isopropoxypyridin-3-yl)-2-(1-((2-(trimethylsilyl)ethoxy)methyl)-1H-benzo[d]imidazol-2-yl)benzo[d]oxazole

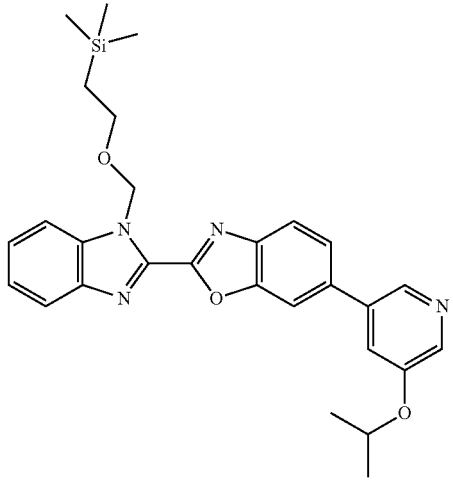 [SMILES: CC(C)Oc1cncc(-c2ccc3nc(-c4nc5ccccc5n4COCC[Si](C)(C)C)oc3c2)c1]

Triphenylphosphine (0.149 g, 0.567 mmol) was added to a solution of 5-[2-(1-{[2-(trimethylsilyl)ethoxy]methyl}-1H-benzimidazol-2-yl)-1,3-benzoxazol-6-yl]pyridin-3-ol (0.0866 g, 0.189 mmol) and isopropyl alcohol (43.4 µL, 0.567 mmol) in tetrahydrofuran (10 mL). Diisopropyl azodicarboxylate (112 µL, 0.567 mmol) was added to the resulting mixture at 0° C. The reaction was then stirred at room temperature for 15 h. After concentrating under reduced pressure, the resulting residue was purified by FCC to afford the title compound (0.07 g, 74%). LCMS for $C_{28}H_{33}O_3N_4Si$ (M+H)−: calculated m/z=501.2. found 501.2.

Step 2. 2-(1H-Benzo[d]imidazol-2-yl)-6-(5-isopropoxypyridin-3-yl)benzo[d]oxazole Trifluoroacetic acid (0.5 mL) was added to a solution of 6-(5-isopropoxypyridin-3-yl)-2-(1-((2-(trimethylsilyl)ethoxy)methyl)-1H-benzo[d]imidazol-2-yl)benzo[d]oxazole (0.02 g, 0.04 mmol) in dichloromethane (0.5 mL). The resultant mixture was stirred at 40° C. for 0.5 h. The solvent was then evaporated by $N_2$. The resulting residue was dissolved in methanol (1 mL) and 10% ammonium hydroxide (0.5 mL) was added. After stirring at room temperature for 0.5 h, the mixture was diluted with methanol:N,N-dimethylformamide (1:1, 4 mL) and filtered. The filtrate was purified by HPLC on a C-18 column eluting with a water:acetonitrile gradient buffered at pH 10 with 0.1% ammonium hydroxide, to afford the title compound as a white amorphous solid (0.007 g, 47%). LCMS for $C_{19}H_{13}O_2N_4$ (M+H)+: calculated m/z=371.2. found 371.2.

Example 16

2-(1H-Benzo[d]imidazol-2-yl)-6-(5-(difluoromethoxy)pyridin-3-yl)benzo[d]oxazole

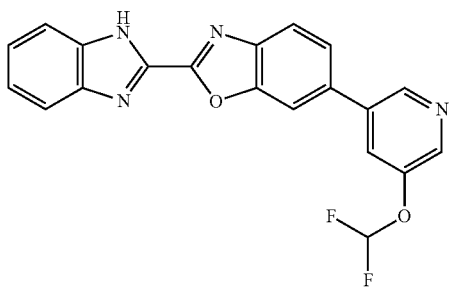 [SMILES: FC(F)Oc1cncc(-c2ccc3nc(-c4nc5ccccc5[nH]4)oc3c2)c1]

Step 1. 6-(5-(Difluoromethoxy)pyridin-3-yl)-2-(1-((2-(trimethylsilyl)ethoxy)methyl)-1H-benzo[d]imidazol-2-yl)benzo[d]oxazole

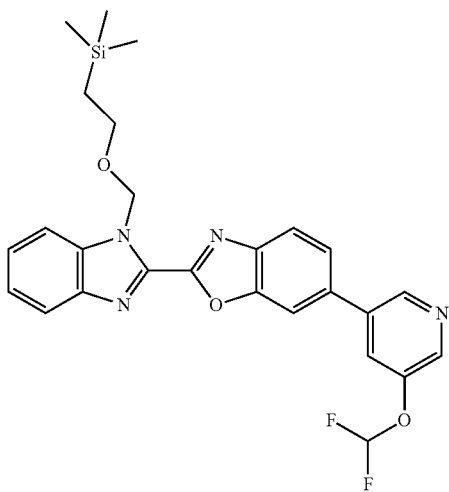 [SMILES: C[Si](C)(C)CCOCn1c(-c2nc3ccc(-c4cncc(OC(F)F)c4)cc3o2)nc2ccccc21]

A mixture of 5-[2-(1-{[2-(trimethylsilyl)ethoxy]methyl}-1H-benzimidazol-2-yl)-1,3-benzoxazol-6-yl]pyridin-3-ol (0.025 g, 0.049 mmol), sodium chlorodifluoroacetate [Aldrich, 374067] (0.012 g, 0.082 mmol) and potassium carbonate (0.015 g, 0.11 mmol) in acetonitrile (1 mL) was refluxed for 4 h. The reaction was cooled and diluted with dichloromethane, washed with saturated sodium carbonate, dried over sodium sulfate, filtered and concentrated under reduced pressure. The resulting residue was purified by FCC to afford the title compound (0.020 g, 80%). LCMS for $C_{26}H_{27}N_4O_3SiF_2$ (M+H)+: calculated m/z=509.2. found 509.2.

Step 2. 2-(1H-Benzo[d]imidazol-2-yl)-6-(5-(difluoromethoxy)pyridin-3-yl)benzo[d]oxazole Trifluoroacetic acid (0.5 mL) was added to a solution of 6-(5-(difluoromethoxy)pyridin-3-yl)-2-(1-((2-(trimethylsilyl)ethoxy)methyl)-1H-benzo[d]imidazol-2-yl)benzo[d]oxazole (0.02 g, 0.04 mmol) in dichloromethane (0.5 mL, 8 mmol). The mixture was stirred at 40° C. for 0.5 h. The solvent was evaporated by $N_2$. The residue was dissolved in methanol (1 mL) and 10% ammonium hydroxide (0.5 mL) was added. After stirring at room temperature for 0.5 h, the mixture was diluted with methanol:N,N-dimethylformamide (1:1, 4 mL) and filtered. The filtrate was purified by HPLC on a C-18 column eluting with a water:acetonitrile gradient buffered at pH 10 with 0.1% ammonium hydroxide, to afford the title compound as a white amorphous solid (0.007 g, 46%). LCMS for $C_{20}H_{13}F_2N_4O_2$ (M+H)+: calculated m/z=379.1. found 379.1.

Example 17

N-(5-(2-(1H-Benzo[d]imidazol-2-yl)benzo[d]oxazol-6-yl)pyridin-3-yl)-4-fluorobenzenesulfonamide

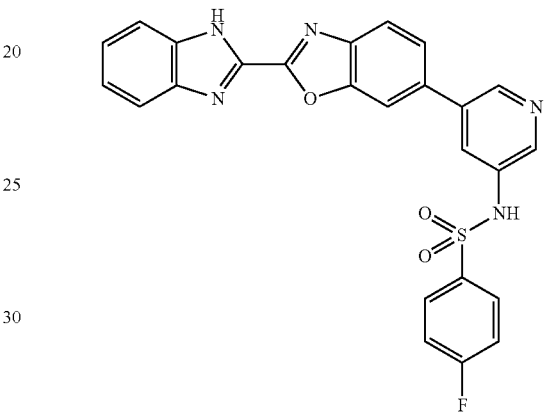

Step 1. 5-(2-(1-((2-(Trimethylsilyl)ethoxy)methyl)-1H-benzo[d]imidazol-2-yl)benzo[d]oxazol-6-yl)pyridin-3-amine

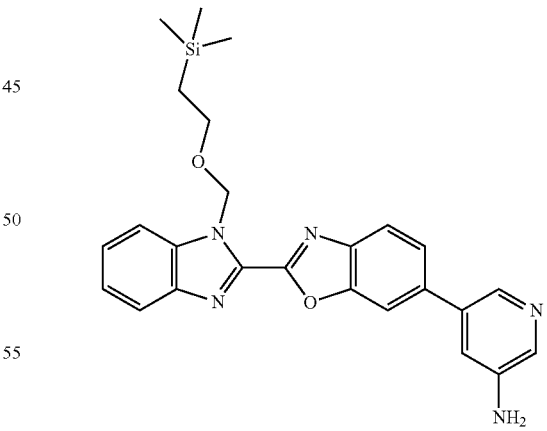

A suspension of dicyclohexyl(2',4',6'-triisopropylbiphenyl-2-yl)phosphine (20 mg, 0.04 mmol) potassium acetate (0.24 g, 2.4 mmol), tetrahydroxydiborane (0.22 g, 2.4 mmol), dicyclohexyl(2',4',6'-triisopropylbiphenyl-2-yl)phosphine-(2'-aminobiphenyl-2-yl)(chloro)palladium (1:1) (0.016 g, 0.020 mmol) and 6-bromo-2-(1-{[2-(trimethylsilyl)ethoxy]methyl}-1H-benzimidazol-2-yl)-1,3-benzoxazole (360 mg, 0.81 mmol) in ethanol (10 mL) was degassed by N₂ and heated at 85° C. for 2 h. After cooling to room temperature, potassium carbonate solution (1.8 M, 1.4 mL, 2.4 mmol) was added followed by 5-bromopyridin-3-amine [Combi-Blocks, PY7125] (0.14 g, 0.81 mmol) in ethanol (2 mL). The resulting mixture was heated at 90° C. for 2 h. After cooling to room temperature, the mixture was diluted with dichloromethane (50 mL), dried over sodium sulfate, filtered, and concentrated under reduced pressure. The resulting residue was purified by FCC to afford the title compound (0.3 g, 80%) LCMS for $C_{25}H_{28}O_2N_5Si$ (M+H)⁺: calculated m/z=458.2. found 458.1.

Step 2. N-(5-(2-(1H-Benzo[d]imidazol-2-yl)benzo[d]oxazol-6-yl)pyridin-3-yl)-4-fluorobenzenesulfonamide To a solution of 5-[2-(1-{[2-(trimethylsilyl)ethoxy]methyl}-1H-benzimidazol-2-yl)-1,3-benzoxazol-6-yl]pyridin-3-amine (10 mg, 0.02 mmol) in pyridine (0.5 mL, 6 mmol), was added 4-fluorobenzenesulfonyl chloride (10 mg, 0.07 mmol) at room temperature. After 30 min, the solvent was evaporated by N₂. The residue was diluted in dichloromethane (0.5 mL). To the solution was added trifluoroacetic acid (0.5 mL) dropwise at room temperature. The resulting mixture was heated at 40° C. for 30 min. The solvent was then evaporated by N₂. The residue was dissolved in methanol (1 mL) and 10% ammonium hydroxide (0.5 mL) was added. After stirring at room temperature for 0.5 h, the mixture was diluted with methanol:N,N-dimethylformamide (1:1, 4 mL), filtered and the filtrate was purified by HPLC on a C-18 column eluting with a water:acetonitrile gradient buffered at pH 10 with 0.1% ammonium hydroxide, to afford the title compound as a white amorphous solid (2 mg, 20%) LCMS for $C_{25}H_{17}FN_5O_3S$ (M+H)+: calculated m/z=486.1. found 486.1 ¹H NMR (500 MHz, dmso) δ 8.67 (d, J=1.7 Hz, 1H), 8.34 (d, J=2.3 Hz, 1H), 8.10 (s, 1H), 7.99 (d, J=8.3 Hz, 1H), 7.95-7.88 (m, 2H), 7.81 (t, J=2.1 Hz, 1H), 7.73 (s, 2H), 7.69 (dd, J=8.3, 1.3 Hz, 1H), 7.40 (t, J=8.8 Hz, 2H), 7.36 (dd, J=6.1, 3.1 Hz, 2H).

Examples 18 to 33

Examples 18 to 33 were synthesized according to the procedure of Example 17 and the data are listed in Table 1.

TABLE 1

| Ex. No. | Name | Rˣ | Rʸ | MS [M + H]⁺ | ¹H NMR Spectrum |
|---|---|---|---|---|---|
| 18 | N-(5-(2-(1H-Benzo[d]imidazol-2-yl)benzo[d]oxazol-6-yl)pyridin-3-yl)ethanesulfonamide | ethanesulfonyl group | H | 402.1 | ¹H NMR (400 MHz, MeOD) δ 8.81 (s, 1H), 8.58 (s, 1H), 8.28 (s, 1H), 8.19 (s, 1H), 8.05 (d, J = 8.3 Hz, 1H), 7.86 (d, J = 8.4 Hz, 1H), 7.80 (dd, J = 6.1, 3.1 Hz, 2H), 7.49 (dd, J = 6.0, 3.2 Hz, 2H), 3.38-3.32 (m, 2H), 1.41 (t, J = 7.3 Hz, 3H). |
| 19 | N-(5-(2-(1H-Benzo[d]imidazol-2-yl)benzo[d]oxazol-6-yl)pyridin-3-yl)-3-fluorobenzenesulfonamide | 3-fluorophenylsulfonyl group | H | 486.1 | |
| 20 | N-(5-(2-(1H-Benzo[d]imidazol-2-yl)benzo[d]oxazol-6-yl)pyridin-3-yl)piperidine-1-sulfonamide | piperidine-1-sulfonyl group | H | 475.2 | |

TABLE 1-continued

| Ex. No. | Name | R$^x$ | R$^y$ | MS [M + H]$^+$ | $^1$H NMR Spectrum |
|---|---|---|---|---|---|
| 21 | N'-{5-[2-(1H-Benzimidazol-2-yl)-1,3-benzoxazol-6-yl]-pyridin-3-yl}-N,N-dimethylsulfamide | -S(O)$_2$NH-N(CH$_3$)$_2$ | H | 435.1 | $^1$H NMR (400 MHz, MeOD) δ 8.76 (d, J = 1.6 Hz, 1H), 8.52 (d, J = 2.2 Hz, 1H), 8.21 (t, J = 2.1 Hz, 1H), 8.15 (d, J = 1.3 Hz, 1H), 8.03 (d, J = 8.4 Hz, 1H), 7.82 (dd, J = 8.4, 1.7 Hz, 1H), 7.77 (dt, J = 6.6, 3.3 Hz, 2H), 7.47 (dt, J = 6.2, 3.2 Hz, 2H), 2.91 (s, 6H). |
| 22 | N'-{5-[2-(1H-Benzimidazol-2-yl)-1,3-benzoxazol-6-yl]-2-methylpyridin-3-yl}-N,N-dimethylsulfamide | -S(O)$_2$NH-N(CH$_3$)$_2$ | CH$_3$ | 449.1 | $^1$H NMR (400 MHz, MeOH) δ 8.82 (d, J = 2.0 Hz, 1H), 8.62 (d, J = 2.0 Hz, 1H), 8.16 (d, J = 1.4 Hz, 1H), 8.03 (d, J = 8.4 Hz, 1H), 7.82 (dd, J = 8.4, 1.7 Hz, 1H), 7.76 (dt, J = 6.5, 3.3 Hz, 2H), 7.46 (dt, J = 6.2, 3.2 Hz, 2H), 2.93 (s, 6H), 2.78 (s, 3H) |
| 23 | N'-{5-[2-(1H-Benzimidazol-2-yl)-1,3-benzoxazol-6-yl]-2-fluoropyridin-3-yl}-N,N-dimethylsulfamide | -S(O)$_2$NH-N(CH$_3$)$_2$ | F | 453.1 | $^1$H NMR (400 MHz, MeOD) δ 8.29-8.24 (m, 2H), 8.05 (d, J = 1.3 Hz, 1H), 7.99 (d, J = 8.3 Hz, 1H), 7.78 (dd, J = 6.2, 3.1 Hz, 2H), 7.74 (dd, J = 8.4, 1.6 Hz, 1H), 7.48 (dt, J = 6.2, 3.2 Hz, 2H), 2.94 (s, 3H), 2.86 (s, 3H) |
| 24 | N-(5-(2-(1H-Benzo[d]imidazol-2-yl)benzo[d]oxazol-6-yl)pyridin-3-yl)propane-2-sulfonamide | -S(O)$_2$NH-CH(CH$_3$)$_2$ | H | 434.1 | $^1$H NMR (400 MHz, MeOD) δ 8.76 (s, 1H), 8.56 (s, 1H), 8.23 (t, J = 2.1 Hz, 1H), 8.17 (d, J = 1.3 Hz, 1H), 8.04 (d, J = 8.4 Hz, 1H), 7.83 (dd, J = 8.4, 1.7 Hz, 1H), 7.78 (dd, J = 6.2, 3.1 Hz, 2H), 7.47 (dd, J = 6.2, 3.1 Hz, 2H), 3.55-3.41 (m, 1H), 1.44 (s, 3H), 1.42 (s, 3H) |
| 25 | N-(5-(2-(1H-Benzo[d]imidazol-2-yl)benzo[d]oxazol-6-yl)-2-methylpyridin-3-yl)ethanesulfonamide | -S(O)$_2$NH-CH$_2$CH$_3$ | CH$_3$ | 434.1 | $^1$H NMR (400 MHz, MeOD) δ 8.85 (d, J = 2.0 Hz, 1H), 8.68 (d, J = 2.0 Hz, 1H), 8.14 (d, J = 1.3 Hz, 1H), 7.97 (d, J = 8.4 Hz, 1H), 7.80 (dd, J = 8.4, 1.7 Hz, 1H), 7.74 (dt, J = 6.5, 3.3 Hz, 2H), 7.46 (dt, J = 6.2, 3.3 Hz, 2H), 3.38 (q, J = 7.4 Hz, 2H), 2.78 (s, 3H), 1.45 (t, J = 7.4 Hz, 3H) |
| 26 | N-(5-(2-(1H-Benzo[d]imidazol-2-yl)benzo[d]oxazol-6-yl)-2-chloropyridin-3-yl)ethanesulfonamide | -S(O)$_2$NH-CH$_2$CH$_3$ | Cl | 454.1 | $^1$H NMR (400 MHz, MeOD) δ 8.59 (d, J = 2.3 Hz, 1H), 8.33 (d, J = 2.3 Hz, 1H), 8.13 (d, J = 1.2 Hz, 1H), 8.01 (d, J = 8.4 Hz, 1H), 7.79 (ddd, J = 11.6, 7.2, 2.4 Hz, 3H), 7.46 (dd, J = 6.2, 3.1 Hz, 2H), 1.42 (t, J = 7.4 Hz, 3H) |
| 27 | N-(5-(2-(1H-Benzo[d]imidazol-2-yl)benzo[d]oxazol-6-yl)-2-fluoropyridin-3-yl)ethanesulfonamide | -S(O)$_2$NH-CH$_2$CH$_3$ | F | 438.1 | $^1$H NMR (400 MHz, MeOD) δ 9.13-9.05 (m, 1H), 9.01 (dd, J = 9.3, 2.3 Hz, 1H), 8.87 (d, J = 1.3 Hz, 1H), 8.73 (d, J = 8.3 Hz, 1H), 8.55-8.44 (m, 3H), 8.15 (dd, J = 6.2, 3.1 Hz, 2H), 2.10 (t, J = 7.4 Hz, 3H). |

TABLE 1-continued

| Ex. No. | Name | R$^x$ | R$^y$ | MS [M + H]$^+$ | $^1$H NMR Spectrum |
|---|---|---|---|---|---|
| 28 | N-(5-(2-(1H-Benzo[d]imidazol-2-yl)benzo[d]oxazol-6-yl)-2-methylpyridin-3-yl)-4-fluorobenzenesulfonamide | 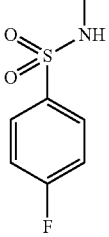 | CH3 | 500.1 | |
| 29 | N-(5-(2-(1H-Benzo[d]imidazol-2-yl)benzo[d]oxazol-6-yl)-2-chloropyridin-3-yl)-4-fluorobenzenesulfonamide | 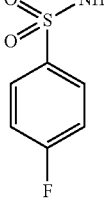 | Cl | 520.1 | |
| 30 | N-(5-(2-(1H-Benzo[d]imidazol-2-yl)benzo[d]oxazol-6-yl)-2-fluoropyridin-3-yl)-4-fluorobenzenesulfonamide | 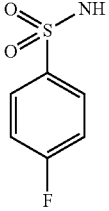 | F | 504.1 | $^1$H NMR (400 MHz, MeOD) δ 9.15-9.07 (m, 1H), 8.94 (dd, J = 9.2, 2.3 Hz, 1H), 8.85 (d, J = 1.4 Hz, 1H), 8.75 (d, J = 8.3 Hz, 1H), 8.68-8.59 (m, 2H), 8.53-8.45 (m, 3H), 8.15 (dt, J = 6.2, 3.4 Hz, 2H), 8.13-8.06 (m, 2H). |
| 31 | N-(5-(2-(1H-Benzo[d]imidazol-2-yl)benzo[d]oxazol-6-yl)pyridin-3-yl)-4-methylpiperazine-1-sulfonamide | 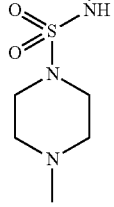 | H | 490.2 | |

TABLE 1-continued

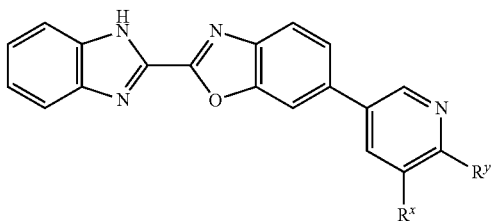

| Ex. No. | Name | $R^x$ | $R^y$ | MS [M + H]$^+$ | $^1$H NMR Spectrum |
|---|---|---|---|---|---|
| 32 | N-(5-(2-(1H-Benzo[d]imidazol-2-yl)benzo[d]oxazol-6-yl)-2-fluoropyridin-3-yl)-4-methylpiperazine-1-sulfonamide | (structure) | F | 508.2 | |
| 33 | N-(5-(2-(1H-Benzo[d]imidazol-2-yl)benzo[d]oxazol-6-yl)pyridin-3-yl)acetamide | (structure) | H | 370.1 | $^1$H NMR (400 MHz, DMSO) δ 10.32 (s, 1H), 8.76 (d, J = 2.2 Hz, 1H), 8.70 (d, J = 2.0 Hz, 1H), 8.39 (s, 1H), 8.22 (s, 1H), 8.02 (d, J = 8.3 Hz, 1H), 7.78 (dd, J = 8.3, 1.4 Hz, 2H), 7.71 (s, 1H), 7.34 (dd, J = 6.1, 3.1 Hz, 3H), 2.13 (s, 3H). |

Example 34

5-(2-(1H-Benzo[d]imidazol-2-yl)benzo[d]oxazol-6-yl)-N,N-dimethylpyridin-3-amine

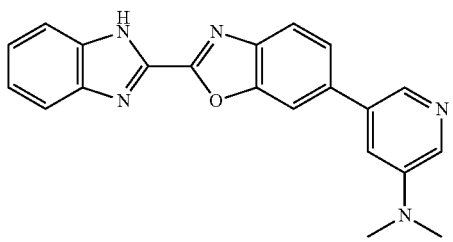 [SMILES: CN(C)c1cncc(-c2ccc3nc(-c4nc5ccccc5[nH]4)oc3c2)c1]

Acetic acid (0.01 mL, 0.176 mmol) was added to a solution of 5-[2-(1-{[2-(trimethylsilyl)ethoxy]methyl}-1H-benzimidazol-2-yl)-1,3-benzoxazol-6-yl]pyridin-3-amine (0.040 g, 0.090 mmol) and formaldehyde (0.011 g, 0.13 mmol) in dichloromethane (1 mL) at room temperature. After 5 min, sodium triacetoxyborohydride (0.060 g, 0.30 mmol) in dichloromethane (0.5 mL) was added in portions. After stirring at room temperature for 1 h, the reaction mixture was concentrated and diluted with ethyl acetate and washed with saturated sodium bicarbonate. The aqueous layer was extracted with dichloromethane (3×10 mL). The combined organic layers were dried over sodium sulfate, filtered, and concentrated. The residue was then diluted in dichloromethane (0.5 mL). To the solution was added trifluoroacetic acid (0.5 mL) dropwise at room temperature and the resulting mixture was heated at 40° C. for 30 min. The solvent was then evaporated by N$_2$. The residue was dissolved in methanol (1 mL) and 10% ammonium hydroxide (0.5 mL) was added. After stirring at room temperature for 0.5 h, the mixture was diluted with methanol:N,N-dimethylformamide (1:1, 4 mL) and filtered. The filtrate was purified by HPLC on a C-18 column eluting with a water:acetonitrile gradient buffered at pH 10 with 0.1% ammonium hydroxide, to afford the title compound as a white amorphous solid (0.010 g, 30%) LCMS for C$_{21}$H$_{18}$N$_5$O (M+H)+: calculated m/z=356.2. found 356.2.

Example 35

5-(2-(1H-Benzo[d]imidazol-2-yl)benzo[d]oxazol-6-yl)nicotinonitrile

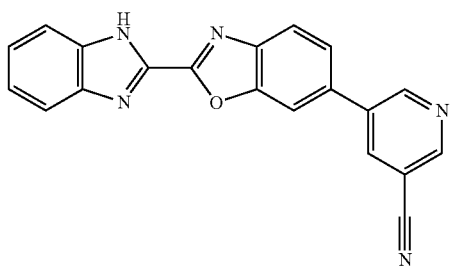 [SMILES: N#Cc1cncc(-c2ccc3nc(-c4nc5ccccc5[nH]4)oc3c2)c1]

A suspension of dicyclohexyl(2',4',6'-triisopropylbiphenyl-2-yl)phosphine (10 mg, 0.02 mmol), potassium acetate (0.13 g, 1.4 mmol), tetrahydroxydiborane (120 mg, 1.4 mmol), dicyclohexyl(2',4',6'-triisopropylbiphenyl-2-yl)phosphine-(2'-aminobiphenyl-2-yl)(chloro)palladium (1:1) (0.0088 g, 0.011 mmol) and 6-bromo-2-(1-{[2-(trimethylsilyl)ethoxy]methyl}-1H-benzimidazol-2-yl)-1,3-benzoxazole (200 mg, 0.4 mmol) in ethanol (6 mL, 90 mmol) was degassed for 5 min. The resulting mixture was heated at 85° C. for 1.5 h. After cooling to room temperature, 1.8 M potassium carbonate in water (0.75 mL, 1.4 mmol) was added, followed by 5-bromonicotinonitrile [Aldrich, 574422] (82 mg, 0.45 mmol) in ethanol (2 mL). The resultant mixture was heated at 90° C. for 2 h. After cooling to room temperature, the mixture was diluted with dichloromethane (20 mL), dried over sodium sulfate, filtered, and concentrated. The residue was then diluted in dichloromethane (1 mL). To the solution was added trifluoroacetic acid (1 mL) dropwise at room temperature and the resulting mixture was heated at 40° C. for 30 min. The solvent was then evaporated by $N_2$. The residue was dissolved in methanol (2 mL) and 10% ammonium hydroxide (1 mL) was added. After stirring at room temperature for 0.5 h, the mixture was diluted with methanol:N,N-dimethylformamide (1:1, 4 mL) and filtered. The filtrate was purified by HPLC on a C-18 column eluting with a water:acetonitrile gradient buffered at pH 10 with 0.1% ammonium hydroxide, to afford the title compound as a white amorphous solid (0.07 g, 52%) LCMS for $C_{20}H_{12}N_5O$ (M+H)+: calculated m/z=338.1. found 338.1.

Example 36

2-(1H-Benzo[d]imidazol-2-yl)-6-(5-(methylsulfonyl)pyridin-3-yl)benzo[d]oxazole

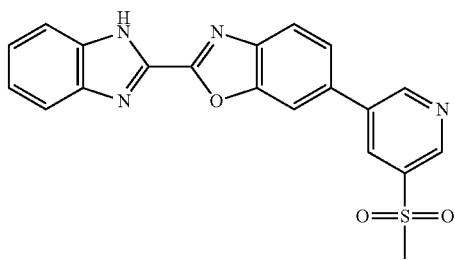 [SMILES: CS(=O)(=O)c1cncc(-c2ccc3nc(-c4nc5ccccc5[nH]4)oc3c2)c1]

The title compound was synthesized according to an experimental procedure analogous to the synthesis of Example 35, substituting 3-bromo-5-(methylsulfonyl)pyridine [Combi-Blocks, PY7190] for 5-bromonicotinonitrile. LCMS calculated for $C_{20}H_{15}N_4O_3S$ (M+H)+: m/z=391.1. found: 391.1.

Example 37

5-[2-(1H-benzimidazol-2-yl)-1,3-benzoxazol-6-yl]-N,N-dimethylpyridine-3-sulfonamide

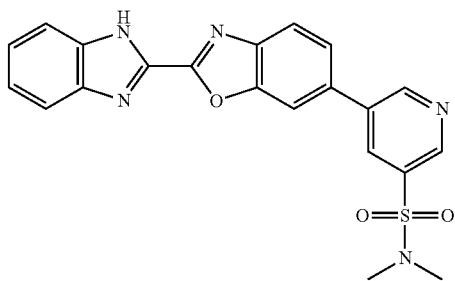 [SMILES: CN(C)S(=O)(=O)c1cncc(-c2ccc3nc(-c4nc5ccccc5[nH]4)oc3c2)c1]

Step 1.
5-Bromo-N,N-dimethylpyridine-3-sulfonamide

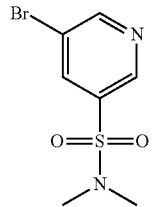

To a solution of triethylamine (0.5 mL, 4 mmol) in dichloromethane (5 mL) was added 2.0 M dimethylamine in tetrahydrofuran (0.58 mL, 1.2 mmol). The resultant solution was cooled to 0° C. and 5-bromopyridine-3-sulfonyl chloride [Combi-Blocks, ST-7824] (200 mg, 0.8 mmol) in dichloromethane (1 mL) was added dropwise. After stirring at 0° C. to room temperature over 1 h, the reaction mixture was concentrated via rotovap. The residue was purified by FCC to afford the title compound (0.12 g, 60%) LCMS for $C_7H_{10}BrN_2O_2S$ (M+H)+: calculated m/z=265.0, 267.0. found 264.9, 266.9.

Step 2. 5-[2-(1H-benzimidazol-2-yl)-1,3-benzoxazol-6-yl]-N,N-dimethylpyridine-3-sulfonamide The title compound was synthesized according to an experimental procedure analogous to the synthesis of Example 35, substituting 5-bromo-N,N-dimethylpyridine-3-sulfonamide for 5-bromonicotinonitrile. LCMS for $C_{21}H_{18}N_5O_3S$ (M+H)+: calculated m/z=420.1. found 420.2
$^1$H NMR (400 MHz, MeOD) δ 9.22 (d, J=2.2 Hz, 1H), 8.96 (d, J=2.1 Hz, 1H), 8.48 (t, J=2.1 Hz, 1H), 8.23 (d, J=1.4 Hz, 1H), 8.03 (d, J=8.3 Hz, 1H), 7.87 (dd, J=8.4, 1.7 Hz, 1H), 7.76 (dd, J=5.8, 3.2 Hz, 2H), 7.47-7.34 (m, 2H), 2.83 (s, 6H).

Example 38

2-(1H-Benzo[d]imidazol-2-yl)-6-(5-(morpholinosulfonyl)pyridin-3-yl)benzo[d]oxazole

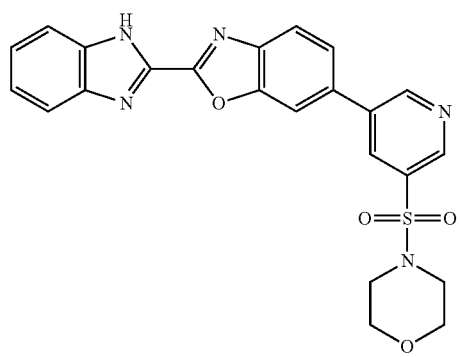 [SMILES: O=S(=O)(c1cncc(-c2ccc3nc(-c4nc5ccccc5[nH]4)oc3c2)c1)N1CCOCC1]

Step 1. 4-(5-Bromopyridin-3-ylsulfonyl)morpholine

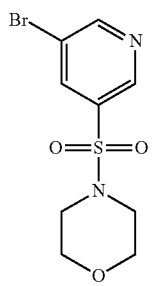

The title compound was synthesized according to an experimental procedure analogous to the synthesis of Example 37, substituting morpholine for dimethylamine. LCMS for $C_9H_{12}BrN_2O_3S$ (M+H)+: calculated m/z=307.0, 309.0. found 306.9, 308.9.

Step 2. 2-(1H-Benzo[d]imidazol-2-yl)-6-(5-(morpholinosulfonyl)pyridin-3-yl)benzo[d]oxazole The title compound was synthesized according to an experimental procedure analogous to the synthesis of Example 35, substituting 4-(5-bromopyridin-3-ylsulfonyl)morpholine for 5-bromonicotinonitrile. LCMS for $C_{23}H_{20}N_5O_4S$ (M+H)+: calculated m/z=462.1. found 462.1 $^1$H NMR (400 MHz, MeOD) δ 9.24 (d, J=2.2 Hz, 1H), 8.95 (d, J=2.0 Hz, 1H), 8.47 (t, J=2.1 Hz, 1H), 8.23 (d, J=1.3 Hz, 1H), 8.03 (d, J=8.3 Hz, 1H), 7.88 (dd, J=8.3, 1.7 Hz, 1H), 7.76 (dd, J=5.9, 3.3 Hz, 2H), 7.41 (tt, J=6.8, 3.5 Hz, 2H), 3.81-3.71 (m, 4H), 3.18-3.08 (m, 4H).

Example 39

N-(5-(2-(1H-Imidazol-2-yl)benzo[d]oxazol-6-yl)pyridin-3-yl)-4-fluorobenzenesulfonamide

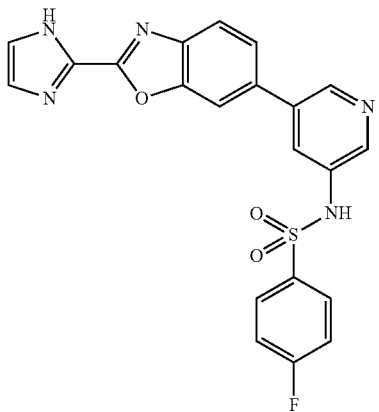 [SMILES: O=S(=O)(Nc1cncc(-c2ccc3nc(-c4ncc[nH]4)oc3c2)c1)c1ccc(F)cc1]

Step 1. 6-Bromo-2-(1H-imidazol-2-yl)benzo[d]oxazole

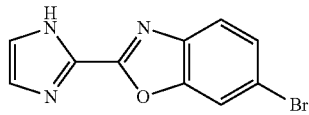 [SMILES: Brc1ccc2nc(-c3ncc[nH]3)oc2c1]

The title compound was synthesized according to an experimental procedure analogous to Example 1, substituting 2-amino-5-bromophenol for 2-amino-5-(5-methoxypyridin-3-yl)phenol. LCMS for $C_{10}H_7BrN_3O$ (M+H)+: calculated m/z=264.0, 266.0. found 263.9, 265.9.

Step 2. 6-Bromo-2-(1-((2-(trimethylsilyl)ethoxy)methyl)-1H-imidazol-2-yl)benzo[d]oxazole

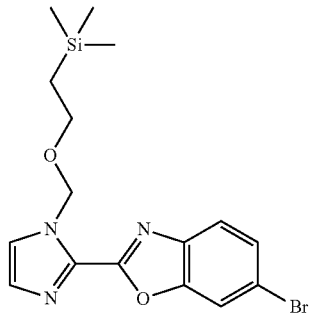 [SMILES: C[Si](C)(C)CCOCn1ccnc1-c1nc2ccc(Br)cc2o1]

The title compound was synthesized according to an experimental procedure analogous to Example 14, Step 2, substituting 6-bromo-2-(1H-imidazol-2-yl)benzo[d]oxazole for 2-(1H-benzimidazol-2-yl)-6-bromo-1,3-benzoxazole. LCMS for $C_{16}H_{21}BrN_3O_2Si$ (M+H)+: calculated m/z=394.1, 396.1. found 394.1, 396.1.

Step 3. 5-(2-(1-((2-(Trimethylsilyl)ethoxy)methyl)-1H-imidazol-2-yl)benzo[d]oxazol-6-yl)pyridin-3-amine

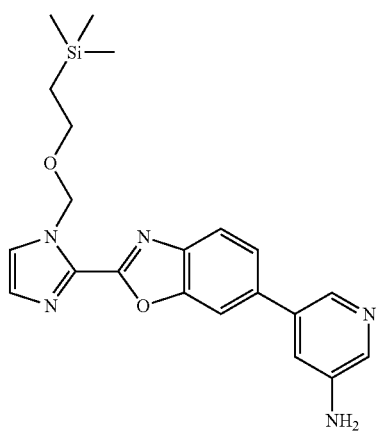 [SMILES: C[Si](C)(C)CCOCn1ccnc1-c1nc2ccc(-c3cncc(N)c3)cc2o1]

The title compound was synthesized according to an experimental procedure analogous to Example 17, Step 1, using 6-bromo-2-(1-((2-(trimethylsilyl)ethoxy)methyl)-1H-imidazol-2-yl)benzo[d]oxazole instead of 6-bromo-2-(1-{[2-(trimethylsilyl)ethoxy]methyl}-1H-benzimidazol-2-yl)-1,3-benzoxazole. LCMS for $C_{21}H_{26}O_2N_5Si$ (M+H)$^+$: calculated m/z=408.2. found 408.2.

Step 4. N-(5-(2-(1H-Imidazol-2-yl)benzo[d]oxazol-6-yl)pyridin-3-yl)-4-fluorobenzenesulfonamide The title compound was synthesized according to an experimental procedure analogous to Example 17, Step 2, using 5-(2-(1-((2-(trimethylsilyl)ethoxy)methyl)-1H-imidazol-2-yl)benzo[d]oxazol-6-yl)pyridin-3-amine instead of 5-[2-(1-{[2-(trimethylsilyl)ethoxy]methyl}-1H-benzimidazol-2-yl)-1,3-benzoxazol-6-yl]pyridin-3-amine. LCMS for $C_{21}H_{15}FN_5O_3S$ (M+H)+: calculated m/z=436.1. found 436.1 $^1$H NMR (400 MHz, MeOD) δ 9.37 (s, 1H), 9.03 (s, 1H), 8.71 (s, 1H), 8.68-8.59 (m, 3H), 8.59-8.55 (m, 1H), 8.38 (dd, J=8.3, 1.4 Hz, 1H), 8.19 (s, 2H), 8.06 (t, J=8.7 Hz, 2H).

Example 40 and Example 41

Examples 40 and 41 were synthesized according to the procedure of Example 39 and the data are listed in Table 2.

TABLE 2

| Ex | Name | R | MS [M + H]$^+$ | $^1$H NMR Spectrum |
|---|---|---|---|---|
| 40 | N-(5-(2-(1H-Imidazol-2-yl)benzo[d]oxazol-6-yl)pyridin-3-yl)ethanesulfonamide | 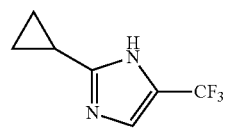 | calc: 370.1 found: 370.1 | $^1$H NMR (400 MHz, MeOD) δ 9.32 (s, 1H), 9.16 (s, 1H), 8.78 (s, 1H), 8.66 (t, J = 2.1 Hz, 1H), 8.63 (d, J = 8.3 Hz, 1H), 8.47 (d, J = 8.3 Hz, 1H), 8.12 (s, 2H), 3.92 (q, J = 7.3 Hz, 2H), 2.05 (t, J = 7.4 Hz, 3H) |
| 41 | N'-{5-[2-(1H-Imidazol-2-yl)-1,3-benzoxazol-6-yl]pyridin-3-yl}-N,N-dimethylsulfamide | | calc: 385.1 found: 385.1 | $^1$H NMR (400 MHz, MeOD) δ 9.35 (s, 1H), 9.18 (s, 1H), 8.75 (d, J = 1.3 Hz, 1H), 8.67-8.59 (m, 2H), 8.45 (dd, J = 8.3, 1.6 Hz, 1H), 8.12 (s, 2H), 3.56 (s, 6H). |

Example 42

2-(2-Cyclopropyl-1H-imidazol-5-yl)-6-(5-methoxypyridin-3-yl)benzo[d]oxazole

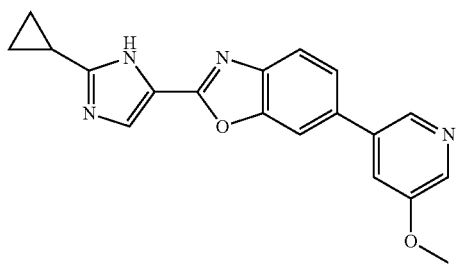 [SMILES: COc1cncc(-c2ccc3nc(-c4cnc(C5CC5)[nH]4)oc3c2)c1]

Step 1. 2-Cyclopropyl-5-(trifluoromethyl)-1H-imidazole

A suspension of 3,3-dibromo-1,1,1-trifluoroacetone [Alfa Aesar, L10826] (0.4 g, 1 mmol) in water (2 mL) was added sodium acetate (0.266 g, 3.24 mmol). The mixture was heated to 100° C. for 30 min. A solution of cyclopropanecarboxaldehyde (0.129 mL, 1.73 mmol) in methanol (0.8 mL) was added to the reaction mixture at room temperature, followed by 5.0 M ammonium hydroxide in water (0.56 mL, 2.8 mmol). The reaction was stirred at room temperature overnight. The crude mixture was directly used in the next step without purification.

Step 2. 2-(2-Cyclopropyl-1H-imidazol-5-yl)-6-(5-methoxypyridin-3-yl)benzo[d]oxazole To a mixture of 2-amino-5-(5-methoxypyridin-3-yl)phenol (20 mg, 0.09 mmol) and 2-cyclopropyl-5-(trifluoromethyl)-1H-imidazole (0.018 g, 0.10 mmol), 1.0 M sodium hydroxide (0.4 mL, 0.4 mmol) was added. The resulting dark suspension was heated to 90° C. for 4 h. After cooling to room temperature, the reaction mixture was diluted with methanol (4 mL). The resulting solution was filtered and the filtrate was purified by prep HPLC on a C-18 column eluting with a water: acetonitrile gradient buffered at pH 10 with 0.1% ammonium hydroxide, to afford the title compound (0.003, 10%). LCMS for $C_{19}H_{17}N_4O_2$ (M+H)$^+$: calculated m/z=333.1. found 333.2.

Examples 43 to 45

Examples 43 to 45 were synthesized according to the procedure of Example 42 and the data are listed in Table 3.

TABLE 3

R¹ group attached to core structure (imidazole-benzoxazole-pyridine with methoxy):

| Ex | Name | R¹ | MS [M + H]⁺ | ¹H NMR Spectrum |
|---|---|---|---|---|
| 43 | 6-(5-Methoxy-pyridin-3-yl)-2-(2-(tetrahydro-furan-3-yl)-1H-imidazol-5-yl)benzo[d]oxazole | (tetrahydrofuran-3-yl group) | Calc: 363.1; found: 363.2 | |
| 44 | 6-(5-Methoxy-pyridin-3-yl)-2-(2-phenyl-1H-imidazol-5-yl)benzo[d]oxazole | (phenyl group) | Calc: 369.1; found: 369.1 | ¹H NMR (400 MHz, MeOD) δ 8.75 (s, 1H), 8.49 (d, J = 2.5 Hz, 1H), 8.31-8.25 (m, 1H), 8.15 (d, J = 1.3 Hz, 1H), 8.03 (dd, J = 8.0, 1.5 Hz, 1H), 7.90 (d, J = 8.3 Hz, 1H), 7.84 (dd, J = 8.3, 1.7 Hz, 1H), 7.60-7.51 (m, 2H), 7.37-7.29 (m, 3H), 4.10 (s, 3H). |
| 45 | 2-(2-Ethyl-1H-imidazol-5-yl)-6-(5-methoxy-pyridin-3-yl)benzo[d]oxazole | (ethyl group) | Calc: 321.1; found: 321.1 | ¹H NMR (400 MHz, MeOD) δ 8.68 (d, J = 1.6 Hz, 1H), 8.46 (d, J = 2.6 Hz, 1H), 8.15 (dd, J = 5.0, 1.9 Hz, 2H), 7.98 (s, 1H), 7.94 (d, J = 8.3 Hz, 1H), 7.85 (dd, J = 8.4, 1.7 Hz, 1H), 4.07 (s, 3H), 3.08 (d, J = 7.7 Hz, 2H), 1.46 (t, J = 7.7 Hz, 3H) |

Example 46

6-(5-Methoxypyridin-3-yl)-2-(3-methyl-1H-pyrazol-5-yl)benzo[d]oxazole

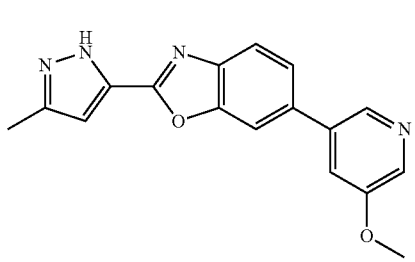

To a mixture of 2-amino-5-(5-methoxypyridin-3-yl)phenol (20 mg, 0.092 mmol) and 3-methyl-5-(trifluoromethyl)-1H-pyrazole [Aldrich, 424153] (15 mg, 0.10 mmol) was added 1.0 M sodium hydroxide in water (1 mL, 1 mmol). The resulting dark suspension was heated to 90° C. for 5 h. After cooling to room temperature, the mixture was diluted with methanol (4 mL) and purified by prep HPLC on a C-18 column eluting with a water: acetonitrile gradient buffered at pH 10 with 0.1% ammonium hydroxide, to afford the title compound as a white amorphous solid (7 mg, 20%). LCMS for $C_{17}H_{15}O_2N_4$ (M+H)⁺: calculated m/z=307.1. found 307.1 ¹H NMR (400 MHz, MeOD) δ 8.64 (s, 1H), 8.40 (d, J=2.6 Hz, 1H), 8.09 (d, J=13.3 Hz, 2H), 7.87 (d, J=8.3 Hz, 1H), 7.80 (dd, J=8.3, 1.7 Hz, 1H), 6.84 (s, 1H), 4.06 (s, 3H), 2.42 (s, 3H).

Example 47

6-(5-Methoxypyridin-3-yl)-2-(3-phenyl-1H-pyrazol-5-yl)benzo[d]oxazole

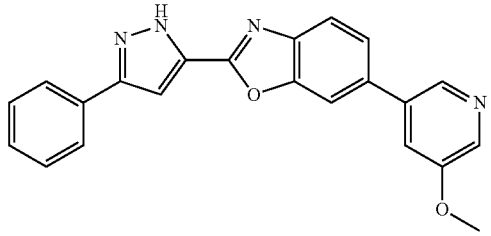 [SMILES: COc1cncc(-c2ccc3nc(-c4cc(-c5ccccc5)n[nH]4)oc3c2)c1]

The title compound was synthesized according to an experimental procedure analogous to Example 46, substituting 3-phenyl-5-(trifluoromethyl)-1H-pyrazole [TCI America, P1756] for 3-methyl-5-(trifluoromethyl)-1H-pyrazole. LCMS for $C_{22}H_{17}O_2N_4$ (M+H)⁺: calculated m/z=369.1. found 369.1 ¹H NMR (400 MHz, DMSO) δ 8.61 (d, J=1.7 Hz, 1H), 8.33 (d, J=2.7 Hz, 1H), 8.24 (d, J=1.2 Hz, 1H), 7.97-7.86 (m, 2H), 7.87-7.77 (m, 2H), 7.77-7.71 (m, 1H), 7.49 (q, J=8.5, 8.0 Hz, 3H), 7.17 (s, 1H), 3.95 (s, 3H).

Example 48

2-(1H-Benzimidazol-2-yl)-6-(1-benzyl-1H-pyrazol-4-yl)-1,3-benzoxazole

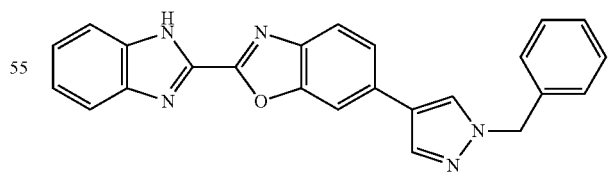

To a 1-dram vial was added 6-bromo-2-(1-((2-(trimethylsilyl)ethoxy)methyl)-1H-benzo[d]imidazol-2-yl)benzo[d]oxazole (20 mg, 0.045 mmol), 1-benzyl-4-(4,4,5,5-tetramethyl-1,3,2-dioxaborolan-2-yl)-1H-pyrazole (26 mg, 0.090 mmol) [Combi-Blocks, PN-8624], 1-butanol (0.32 mL), and CsF (32 mg, 0.21 mmol) in H₂O (60 µL). The mixture was degassed by bubbling with nitrogen for 5 min. Then bis(ditert-butyl(4-dimethylaminophenyl)phosphine)dichloropalladium(II) (1 mg, 0.001 mmol) [Sigma-Aldrich, 678740] was added, and the mixture degassed for an additional 5 min. The vial was capped, and the mixture was heated at 100° C. for 1.5 h. The reaction mixture was diluted with EtOAc/DCM and washed with water and then brine. The organic layer was filtered through a plug of $Na_2SO_4$ and concentrated. The resulting residue was dissolved in DCM (0.8 mL) and TFA (0.8 mL). The reaction mixture was stirred at 40° C. for 1 h and then concentrated. To the resulting residue was added 10% $NH_4OH$ (aq) (0.8 mL), and the reaction mixture was stirred for 30 min. Purification via preparative HPLC on a C-18 column (pH 10, eluting 30-50% water (0.1% $NH_4OH$)/MeCN over 5 min, 60 mL/min) afforded a white solid (9.9 mg, 56%). LCMS for $C_{24}H_{18}N_5O$ (M+H)$^+$: calculated m/z=392.1. found 392.2.

Example 49

2-(1H-Benzimidazol-2-yl)-6-(1H-indazol-5-yl)-1,3-benzoxazole

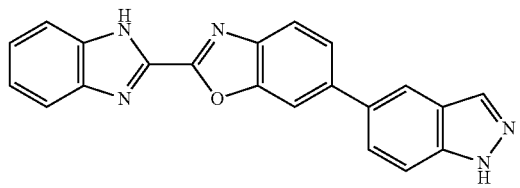 [SMILES: c1ccc2[nH]c(-c3nc4ccc(-c5ccc6[nH]ncc6c5)cc4o3)nc2c1]

The title compound was synthesized according to an experimental procedure analogous to the synthesis of Example 48, substituting 1H-indazol-5-ylboronic acid for 1-benzyl-4-(4,4,5,5-tetramethyl-1,3,2-dioxaborolan-2-yl)-1H-pyrazole. LCMS for $C_{21}H_{14}N_5O$ (M+H)$^+$: calculated m/z=352.1. found 352.1.

Example 50

2-(1H-Benzimidazol-2-yl)-6-(3-methyl-1H-indazol-5-yl)-1,3-benzoxazole

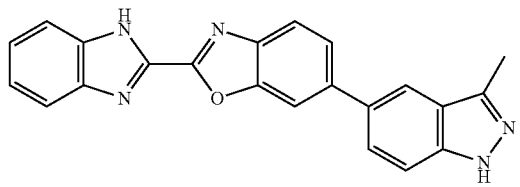 [SMILES: Cc1n[nH]c2ccc(-c3ccc4nc(-c5nc6ccccc6[nH]5)oc4c3)cc12]

The title compound was synthesized according to an experimental procedure analogous to the synthesis of Example 48, substituting (3-methyl-1H-indazol-5-yl)boronic acid for 1-benzyl-4-(4,4,5,5-tetramethyl-1,3,2-dioxaborolan-2-yl)-1H-pyrazole. $^1$H NMR (400 MHz, d$_6$-DMSO) δ 13.85 (s, 1H), 12.72 (s, 1H), 8.22 (d, J=1.1 Hz 1H), 8.13 (s, 1H), 7.97 (d, J=8.3 Hz, 1H), 7.88 (dd, J=8.4, 1.6 Hz, 1H), 7.78 (dd, J=8.7, 1.5 Hz, 1H), 7.71 (br s, 2H), 7.58 (d, J=8.6 Hz, 1H), 7.39-7.25 (m, 2H), 2.58 (s, 3H). LCMS for $C_{22}H_{16}N_5O$ (M+H)$^+$: calculated m/z=366.1. found 366.2.

Example 51

2-(1H-Benzimidazol-2-yl)-6-(3,4-difluorophenyl)-1,3-benzoxazole trifluoroacetate

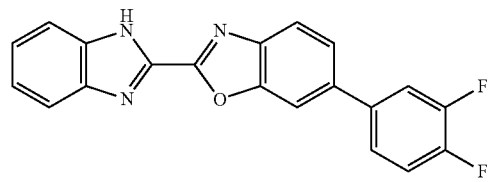 [SMILES: Fc1ccc(-c2ccc3nc(-c4nc5ccccc5[nH]4)oc3c2)cc1F]

To a 1-dram vial was added 6-bromo-2-(1-((2-(trimethylsilyl)ethoxy)methyl)-1H-benzo[d]imidazol-2-yl)benzo[d]oxazole (15 mg, 0.034 mmol), (3,4-difluorophenyl)boronic acid (14 mg, 0.089 mmol), 1-butanol (0.24 mL), and CsF (24 mg, 0.16 mmol) in $H_2O$ (50 µL). The mixture was degassed by bubbling with nitrogen for 5 min. Then bis(di-tert-butyl (4-dimethylaminophenyl)phosphine)dichloropalladium(II) (1 mg, 0.001 mmol) [Sigma-Aldrich, 678740] was added, and the mixture degassed for an additional 5 min. The vial was capped, and the mixture was heated at 100° C. for 1.5 h. The reaction mixture was diluted with EtOAc and washed with water and then brine. The organic layer was filtered through a plug of $Na_2SO_4$ and concentrated. The resulting residue was dissolved in DCM (0.6 mL) and TFA (0.6 mL). The reaction mixture was stirred at 40° C. for 1 h and then concentrated. Purification via preparative HPLC on a C-18 column (pH 2, eluting 45-65% water (0.1% TFA)/MeCN over 5 min, 60 mL/min) afforded a light yellow solid (5.3 mg, 34%). $^1$H NMR (400 MHz, d$_6$-DMSO) δ 13.89 (s, 1H), 8.27 (s, 1H), 8.04-7.91 (m, 2H), 7.89-7.76 (m, 2H), 7.76-7.67 (m, 1H), 7.67-7.51 (m, 2H), 7.37 (br s, 2H), 6.52 (s, 1H). $^{19}$F NMR (376 MHz, d$_6$-DMSO) δ −73.4 (s), −138.0 (d, J=22.4 Hz), −140.3 (d, J=22.4 Hz). LCMS for $C_{20}H_{12}F_2N_3O$ (M+H)$^+$: calculated m/z=348.1. found 348.1.

Example 52

6-[1-(Ethylsulfonyl)-1H-indazol-6-yl]-2-(1H-benzimidazol-2-yl)-1,3-benzoxazole

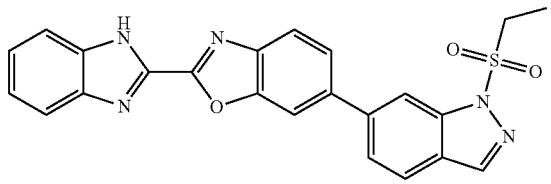 [SMILES: CCS(=O)(=O)n1ncc2ccc(-c3ccc4nc(-c5nc6ccccc6[nH]5)oc4c3)cc21]

Step 1. 6-(1H-Indazol-6-yl)-2-(1-{[2-(trimethylsilyl)ethoxy]methyl}-1H-benzimidazol-2-yl)-1,3-benzoxazole

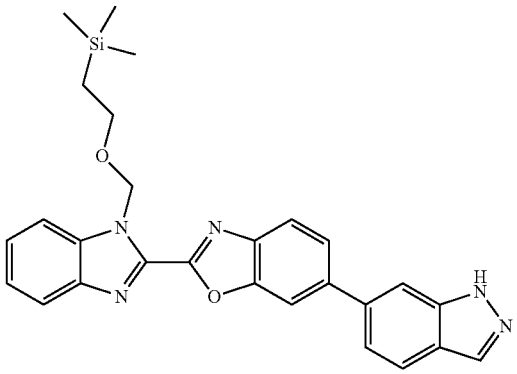 [SMILES: C[Si](C)(C)CCOCn1c(-c2nc3ccc(-c4ccc5cn[nH]c5c4)cc3o2)nc2ccccc21]

To a 1-dram vial was added 6-bromo-2-(1-((2-(trimethylsilyl)ethoxy)methyl)-1H-benzo[d]imidazol-2-yl)benzo[d]oxazole (0.20 g, 0.45 mmol), 1H-indazol-6-ylboronic acid (0.11 g, 0.68 mmol), 1-butanol (3.2 mL), and CsF (0.32 g, 2.1 mmol) in H$_2$O (0.6 mL). The mixture was degassed by bubbling with nitrogen for 5 min. Then bis(di-tert-butyl(4-dimethylaminophenyl)phosphine)dichloropalladium(II) (10 mg, 0.01 mmol) [Sigma-Aldrich, 678740] was added, and the solvent degassed for an additional 5 min. The vial was capped, and the mixture was heated at 100° C. for 1.5 h. The reaction mixture was diluted with EtOAc/DCM and washed with water and then brine. The organic layer was then dried over Na$_2$SO$_4$, filtered, and concentrated. Purification via column chromatography (1-15% MeOH in DCM) afforded a light orange solid (0.12 g, 55%). LCMS for C$_{27}$H$_{28}$N$_5$O$_2$Si (M+H)$^+$: calculated m/z=482.2. found 482.1.

Step 2. 6-[1-(Ethylsulfonyl)-1H-indazol-6-yl]-2-(1H-benzimidazol-2-yl)-1,3-benzoxazole To a suspension of 6-(1H-indazol-6-yl)-2-(1-{[2-(trimethylsilyl)ethoxy]methyl}-1H-benzimidazol-2-yl)-1,3-benzoxazole (20 mg, 0.042 mmol) in DMF (0.50 mL) at 0° C. was added NaH (5 mg, 0.1 mmol, 60% w/w in mineral oil). The reaction mixture was stirred for 30 min at 0° C. Ethanesulfonyl chloride (5.5 µL, 0.058 mmol) was added. The reaction mixture was then allowed to come to room temperature, stirring for 5 h. The reaction mixture was again cooled to 0° C., and the reaction was quenched with water. The resulting mixture was extracted with EtOAc (3×) and the combined organic layers were washed with water and then brine. The organic layer was then dried over Na$_2$SO$_4$, filtered, and concentrated. The resulting residue was dissolved in DCM (0.7 mL) and TFA (0.7 mL). The reaction mixture was heated to 40° C. for 1 h and then concentrated. To the resulting residue, 10% NH$_4$OH (aq) (0.7 mL) was added, and the reaction mixture was stirred for 30 min at room temperature. Purification via preparative HPLC on a C-18 column (pH 10, eluting 34-49% water (0.1% NH$_4$OH)/MeCN over 5 min, 60 mL/min) afforded a white solid (9.4 mg, 51%). $^1$H NMR (500 MHz, d$_6$-DMSO) δ 8.67 (d, J=0.7 Hz, 1H), 8.29 (d, J=1.4 Hz, 1H), 8.26 (s, 1H), 8.08 (d, J=8.5 Hz, 1H), 8.03 (d, J=8.3 Hz, 1H), 7.87 (dt, J=8.4, 1.6 Hz, 2H), 7.73-7.69 (m, 2H), 7.35-7.30 (m, 2H), 3.75 (q, J=7.3 Hz, 2H), 1.10 (t, J=7.3 Hz, 3H). LCMS for C$_{23}$H$_{18}$N$_5$O$_3$S (M+H)$^+$: calculated m/z=444.1. found 444.1.

Examples 53 and 54

2-(1H-Benzimidazol-2-yl)-6-(2-ethyl-2H-indazol-6-yl)-1,3-benzoxazole bis(trifluoroacetate) and 2-(1H-Benzimidazol-2-yl)-6-(1-ethyl-1H-indazol-6-yl)-1,3-benzoxazole bis(trifluoroacetate)

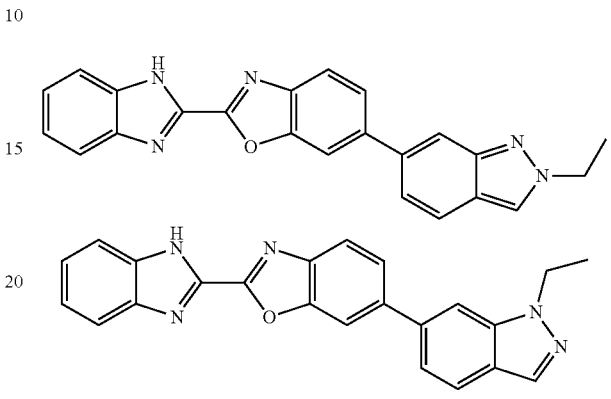

A suspension of 6-(1H-indazol-6-yl)-2-(1-{[2-(trimethylsilyl)ethoxy]methyl}-1H-benzimidazol-2-yl)-1,3-benzoxazole (20 mg, 0.042 mmol) and Cs$_2$CO$_3$ (29 mg, 0.089 mmol) in DMF (0.6 mL) was stirred at room temperature for 15 minutes. Iodoethane (6.6 µL, 0.083 mmol) was added, and the reaction mixture was stirred at room temperature for 4 h. The reaction mixture was diluted with EtOAc, and the organic layer was washed with water and then brine. The resulting organic layer was separated, filtered through a plug of Na$_2$SO$_4$, and concentrated. The resulting residue was dissolved in DCM (0.7 mL) and TFA (0.7 mL). The reaction mixture was stirred at 40° C. for 1 h and then concentrated. Purification via preparative HPLC on a C-18 column (pH 2, eluting 38-60% water (0.1% NH$_4$OH)/MeCN over 5 min, 60 mL/min) afforded 2-(1H-benzimidazol-2-yl)-6-(2-ethyl-2H-indazol-6-yl)-1,3-benzoxazole bis(trifluoroacetate) (Example 53) as a white solid (3.5 mg, 14%, first eluting peak, t=4.12 min) and 2-(1H-benzimidazol-2-yl)-6-(1-ethyl-1H-indazol-6-yl)-1,3-benzoxazole bis(trifluoroacetate) (Example 54) as a white solid (4.8 mg, 19%, second eluting peak, t=5.62 min). Example 53: LCMS for C$_{23}$H$_{18}$N$_5$O (M+H)$^+$: calculated m/z=380.1. found 380.2. Example 54: $^1$H NMR (500 MHz, d$_6$-DMSO) δ 8.32 (d, J=1.3 Hz, 1H), 8.11 (s, 2H), 8.01 (d, J=8.3 Hz, 1H), 7.95 (dd, J=8.4, 1.6 Hz, 1H), 7.88 (d, J=8.4 Hz, 1H), 7.76-7.70 (m, 2H), 7.59 (dd, J=8.4, 1.2 Hz, 1H), 7.41-7.31 (m, 2H), 4.55 (q, J=7.2 Hz, 2H), 1.45 (t, J=7.2 Hz, 3H). LCMS for C$_{23}$H$_{18}$N$_5$O (M+H)$^-$: calculated m/z=380.1. found 380.2.

Example 55

2-(1H-Benzimidazol-2-yl)-6-(4-benzylpiperazin-1-yl)-1,3-benzoxazole tris(trifluoroacetate)

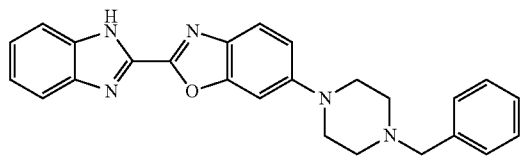 [SMILES: c1ccc(CN2CCN(c3ccc4nc(-c5nc6ccccc6[nH]5)oc4c3)CC2)cc1]

To a microwave vial charged with 6-bromo-2-(1-((2-(trimethylsilyl)ethoxy)methyl)-1H-benzo[d]imidazol-2-yl)benzo[d]oxazole (30 mg, 0.068 mmol) was added sequentially a mixture of methanesulfonato(2-dicyclohexylphosphino-2',6'-di-i-propoxy-1,1'-biphenyl)(2'-amino-1,1'-biphenyl-2-yl)palladium(II) (3 mg, 0.003 mmol) [Strem, 46-0314] and dicyclohexyl(2',6'-diisopropoxybiphenyl-2-yl)phosphine (2 mg, 0.003 mmol) in THF (0.150 mL), 1.0 M lithium hexamethyldisilazide in THF (0.230 mL, 0.23 mmol), and 1-benzylpiperazine (14 µL, 0.081 mmol). The reaction mixture was heated at 65° C. overnight. The reaction mixture was cooled to room temperature and diluted with DCM (1 mL). TFA (1 mL) was added. The reaction mixture was then stirred at 40° C. for 1 h before diluting with DCM and concentrating. Purification via preparative HPLC on a C-18 column (pH 2, eluting 19-39% water (0.1% TFA)/MeCN over 5 min, 60 mL/min) afforded a yellow-orange solid (5.7 mg, 10%). $^1$H NMR (400 MHz, CD$_3$OD) δ 7.81-7.69 (m, 3H), 7.63-7.51 (m, 5H), 7.47-7.36 (m, 3H), 7.24 (dd, J=8.9, 2.1 Hz, 1H), 4.46 (s, 2H), 3.96 (br s, 2H), 3.74-2.97 (m, 6H). LCMS for C$_{25}$H$_{24}$N$_5$O (M+H)$^+$: calculated m/z=410.2. found 410.1.

Example 56

5-[2-(1H-Benzimidazol-2-yl)-1,3-benzoxazol-6-yl]-3-(trifluoromethyl)pyridin-2-amine bis(trifluoroacetate)

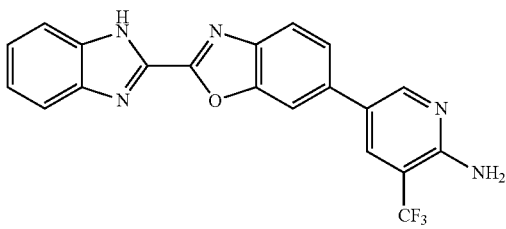 [SMILES: Nc1ncc(-c2ccc3nc(-c4nc5ccccc5[nH]4)oc3c2)cc1C(F)(F)F]

Step 1. 6-(4,4,5,5-Tetramethyl-1,3,2-dioxaborolan-2-yl)-2-(1-{[2-(trimethylsilyl)ethoxy]methyl}-1H-benzimidazol-2-yl)-1,3-benzoxazole

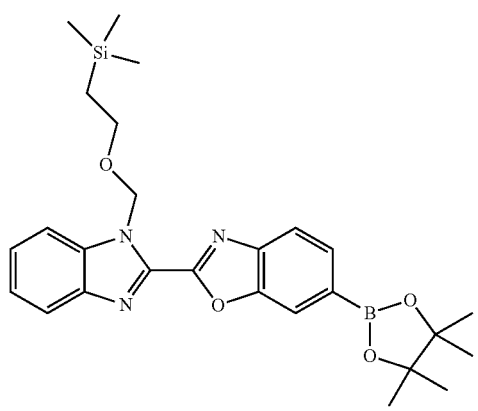 [SMILES: CC1(C)OB(c2ccc3nc(-c4nc5ccccc5n4COCC[Si](C)(C)C)oc3c2)OC1(C)C]

A 40-mL scintillation vial was charged with 6-bromo-2-(1-((2-(trimethylsilyl)ethoxy)methyl)-1H-benzo[d]imidazol-2-yl)benzo[d]oxazole (1.0 g, 2.2 mmol), bis(pinacolato)diboron (1.1 g, 4.5 mmol), dicyclohexyl(2',4',6'-triisopropylbiphenyl-2-yl)phosphine (0.11 g, 0.23 mmol), KOAc (0.51 g, 5.2 mmol), and tris(dibenzylideneacetone)dipalladium(0) (0.049 g, 0.054 mmol). 1,4-Dioxane (11 mL), which had been previously degassed with nitrogen for 15 min, was added, and the resulting mixture was degassed with nitrogen for an additional 5 min. The scintillation vial was capped and placed in a heating block at 80° C. for 3.5 h. The reaction mixture was filtered through Celite, and the filter cake was rinsed with EtOAc. The filtrate was washed with water and then brine, dried over Na$_2$SO$_4$, filtered, and concentrated. Purification via silica gel chromatography (1-40% EtOAc in hexanes [1% DCM]) afforded an orange foam (0.44 g, 35%). $^1$H NMR (400 MHz, CDCl$_3$) δ 8.10 (s, 1H), 7.96 (d, J=7.6 Hz, 1H), 7.88 (dd, J=8.0, 0.7 Hz, 1H), 7.82 (d, J=8.0 Hz, 1H), 7.67 (d, J=7.6 Hz, 1H), 7.50-7.32 (m, 2H), 6.41 (s, 2H), 3.79-3.50 (m, 2H), 1.38 (s, 12H), 1.03-0.84 (m, 2H), −0.13 (s, 9H). LCMS for C$_{26}$H$_{35}$BN$_3$O$_4$Si (M+H)$^+$: calculated m/z=492.2. found 492.2.

Step 2. 5-[2-(1H-Benzimidazol-2-yl)-1,3-benzoxazol-6-yl]-3-(trifluoromethyl)pyridin-2-amine bis(trifluoroacetate)

To a 1-dram vial was added 6-(4,4,5,5-tetramethyl-1,3,2-dioxaborolan-2-yl)-2-(1-{[2-(trimethylsilyl)ethoxy]methyl}-1H-benzimidazol-2-yl)-1,3-benzoxazole (20 mg, 0.036 mmol), 5-bromo-3-(trifluoromethyl)pyridin-2-amine (14 mg, 0.058 mmol) [Matrix, 046779], CsF (22 mg, 0.14 mmol) in H$_2$O (80 µL), and 1-butanol (0.44 mL). The mixture was degassed by bubbling with nitrogen for 5 min. Then bis(di-tert-butyl(4-dimethylaminophenyl)phosphine)dichloropalladium(II) (1 mg, 0.001 mmol) [Sigma-Aldrich, 678740] was added, and the reaction mixture was degassed for an additional 5 min. The vial was capped, and the mixture was heated at 100° C. for 1.5 h. The reaction mixture was diluted with EtOAc and washed with water and then brine. The organic layer was dried over Na$_2$SO$_4$, filtered, and concentrated. The resulting residue was dissolved in DCM (0.7 mL) and TFA (0.7 mL). The reaction mixture was heated at 40° C. for 1 h and then concentrated. Purification via preparative HPLC on a C-18 column (pH 2, eluting 30-44% water (0.1% TFA)/MeCN over 5 min, 60 mL/min) afforded a light yellow solid (5.5 mg, 24%). $^1$H NMR (400 MHz, d$_6$-DMSO) δ 8.69 (d, J=2.1 Hz, 1H), 8.24 (d, J=1.3 Hz, 1H), 8.14 (d, J=2.0 Hz, 1H), 7.94 (d, J=8.4 Hz, 1H), 7.81 (dd, J=8.4, 1.5 Hz, 1H), 7.71 (s, 2H), 7.41-7.29 (m, 2H), 6.70 (br s, 2H). $^{19}$F NMR (376 MHz, d$_6$-DMSO) δ −62.7, −74.2. LCMS for C$_{20}$H$_{13}$F$_3$N$_5$O (M+H)$^-$: calculated m/z=396.1. found 396.1.

Example 57

6-[2-(1H-Benzimidazol-2-yl)-1,3-benzoxazol-6-yl]-1-ethyl-1H-pyrazolo[4,3-b]pyridine tris(trifluoroacetate)

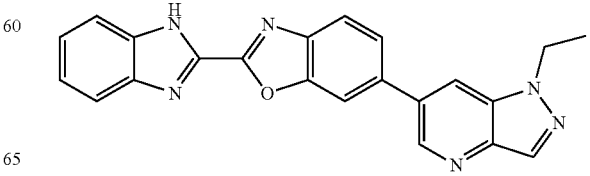

Step 1. 6-Bromo-1-ethyl-1H-pyrazolo[4,3-b]pyridine and 6-Bromo-2-ethyl-2H-pyrazolo[4,3-b]pyridine

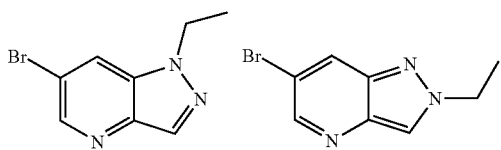

A suspension of 6-bromo-1H-pyrazolo[4,3-b]pyridine (0.202 g, 1.02 mmol) [PharmaBlock, PB00223] and $Cs_2CO_3$ (0.661 g, 2.03 mmol) in DMF (10 mL) was stirred for 15 min. Iodoethane (0.16 mL, 2.0 mmol) was added, and the reaction mixture was stirred at room temperature for 5 h. The reaction mixture was diluted with EtOAc and was washed with water and then brine. The organic layer was dried over $Na_2SO_4$, filtered, and concentrated. Purification via silica gel chromatography (2-20% EtOAc in DCM) afforded a mixture of the two title compounds (0.175 g, 76%). LCMS for $C_8H_9BrN_3$ (M+H)$^+$: calculated m/z=226.0, 228.0. found 226.1, 228.0 (first eluting peak) and 226.0, 228.1 (second eluting peak).

Step 2. 6-[2-(1H-Benzimidazol-2-yl)-1,3-benzoxazol-6-yl]-1-ethyl-1H-pyrazolo[4,3-b]pyridine tris(trifluoroacetate)

The title compound was synthesized according to an experimental procedure analogous to Example 56, Step 2 substituting a mixture of 6-bromo-1-ethyl-1H-pyrazolo[4,3-b]pyridine and 6-bromo-2-ethyl-2H-pyrazolo[4,3-b]pyridine for 5-bromo-3-(trifluoromethyl)pyridin-2-amine. $^1$H NMR (500 MHz, d$_6$-DMSO) δ 9.00 (d, J=1.9 Hz, 1H), 8.61 (dd, J=1.8, 0.9 Hz, 1H), 8.43-8.41 (m, 1H), 8.34 (d, J=0.9 Hz, 1H), 8.09-8.04 (m, 1H), 8.01 (dd, J=8.3, 1.7 Hz, 1H), 7.73 (br s, 2H), 7.40-7.33 (m, 2H), 4.58 (q, J=7.2 Hz, 2H), 1.48 (t, J=7.2 Hz, 3H). LCMS for $C_{22}H_{17}N_6O$ (M+H)$^+$: calculated m/z=381.1. found 381.1.

Example 58

1-({5-[2-(1H-Benzimidazol-2-yl)-1,3-benzoxazol-6-yl]pyridin-3-yl}sulfonyl)pyrrolidin-3-ol bis(trifluoroacetate)

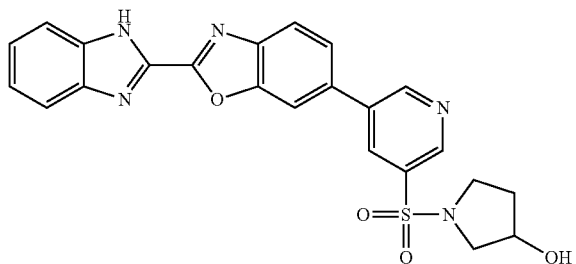 [SMILES: O=S(=O)(c1cncc(-c2ccc3nc(-c4nc5ccccc5[nH]4)oc3c2)c1)N1CCC(O)C1]

Step 1. 1-[(5-Bromopyridin-3-yl)sulfonyl]pyrrolidin-3-ol

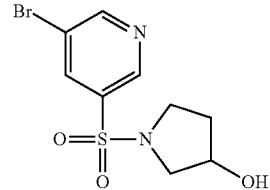 [SMILES: O=S(=O)(c1cncc(Br)c1)N1CCC(O)C1]

To a mixture of 3-pyrrolidinol (32 µL, 0.39 mmol) and triethylamine (50 µL, 0.4 mmol) in DCM (2.0 mL) at 0° C. was added 5-bromopyridine-3-sulfonyl chloride (50 mg, 0.19 mmol) [Combi-Blocks, ST-7824] in a single portion. The reaction mixture was stirred overnight while coming to room temperature. The reaction was quenched with sat. $NaHCO_3$ (2 mL). The organic layer was removed, and the aqueous layer was extracted with DCM (2×2 mL). The combined organic layers were dried over $Na_2SO_4$, filtered, and concentrated. Purification via silica gel chromatography (25-100% EtOAc in DCM) afforded a white solid (39.0 mg, 65%). LCMS for $C_9H_{12}BrN_2O_3S$ (M+H)$^+$: calculated m/z=307.0, 309.0. found 306.9, 308.9.

Step 2. 1-({5-[2-(1H-Benzimidazol-2-yl)-1,3-benzoxazol-6-yl]pyridin-3-yl}sulfonyl)pyrrolidin-3-ol bis(trifluoroacetate)

The title compound was synthesized according to an experimental procedure analogous to Example 56, Step 2 substituting 1-[(5-bromopyridin-3-yl)sulfonyl]pyrrolidin-3-ol for 5-bromo-3-(trifluoromethyl)pyridin-2-amine. $^1$H NMR (400 MHz, d$_6$-DMSO) δ 13.91 (br s, 1H), 9.32 (d, J=2.1 Hz, 1H), 9.00 (d, J=2.0 Hz, 1H), 8.50 (t, J=2.0 Hz 1H), 8.45 (s, 1H), 8.06 (d, J=8.3, 1.4 Hz, 1H), 7.97 (d, J=8.4 Hz, 1H), 7.82 (br s, 1H), 7.63 (br s, 1H), 7.37 (br s, 2H), 4.91 (s, 1H), 4.21 (s, 1H), 3.50-3.37 (m, 2H), 3.29-3.14 (m, 2H), 1.91-1.78 (m, 1H), 1.76-1.63 (m, 1H). LCMS for $C_{23}H_{20}N_5O_4S$ (M+H)$^+$: calculated m/z=462.1. found 462.1.

Example 59

5-[2-(1H-Benzimidazol-2-yl)-1,3-benzoxazol-6-yl]-N-ethylpyridine-3-sulfonamide bis(trifluoroacetate)

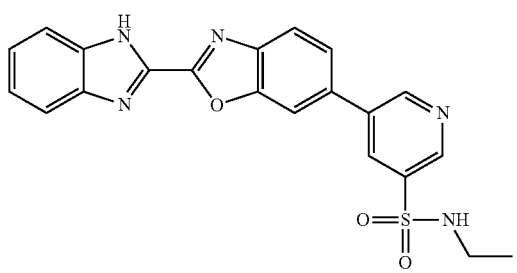 [SMILES: CCNS(=O)(=O)c1cncc(-c2ccc3nc(-c4nc5ccccc5[nH]4)oc3c2)c1]

The title compound was synthesized according to an experimental procedure analogous to Example 58, substituting ethylamine (2.0 M in THF) for 3-pyrrolidinol in Step 1 and substituting 5-bromo-N-ethylpyridine-3-sulfonamide for 5-bromo-3-(trifluoromethyl)pyridin-2-amine in step 2. LCMS for $C_{21}H_{18}N_5O_3S$ (M+H)$^+$: calculated m/z=420.1. found 420.1.

Example 60

N-{5-[2-(1H-Benzimidazol-2-yl)-1,3-benzoxazol-6-yl]-2-fluorophenyl}ethanesulfonamide

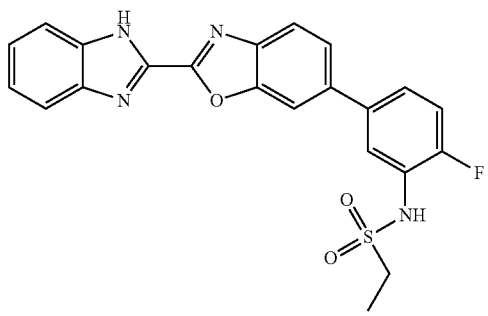 [SMILES: CCS(=O)(=O)Nc1cc(-c2ccc3nc(-c4nc5ccccc5[nH]4)oc3c2)ccc1F]

Step 1. 2-Fluoro-5-[2-(1-{[2-(trimethylsilyl)ethoxy]methyl}-1H-benzimidazol-2-yl)-1,3-benzoxazol-6-yl]aniline

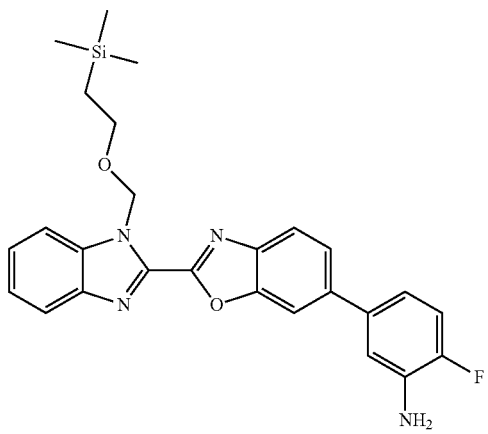 [SMILES: C[Si](C)(C)CCOCn1c(-c2nc3ccc(-c4ccc(F)c(N)c4)cc3o2)nc2ccccc21]

The title compound was synthesized according to an experimental procedure analogous to Example 17, Step 1 substituting 5-bromo-2-fluoroaniline for 5-bromopyridin-3-amine. $^1$H NMR (400 MHz, CDCl$_3$) δ 7.96 (d, J=7.5 Hz, 1H), 7.85 (d, J=8.3 Hz, 1H), 7.80 (d, J=1.4 Hz, 1H), 7.68 (d, J=7.7 Hz, 1H), 7.60 (dd, J=8.3, 1.6 Hz, 1H), 7.50-7.37 (m, 2H), 7.14-7.01 (m, 2H), 6.99-6.92 (m, 1H), 6.42 (s, 2H), 3.86 (s, 2H), 3.72-3.66 (m, 2H), 1.03-0.84 (m, 2H), −0.11 (s, 9H). LCMS for $C_{26}H_{28}FN_4O_2Si$ (M+H)$^+$: calculated m/z=475.2. found 475.2.

Step 2. N-{5-[2-(1H-Benzimidazol-2-yl)-1,3-benzoxazol-6-yl]-2-fluorophenyl}ethanesulfonamide To the solution of 2-fluoro-5-[2-(1-{[2-(trimethylsilyl)ethoxy]methyl}-1H-benzimidazol-2-yl)-1,3-benzoxazol-6-yl]aniline (15 mg, 0.032 mmol) in 4:1 DCM/pyridine (0.200 mL) at 0° C. was added ethanesulfonyl chloride (4.5 µL, 0.047 mmol). The reaction mixture was stirred for 30 min and then allowed to come to room temperature, stirring for 1.5 h. The reaction mixture was then concentrated. The resulting residue was dissolved in DCM (0.6 mL) and TFA (0.6 mL), and the reaction mixture was stirred at 40° C. for 1 h. The reaction mixture was then concentrated. To the resulting residue was added 10% NH$_4$OH (aq) (0.6 mL). The reaction mixture was stirred for 20 min at room temperature and then stored at 0° C. for 2.5 days. Purification via preparative HPLC on a C-18 column (pH 10, eluting 18-38% water (0.1% NH$_4$OH)/MeCN over 5 min, 60 mL/min) afforded an off-white solid (6.9 mg, 50%). $^1$H NMR (400 MHz, d$_6$-DMSO) δ 8.12 (s, 1H), 7.98 (d, J=8.5 Hz, 1H), 7.81-7.66 (m, 4H), 7.49 (br s, 1H), 7.41-7.30 (m, 3H), 3.10 (q, J=7.3 Hz, 2H), 1.27 (t, J=7.2 Hz, 3H). LCMS for $C_{22}H_{18}FN_4O_3S$ (M+H)$^+$: calculated m/z=437.1. found 437.1.

Example 61

1-(5-(2-(1H-Imidazol-2-yl)benzo[d]oxazol-6-yl)pyridin-3-yl)-2,2,2-trifluoroethanol bis(trifluoroacetate)

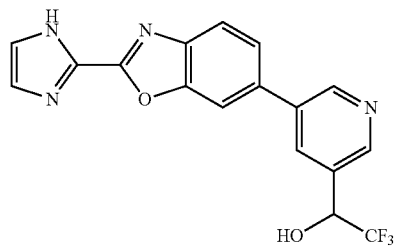 [SMILES: OC(c1cncc(-c2ccc3nc(-c4ncc[nH]4)oc3c2)c1)C(F)(F)F]

Step 1. 1-(5-bromopyridin-3-yl)-2,2,2-trifluoroethanol

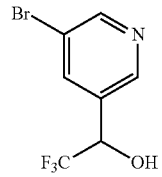 [SMILES: OC(c1cncc(Br)c1)C(F)(F)F]

A 100 mL round bottom flask was charged with 5-bromonicotinaldehyde [Aldrich, 396280] (3 g, 20 mmol), 2.0 M (trifluoromethyl)trimethylsilane in tetrahydrofuran [Aldrich, 288712] (11 mL, 22 mmol) in tetrahydrofuran (30 mL). To the solution was added 1.0 M tetra-n-butylammonium fluoride in tetrahydrofuran [Aldrich, 216142] (2 mL, 2 mmol) dropwise at 5° C. The resultant pale brown reaction mixture was stirred at room temperature for 2 h. The reaction was quenched with 1N HCl. The mixture was neutralized by sodium bicarbonate and extracted with ethyl acetate (2×30 mL). The organic phase was washed with brine, dried over sodium sulfate, filtered and concentrated under vacuum to afford the desired product as pale yellow solid (4.0 g, 100%). LCMS for $C_7H_6BrF_3NO$ (M+H)$^+$: calculated m/z=256.0, 258.0. found 256.0, 258.0.

Step 2. 1-(5-(2-(1H-Imidazol-2-yl)benzo[d]oxazol-6-yl)pyridin-3-yl)-2,2,2-trifluoroethanol A 10 mL microwave vial was charged with bis(pinacolato)diboron [Aldrich, 473294] (0.082 g, 0.32 mmol), 1-(5- bromopyridin-3-yl)-2,2,2-trifluoroethanol (0.082 g, 0.32 mmol), and potassium acetate (0.11 g, 1.1 mmol) in 1,4-dioxane (4 mL). The mixture was degassed by nitrogen for 5 min, then charged with [1,1'-bis(diphenylphosphino)ferrocene]dichloropalladium(II), complex with dichloromethane (1:1) [Aldrich, 685127] (22 mg, 0.026 mmol). The resultant mixture was heated for 2 h at 120° C. The crude mixture was filtered through Celite concentrated under vacuum.

A 25 mL round bottom flask was charged with the mixture generated from the residue from the previous reaction in 1,4-dioxane (2.6 mL), 6-bromo-2-(1H-imidazol-2-yl)-1,3-benzoxazole (0.057 g, 0.23 mmol), sodium carbonate (91 mg, 0.85 mmol), and water (1 mL). The mixture was degassed and then heated with a microwave at 110° C. for 1.5 h. The reaction mixture was cooled to room temperature and then diluted with methanol (5 mL). The suspension was filtered through Celite, and the filtrate was concentrated under vacuum. The resultant residue was purified by prep HPLC on a C-18 column eluting with water:acetonitrile gradient buffered at pH 2 with 0.1% trifluoroacetic acid to afford the title compound as a light yellow solid (60 mg, 40%). LCMS for $C_{17}H_{12}F_3N_4O_2$ $(M+H)^+$: calculated m/z=361.1. found 361.1.

Example 62

2-(4,5-Dimethyl-1H-imidazol-2-yl)-6-(5-(methylsulfonyl)pyridin-3-yl)benzo[d]oxazole bis(trifluoroacetate)

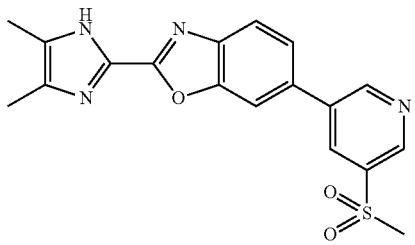

Step 1. 6-Bromo-2-methylbenzo[d]oxazole

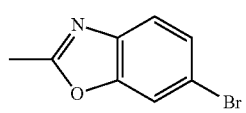

The title compound was synthesized according to an experimental procedure analogous to Example 8, Step 1, substituting 2-amino-5-bromophenol for 2-amino-5-(5-methoxypyridin-3-yl)phenol. LCMS for $C_8H_7BrNO$ $(M+H)^+$: calculated m/z=212.0, 214.0. found 212.0, 214.0.

Step 2. 2-Methyl-6-(5-(methylsulfonyl)pyridin-3-yl)benzo[d]oxazole

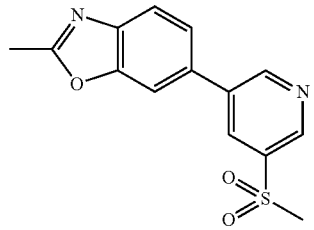

The title compound was synthesized according to an experimental procedure analogous to Example 14, Step 3, substituting 3-bromo-5-(methylsulfonyl)pyridine [CombiBlocks, PY-7190] for 3-bromo-5-{[tert-butyl(dimethyl)silyl]oxy}pyridine. LCMS for $C_{14}H_{13}N_2O_3S$ $(M+H)^+$: calculated m/z=289.1. found 289.1.

Step 3. 6-(5-(Methylsulfonyl)pyridin-3-yl)benzo[d]oxazole-2-carbaldehyde

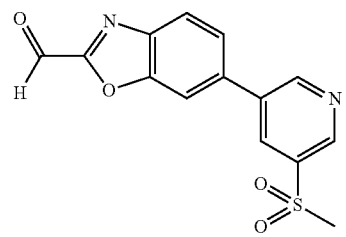 [SMILES: CS(=O)(=O)c1cncc(-c2ccc3nc(C=O)oc3c2)c1]

The title compound was synthesized according to an experimental procedure analogous to Example 6, Step 2, substituting 2-methyl-6-(5-(methylsulfonyl)pyridin-3-yl)benzo[d]oxazole for 6-(5-methoxypyridin-3-yl)-2-methyl-1,3-benzothiazole. LCMS for $C_{14}H_{13}N_2O_5S$ $(M+H_3O)^-$: calculated m/z=321.1. found 321.1.

Step 4. 2-(4,5-Dimethyl-1H-imidazol-2-yl)-6-(5-(methylsulfonyl)pyridin-3-yl)benzo[d]oxazole A 10 mL microwave vial was charged with 2,3-butanedione [Aldrich, B85307] (0.015 mL, 0.17 mmol), 6-(5-(methylsulfonyl)pyridin-3-yl)benzo[d]oxazole-2-carbaldehyde (0.053 g, 0.18 mmol) and ammonium acetate (0.06 g, 0.8 mmol) in acetic acid (0.5 mL, 9 mmol). The mixture was heated with a microwave at 160° C. for 15 min. The reaction was cooled to room temperature. After evaporation of the solvent by nitrogen, the resultant residue was purified by prep HPLC on a C-18 column eluting with water:acetonitrile gradient buffered at pH 2 with 0.1% trifluoroacetic acid to afford the title compound as a light yellow solid (10 mg, 16%). LCMS for $C_{18}H_{17}N_4O_3S$ $(M+H)^+$: calculated m/z=369.1. found 369.1.

Example 63

N-(5-(2-(4,5-Dimethyl-1H-imidazol-2-yl)benzo[d]oxazol-6-yl)pyridin-3-yl)ethanesulfonamide bis(trifluoroacetate)

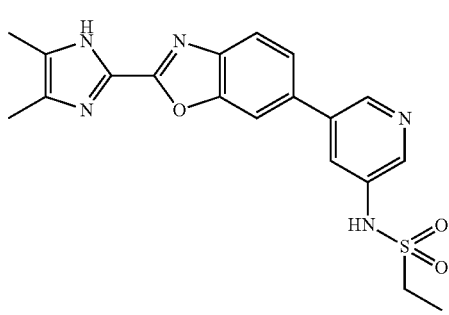 [SMILES: CCS(=O)(=O)Nc1cncc(-c2ccc3nc(-c4nc(C)c(C)[nH]4)oc3c2)c1]

Step 1.
5-(2-Methylbenzo[d]oxazol-6-yl)pyridin-3-amine

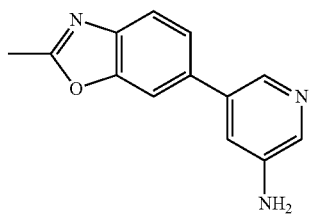 [SMILES: Cc1nc2ccc(-c3cncc(N)c3)cc2o1]

The title compound was synthesized according to an experimental procedure analogous to Example 17, Step 1, substituting 6-bromo-2-methylbenzo[d]oxazole for 6-bromo-2-(1-{[2-(trimethylsilyl)ethoxy]methyl}-1H-benzimidazol-2-yl)-1,3-benzoxazole. LCMS for $C_{13}H_{12}N_3O$ $(M+H)^-$: calculated m/z=226.1. found 226.1.

Step 2. N-(5-(2-Methylbenzo[d]oxazol-6-yl)pyridin-3-yl)ethanesulfonamide

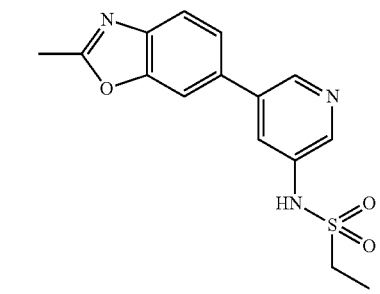 [SMILES: CCS(=O)(=O)Nc1cncc(-c2ccc3nc(C)oc3c2)c1]

The title compound was synthesized according to an experimental procedure analogous to Example 17, Step 2, substituting 5-(2-methylbenzo[d]oxazol-6-yl)pyridin-3-amine for 5-[2-(1-{[2-(trimethylsilyl)ethoxy]methyl}-1H-benzimidazol-2-yl)-1,3-benzoxazol-6-yl]pyridin-3-amine. LCMS for $C_{15}H_{16}N_3O_3S$ $(M+H)^+$: calculated m/z=318.1. found 318.1.

Step 3. N-(5-(2-Formylbenzo[d]oxazol-6-yl)pyridin-3-yl)ethanesulfonamide

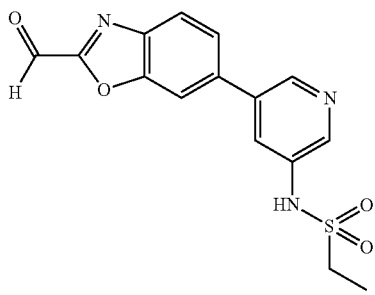 [SMILES: CCS(=O)(=O)Nc1cncc(-c2ccc3nc(C=O)oc3c2)c1]

The title compound was synthesized according to an experimental procedure analogous to Example 6, Step 2, substituting N-(5-(2-methylbenzo[d]oxazol-6-yl)pyridin-3-yl)ethanesulfonamide for 6-(5-methoxypyridin-3-yl)-2-methyl-1,3-benzothiazole. LCMS for $C_{15}H_{16}N_3O_5S$ $(M+H_3O)^+$: calculated m/z=350.1. found 350.1.

Step 4. N-(5-(2-(4,5-Dimethyl-1H-imidazol-2-yl)benzo[d]oxazol-6-yl)pyridin-3-yl)ethanesulfonamide The title compound was synthesized according to an experimental procedure analogous to Example 62, Step 4, substituting N-(5-(2-formylbenzo[d]oxazol-6-yl)pyridin-3-yl)ethanesulfonamide for 6-(5-(methylsulfonyl)pyridin-3-yl)benzo[d]oxazole-2-carbaldehyde. LCMS for $C_{19}H_{20}N_5O_3S$ $(M+H)^+$: calculated m/z=398.1. found 398.1.

Example 64

N-(5-(2-(5-Methyl-4-propyl-1H-imidazol-2-yl)benzo[d]oxazol-6-yl)pyridin-3-yl)ethanesulfonamide bis(trifluoroacetate)

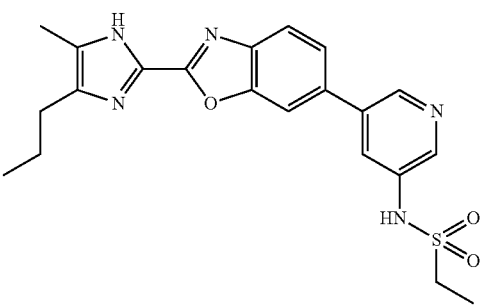 [SMILES: CCCc1nc(-c2nc3ccc(-c4cncc(NS(=O)(=O)CC)c4)cc3o2)[nH]c1C]

The title compound was synthesized according to an experimental procedure analogous to Example 62, Step 4, substituting 2,3-hexanedione [Aldrich, 144169] for 2,3-butanedione. LCMS for $C_{21}H_{24}N_5O_3S$ $(M+H)^+$: calculated m/z=426.2. found 426.2.

Example 65

N-(5-(2-(4,5-Dimethyl-1H-imidazol-2-yl)benzo[d]oxazol-6-yl)-2-methoxypyridin-3-yl)ethanesulfonamide bis(trifluoroacetate)

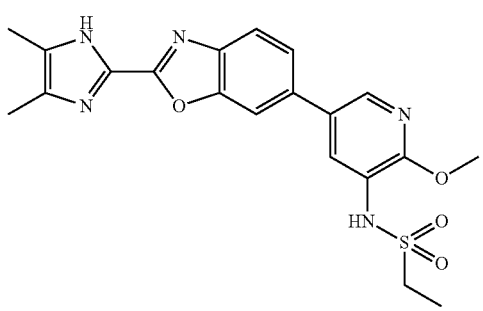

Step 1. 6-bromobenzo[d]oxazole-2-carbaldehyde

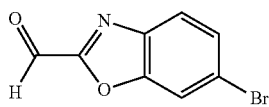 [SMILES: O=Cc1nc2ccc(Br)cc2o1]

The title compound was synthesized according to an experimental procedure analogous to Example 6, Step 2, substituting 6-bromo-2-methylbenzo[d]oxazole for 6-(5-methoxypyridin-3-yl)-2-methyl-1,3-benzothiazole. LCMS for $C_8H_7BrNO_3$ (M+H$_3$O)$^+$: calculated m/z=244.0, 246.0. found 244.0, 246.0.

Step 2. 6-Bromo-2-(4,5-dimethyl-1H-imidazol-2-yl)benzo[d]oxazole

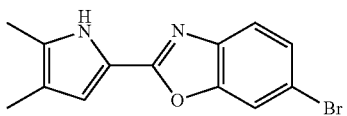 [SMILES: Cc1cc(-c2nc3ccc(Br)cc3o2)[nH]c1C]

The title compound was synthesized according to an experimental procedure analogous to Example 62, Step 4, substituting 6-bromobenzo[d]oxazole-2-carbaldehyde for 6-(5-(methylsulfonyl)pyridin-3-yl)benzo[d]oxazole-2-carbaldehyde LCMS for $C_{12}H_{11}BrN_3O$ (M+H)$^+$: calculated m/z=292.0, 294.0. found 292.0, 294.0.

Step 3. N-(5-Bromo-2-methoxypyridin-3-yl)ethanesulfonamide

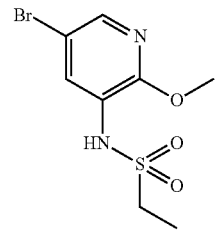

The title compound was synthesized according to an experimental procedure analogous to Example 17, Step 1, substituting 5-bromo-2-methoxypyridin-3-amine [Combi-Blocks, PY-1470] for 6-bromo-2-(1-{[2-(trimethylsilyl)ethoxy]methyl}-1H-benzimidazol-2-yl)-1,3-benzoxazole. LCMS for $C_8H_{12}BrN_2O_3S$ (M+H)$^+$: calculated m/z=295.0, 297.0. found 295.0, 297.0.

Step 4. N-(5-(2-(4,5-Dimethyl-1H-imidazol-2-yl)benzo[d]oxazol-6-yl)-2-methoxypyridin-3-yl)ethanesulfonamide The title compound was synthesized according to an experimental procedure analogous to Example 61, Step 2, substituting N-(5-bromo-2-methoxypyridin-3-yl)ethanesulfonamide for 1-(5-bromopyridin-3-yl)-2,2,2-trifluoroethanol, also substituting 6-bromo-2-(4,5-dimethyl-1H-imidazol-2-yl)benzo[d]oxazole for 6-bromo-2-(1H-imidazol-2-yl)-1,3-benzoxazole. LCMS for $C_{20}H_{22}N_5O_4S$ (M+H)+: calculated m/z=428.1. found 428.1.

Example 66

N-(2-Methoxy-5-(2-(4,5,6,7-tetrahydro-1H-benzo[d]imidazol-2-yl)benzo[d]oxazol-6-yl)pyridin-3-yl)ethanesulfonamide

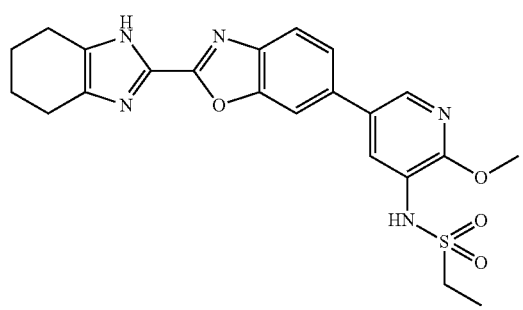 [SMILES: CCS(=O)(=O)Nc1cc(-c2ccc3nc(-c4nc5c([nH]4)CCCC5)oc3c2)cnc1OC]

The title compound was synthesized according to an experimental procedure analogous to Example 65, substituting 1,2-cyclohexanedione [Aldrich, C101400] for 2,3-butanedione. LCMS for $C_{22}H_{24}N_5O_4S$ (M+H)$^+$: calculated m/z=454.2. found 454.2.

Example 67

1-(5-(2-(4,5-Dimethyl-1H-imidazol-2-yl)benzo[d]oxazol-6-yl)pyridin-3-yl)-2,2,2-trifluoroethanol bis(trifluoroacetate)

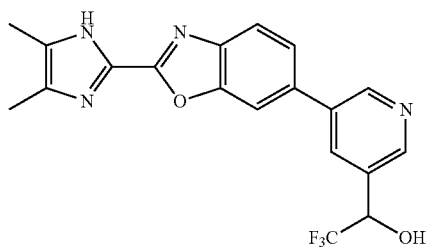 [SMILES: Cc1nc(-c2nc3ccc(-c4cncc(C(O)C(F)(F)F)c4)cc3o2)[nH]c1C]

The title compound was synthesized according to an experimental procedure analogous to Example 65, Step 4, substituting 2,2,2-trifluoro-1-(5-(4,4,5,5-tetramethyl-1,3,2-dioxaborolan-2-yl)pyridin-3-yl)ethanol for N-(2-methoxy-5-(4,4,5,5-tetramethyl-1,3,2-dioxaborolan-2-yl)pyridin-3-yl)ethanesulfonamide. LCMS for $C_{19}H_{16}F_3N_4O_2$ (M+H)$^+$: calculated m/z=389.1. found 389.1.

Example 68

2,2,2-Trifluoro-1-(5-(2-(4,5,6,7-tetrahydro-1H-benzo[d]imidazol-2-yl)benzo[d]oxazol-6-yl)pyridin-3-yl)ethanol

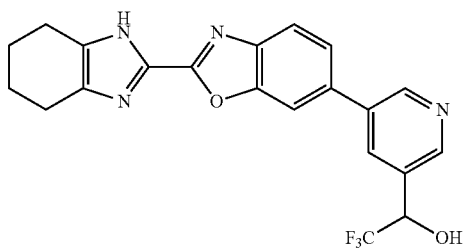 [SMILES: OC(c1cncc(-c2ccc3nc(-c4nc5c([nH]4)CCCC5)oc3c2)c1)C(F)(F)F]

The title compound was synthesized according to an experimental procedure analogous to Example 66, substituting 2,2,2-trifluoro-1-(5-(4,4,5,5-tetramethyl-1,3,2-dioxaborolan-2-yl)pyridin-3-yl)ethanol for N-(2-methoxy-5-(4,4,5,5-tetramethyl-1,3,2-dioxaborolan-2-yl)pyridin-3-yl)ethanesulfonamide. LCMS for $C_{21}H_{18}F_3N_4O_2$ (M+H)$^+$: calculated m/z=415.1. found 415.1.

Examples 69 to 74

Examples 69 to 74 were synthesized according to the procedure of Example 35 and the data are listed in Table 4.

TABLE 4

| Ex. No. | Name | R | MS [M + H]$^+$ |
|---|---|---|---|
| 69 | 2-(1H-Benzo[d]imidazol-2-yl)-6-(6-fluoro-5-methoxypyridin-3-yl)benzo[d]oxazole bis(trifluoroacetate) | 6-fluoro-5-methoxypyridin-3-yl | 361.1 |
| 70 | 2-(1H-Benzo[d]imidazol-2-yl)-6-(2-fluoropyrimidin-5-yl)benzo[d]oxazole bis(trifluoroacetate) | 2-fluoropyrimidin-5-yl | 332.1 |
| 71 | 2-(5-(2-(1H-Benzo[d]imidazol-2-yl)benzo[d]oxazol-6-yl)pyridin-3-yl)acetic acid | 5-(carboxymethyl)pyridin-3-yl | 371.1 |
| 72 | 2-(1H-Benzo[d]imidazol-2-yl)-6-(5-(dimethylphosphoryl)pyridin-3-yl)benzo[d]oxazole bis(trifluoroacetate) | 5-(dimethylphosphoryl)pyridin-3-yl | 389.1 |
| 73 | N-(5-(2-(1H-Benzo[d]imidazol-2-yl)benzo[d]oxazol-6-yl)pyridin-3-yl)-N-methylethanesulfonamide bis(trifluoroacetate) | 5-(N-methylethylsulfonamido)pyridin-3-yl | 434.1 |
| 74 | 1-(5-(2-(1H-Benzo[d]imidazol-2-yl)benzo[d]oxazol-6-yl)pyridin-3-yl)-2,2,2-trifluoroethanol bis(trifluoroacetate) | 5-(2,2,2-trifluoro-1-hydroxyethyl)pyridin-3-yl | 411.1 |

Examples 75 to 80

Examples 75 to 80 were synthesized according to the procedure of Example 17 and the data are listed in Table 5.

TABLE 5

| Ex. No. | Name | R | MS [M + H]⁺ |
|---|---|---|---|
| 75 | N-(5-(2-(1H-Benzo[d]imidazol-2-yl)benzo[d]oxazol-6-yl)-2-fluoropyridin-3-yl)-2,2,2-trifluoro-ethanesulfonamide bis(trifluoroacetate) | 2-fluoropyridin-3-yl with NHS(O)₂CH₂CF₃ | 492.1 |
| 76 | N-(5-(2-(1H-Benzo[d]imidazol-2-yl)benzo[d]oxazol-6-yl)-2-methylpyridin-3-yl)-2,2,2-trifluoro-ethanesulfonamide bis(trifluoroacetate) | 2-methylpyridin-3-yl with NHS(O)₂CH₂CF₃ | 488.1 |
| 77 | N-(5-(2-(1H-Benzo[d]imidazol-2-yl)benzo[d]oxazol-6-yl)pyridin-3-yl)-2,2,2-trifluoro-ethanesulfonamide bis(trifluoroacetate) | pyridin-3-yl with NHS(O)₂CH₂CF₃ | 474.1 |
| 78 | N-(2-(2-(1H-Benzo[d]imidazol-2-yl)benzo[d]oxazol-6-yl)-5-fluoropyridin-4-yl)ethanesulfonamide bis(trifluoroacetate) | 5-fluoropyridin-4-yl with NHS(O)₂CH₂CH₃ | 438.1 |
| 79 | N-(5-(2-(1H-Benzo[d]imidazol-2-yl)benzo[d]oxazol-6-yl)-2-methoxypyridin-3-yl)ethanesulfonamide bis(trifluoroacetate) | 2-methoxypyridin-3-yl with NHS(O)₂CH₂CH₃ | 450.1 |
| 80 | N-(5-(2-(1H-Benzo[d]imidazol-2-yl)benzo[d]oxazol-6-yl)-3-fluoro-2-methoxyphenyl)ethanesulfonamide bis(trifluoroacetate) | 3-fluoro-2-methoxyphenyl with NHS(O)₂CH₂CH₃ | 467.1 |

Example A

THP-1 RPS6 ELISA Assay

To measure the Phosphorylated Ribosomal Protein S6 (RPS6) in cell lysates, THP-1 cells (Human Acute Monocytic Leukemia) are purchased from ATCC (Manassas, Va.) and maintained in RPMI with 10% FBS (Gibco/Life Technologies, Carlsbad, Calif.). For the assay, THP-1 cells are serum starved overnight in RPMI, then plated in RPMI ($2 \times 10^5$ cells/well in 90 µL) into 96-well flat-bottom tissue culture treated plates (Corning, Corning, N.Y.), in the presence or absence of a concentration range of test compounds. Covered plates are incubated for 2 hours at 37° C., 5% $CO_2$ then treated with or without 10 nM MCP-1 (MYBioSource, San Diego, Calif.) for 15 minutes at 37° C., 5% $CO_2$. Plates are centrifuged at 1600 RPM and supernatants are removed. Cells are lysed in Lysis Buffer (Cell Signaling, Danvers, Mass.) with Protease Inhibitor (Calbiochem/EMD, Germany), PMSF (Sigma, St Louis Mo.), HALTS (Thermo Fisher, Rockford, Ill.) for 30 min on wet ice. Cell lysates are frozen at −80° C. before testing. The lysates are tested in the Human/Mouse/Rat Phospho-RPS6 ELISA (R&D Systems, Inc. Minn, Minn.). The plate is measured using a microplate reader (SpectraMax M5-Molecular Devices, LLC Sunnyvale, Calif.) set to 450 nm with a wavelength correction of 540. $IC_{50}$ determination is performed by fitting the curve of inhibitor percent inhibition versus the log of the inhibitor concentration using the GraphPad Prism 5.0 software.

Data for the Examples, obtained using the methods described in Example A, are provided in Table A.

TABLE A

| Example # | THP p-RPS6 ELISA $IC_{50}$ (nM) |
|---|---|
| 4 | ++ |
| 15 | ++ |
| 17 | + |
| 18 | +++ |
| 19 | ++ |
| 20 | ++ |
| 21 | + |
| 22 | + |
| 23 | + |
| 24 | +++ |

TABLE A-continued

| Example # | THP p-RPS6 ELISA IC$_{50}$ (nM) |
|---|---|
| 25 | ++ |
| 26 | + |
| 27 | + |
| 28 | + |
| 29 | + |
| 30 | + |
| 31 | + |
| 32 | + |
| 35 | ++ |
| 36 | ++ |
| 37 | ++ |
| 39 | + |
| 40 | ++ |
| 41 | + |
| 42 | +++ |
| 48 | +++ |
| 49 | +++ |
| 50 | +++ |
| 52 | +++ |
| 54 | +++ |
| 56 | +++ |
| 57 | +++ |
| 58 | +++ |
| 60 | +++ |
| 61 | + |
| 63 | ++ |
| 64 | +++ |
| 65 | + |
| 66 | ++ |
| 67 | + |
| 68 | ++ |
| 69 | +++ |
| 72 | +++ |
| 74 | +++ |
| 75 | + |
| 76 | + |
| 77 | + |
| 79 | + |
| 80 | +++ |

+ refers to IC$_{50}$ of <1000 nM
++ refers to an IC$_{50}$ of <5000 nM
+++ refers to an IC$_{50}$ of ≥5000 nM Example B PI3K-γ Scintillation Proximity Assay Materials

[γ-$^{33}$P]ATP (10 mCi/mL) and Wheat Germ Agglutinin (WGA) YSi SPA Scintillation Beads was purchased from Perkin-Elmer (Waltham, Mass.). Lipid kinase substrate, D-myo-Phosphatidylinositol 4,5-bisphosphate (PtdIns(4,5) P2)D (+)-sn-1,2-di-O-octanoylglyceryl, 3-O-phospho linked (PIP2), CAS 204858-53-7, was purchased from Echelon Biosciences (Salt Lake City, Utah). PI3Kγ (p110γ) Recombinant Human Protein was purchased from Life technology (Grand Island, N.Y.). ATP, MgCl$_2$, DTT, EDTA, MOPS and CHAPS were purchased from Sigma-Aldrich (St. Louis, Mo.).

The kinase reaction was conducted in polystyrene 384-well Greiner Bio-one white plate from Thermo Fisher Scientific in a final volume of 25 μL. Inhibitors were first diluted serially in DMSO and added to the plate wells before the addition of other reaction components. The final concentration of DMSO in the assay was 2%. The PI3Kγ assay was carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 μM PIP2, 2 μM ATP, 0.5 μCi [γ-$^{33}$P] ATP, 13 nM PI3Kγ. Reactions were incubated for 120 min and terminated by the addition of 40 μL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (Perkin-Elmer). IC$_{50}$ determination was performed by fitting the curve of percent of the solvent control activity versus the log of the inhibitor concentration using the GraphPad Prism 6.0 software. Data for the Examples, obtained using the methods described in Example B, are provided in Table B.

Example C

PI3Kδ Scintillation Proximity Assay

Materials

[γ-$^{33}$P]ATP (10 mCi/mL) and Wheat Germ Agglutinin (WGA) YSi SPA Scintillation Beads was purchased from Perkin-Elmer (Waltham, Mass.). Lipid kinase substrate, D-myo-Phosphatidylinositol 4,5-bisphosphate (PtdIns(4,5) P2)D (+)-sn-1,2-di-O-octanoylglyceryl, 3-O-phospho linked (PIP2), CAS 204858-53-7, was purchased from Echelon Biosciences (Salt Lake City, Utah). PI3Kδ (p110δ/p85α) Recombinant Human Protein was purchased from Eurofins (St Charles, Mo.). ATP, MgCl$_2$, DTT, EDTA, MOPS and CHAPS were purchased from Sigma-Aldrich (St. Louis, Mo.).

The kinase reaction was conducted in polystyrene 384-well Greiner Bio-one white plate from Thermo Fisher Scientific in a final volume of 25 μL. Inhibitors were first diluted serially in DMSO and added to the plate wells before the addition of other reaction components. The final concentration of DMSO in the assay was 2%. The PI3Kδ assay was carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 μM PIP2, 2 μM ATP, 0.5 μCi [γ-$^{33}$P] ATP, 3.4 nM PI3Kδ. Reactions were incubated for 120 min and terminated by the addition of 40 μL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (Perkin-Elmer). IC$_{50}$ determination was performed by fitting the curve of percent of the solvent control activity versus the log of the inhibitor concentration using the GraphPad Prism 6.0 software.

Data for the Examples, obtained using the methods described in Example C, are provided in Table B.

TABLE B

| Example # | PI3K-gamma SPA IC$_{50}$ (nM) | PI3K-delta SPA IC$_{50}$ (nM) |
|---|---|---|
| 1 | ++ | +++ |
| 2 | +++ | +++ |
| 3 | +++ | +++ |
| 4 | + | +++ |
| 5 | + | ++ |
| 6 | ++++ | ++++ |
| 7 | ++ | ++++ |

TABLE B-continued

| Example # | PI3K-gamma SPA IC$_{50}$ (nM) | PI3K-delta SPA IC$_{50}$ (nM) |
|---|---|---|
| 8 | ++ | − |
| 10 | ++ | ++++ |
| 11 | + | +++ |
| 12 | + | ++++ |
| 13 | +++ | ++++ |
| 14 | + | +++ |
| 15 | ++ | +++ |
| 16 | + | ++ |
| 17 | + | + |
| 18 | + | ++ |
| 19 | + | + |
| 20 | + | ++ |
| 21 | + | ++ |
| 22 | + | + |
| 23 | + | + |
| 24 | + | +++ |
| 25 | + | + |
| 26 | + | ++++ |
| 27 | + | ++ |
| 28 | + | + |
| 29 | + | + |
| 30 | + | + |
| 31 | + | + |
| 32 | + | + |
| 33 | ++ | ++++ |
| 34 | + | +++ |
| 35 | + | ++++ |
| 36 | + | +++ |
| 37 | + | ++ |
| 38 | + | ++++ |
| 39 | + | + |
| 40 | + | ++ |
| 41 | + | ++ |
| 42 | ++ | +++ |
| 43 | +++ | ++++ |
| 44 | + | ++++ |
| 45 | ++++ | ++++ |
| 46 | ++++ | ++++ |
| 47 | +++ | ++++ |
| 48 | + | +++ |
| 49 | + | +++ |
| 50 | + | + |
| 51 | + | ++++ |
| 52 | + | + |
| 53 | + | ++++ |
| 54 | + | ++++ |
| 55 | +++ | ++++ |
| 56 | + | ++++ |
| 57 | + | ++ |
| 58 | + | ++ |
| 59 | + | ++++ |
| 60 | + | ++++ |
| 61 | + | + |
| 62 | ++ | +++ |
| 63 | + | ++ |
| 64 | + | + |
| 65 | + | + |
| 66 | + | + |
| 67 | + | + |
| 68 | + | + |
| 69 | + | ++++ |
| 70 | ++ | ++++ |
| 71 | ++ | +++ |
| 72 | + | +++ |
| 73 | + | +++ |
| 74 | + | + |
| 75 | + | + |
| 76 | + | + |
| 77 | + | ++ |
| 78 | +++ | +++ |
| 79 | + | + |
| 80 | + | +++ |

+ refers to IC$_{50}$ of <250 nM
++ refers to IC$_{50}$ of <1000 nM
+++ refers to an IC$_{50}$ of <5000 nM
++++ refers to an IC$_{50}$ of ≥5000 nM Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

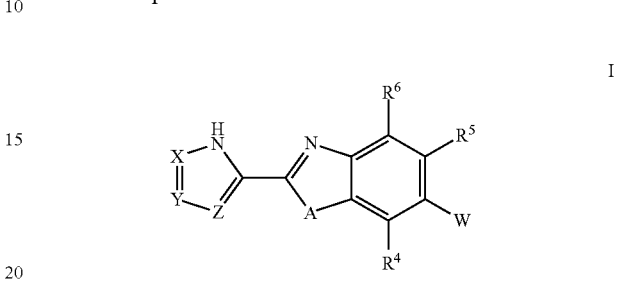

or a pharmaceutically acceptable salt thereof, wherein:
X is N or CR$^1$;
Y is N or CR$^2$;
Z is N or CR$^3$;
R$^1$, R$^2$, and R$^3$ are each independently selected from H, halo, CN, NO$_2$, C$_{1-6}$ alkyl, C$_{2-6}$ alkenyl, C$_{2-6}$ alkynyl, C$_{1-6}$ haloalkyl, Cy$^2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$; wherein said C$_{1-6}$ alkyl, C$_{2-6}$ alkenyl, and C$_{2-6}$ alkynyl are each optionally substituted with 1, 2 or 3 independently selected R$^{10}$ groups; or
alternatively, R$^1$ and R$^2$, taken together with the carbon atoms to which they are attached, form a phenyl, C$_{3-6}$ cycloalkyl, or a 5-6-membered heteroaryl ring, which is optionally substituted by 1, 2, or 3 independently selected R$^{11}$ groups; or
alternatively, R$^2$ and R$^3$, taken together with the carbon atoms to which they are attached, form a phenyl or a 5-6-membered heteroaryl ring, which is optionally substituted by 1, 2, or 3 independently selected R$^{11}$ groups;
A is O or S;
R$^4$, R$^5$, and R$^6$ are each independently selected from H, OH, NO$_2$, CN, halo, C$_{1-6}$ alkyl, C$_{2-6}$ alkenyl, C$_{2-6}$ alkynyl, C$_{3-7}$ cycloalkyl, C$_{1-6}$ haloalkyl, C$_{1-6}$ alkoxy, C$_{1-6}$ haloalkoxy, amino, C$_{1-6}$ alkylamino, di(C$_{1-6}$alkyl) amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;
W is Cy;
Cy is phenyl, naphthyl, 5-10 membered heteroaryl, or 4-10 membered heterocycloalkyl, each of which is optionally substituted by 1, 2, 3, or 4 substituents independently selected from halo, C$_{1-6}$ alkyl, C$_{2-6}$ alkenyl, C$_{2-6}$ alkynyl, C$_{1-6}$ haloalkyl, Cy$^1$, —(C$_{1-4}$ alkylene)-Cy$^1$, CN, NO$_2$, OR$^a$, SR$^a$, P(O)R$^a$R$^b$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein the C$_{1-6}$ alkyl as the substituent of Cy is further substituted by 1 or 2 independently selected R$^g$ groups;

each R$^{10}$ is independently selected from halo, CN, NO$_2$, Cy$^2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

each R$^{11}$ is independently selected from halo, CN, NO$_2$, C$_{1-6}$ alkyl, C$_{2-6}$ alkenyl, C$_{2-6}$ alkynyl, C$_{1-6}$ haloalkyl, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$; wherein said C$_{1-6}$ alkyl, C$_{2-6}$ alkenyl, and C$_{2-6}$ alkynyl are each optionally substituted with 1, 2 or 3 independently selected R$^{12}$ groups;

each R$^{12}$ is independently selected from OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^a$, R$^c$, and R$^d$ is independently selected from H, C$_{1-6}$ alkyl, C$_{2-6}$ alkenyl, C$_{2-6}$ alkynyl, C$_{1-4}$ haloalkyl, Cy$^1$, and —(C$_{1-4}$ alkylene)-Cy$^1$; wherein said C$_{1-6}$ alkyl, C$_{2-6}$ alkenyl, and C$_{2-6}$ alkynyl are each optionally substituted with 1, 2, 3, or 4 independently selected R$^g$ groups;

each R$^b$ is independently selected from C$_{1-6}$ alkyl, C$_{2-6}$ alkenyl, C$_{2-6}$ alkynyl, C$_{1-4}$ haloalkyl, Cy$^1$, and —(C$_{1-4}$ alkylene)-Cy$^1$; wherein said C$_{1-6}$ alkyl, C$_{2-6}$ alkenyl, and C$_{2-6}$ alkynyl are each optionally substituted with 1, 2, 3, or 4 independently selected R$^g$ groups; or alternatively, any R$^c$ and R$^d$ attached to the same N atom, together with the N atom to which they are attached, form a 4-6 membered heterocycloalkyl group or a 5-6 membered heteroaryl group, each optionally substituted with 1, 2, or 3 independently selected R$^g$ groups;

each R$^e$ is independently selected from H, CN, C$_{1-6}$ alkyl, C$_{1-6}$ haloalkyl, C$_{1-6}$ alkylthio, C$_{1-6}$ alkylsulfonyl, C$_{1-6}$ alkylcarbonyl, C$_{1-6}$ alkylaminosulfonyl, carbamyl, C$_{1-6}$ alkylcarbamyl, di(C$_{1-6}$ alkyl)carbamyl, aminosulfonyl, C$_{1-6}$ alkylaminosulfonyl, and di(C$_{1-6}$ alkyl)aminosulfonyl;

each R$^{a1}$, R$^{c1}$, and R$^{d1}$ are independently selected from H, C$_{1-6}$ alkyl, C$_{2-6}$ alkenyl, C$_{2-6}$ alkynyl, C$_{1-4}$ haloalkyl, and Cy$^3$; wherein said C$_{1-6}$ alkyl, C$_{2-6}$ alkenyl, and C$_{2-6}$ alkynyl are each optionally substituted with 1, 2 or 3 independently selected R$^{12}$ groups;

each R$^{b1}$ is independently selected from C$_{1-6}$ alkyl, C$_{2-6}$ alkenyl, C$_{2-6}$ alkynyl, C$_{1-4}$ haloalkyl, and Cy$^3$; wherein said C$_{1-6}$ alkyl, C$_{2-6}$ alkenyl, and C$_{2-6}$ alkynyl are each optionally substituted with 1, 2 or 3 independently selected R$^{12}$ groups; or alternatively, any R$^{c1}$ and R$^{d1}$ attached to the same N atom, together with the N atom to which they are attached, form a 4-, 5-, 6- or 7-membered heterocycloalkyl group optionally substituted with 1, 2 or 3 independently selected R$^{12}$ groups;

each R$^{a2}$, R$^{c2}$, and R$^{d2}$ is independently selected from H, C$_{1-6}$ alkyl, C$_{2-6}$ alkenyl, C$_{2-6}$ alkynyl, and C$_{1-4}$ haloalkyl; wherein said C$_{1-6}$ alkyl, C$_{2-6}$ alkenyl, and C$_{2-6}$ alkynyl are each optionally substituted with 1, 2 or 3 independently selected R$^{12}$ groups;

each R$^{b2}$ is independently selected from C$_{1-6}$ alkyl, C$_{2-6}$ alkenyl, C$_{2-6}$ alkynyl, and C$_{1-4}$ haloalkyl; wherein said C$_{1-6}$ alkyl, C$_{2-6}$ alkenyl, and C$_{2-6}$ alkynyl are each optionally substituted with 1, 2 or 3 independently selected R$^{12}$ groups; or alternatively, any R$^{c2}$ and R$^{d2}$ attached to the same N atom, together with the N atom to which they are attached, form a 4-, 5-, 6- or 7-membered heterocycloalkyl group optionally substituted with 1, 2 or 3 independently selected R$^{12}$ groups;

each Cy$^1$ is independently selected from phenyl, 5-6 membered heteroaryl, C$_{3-7}$ cycloalkyl, and 4-6 membered heterocycloalkyl, each optionally substituted by 1, 2, 3, or 4 independently selected R$^g$ groups;

each Cy$^2$ is independently selected from phenyl, C$_{3-7}$ cycloalkyl, 5-6 membered heteroaryl, and 4-6 membered heterocycloalkyl; wherein said phenyl, 5-6 membered heteroaryl, C$_{3-7}$ cycloalkyl, and 4-6 membered heterocycloalkyl are each optionally substituted with 1, 2 or 3 independently selected R$^{11}$ groups;

each Cy$^3$ is independently selected from phenyl, C$_{3-7}$ cycloalkyl, 5-6 membered heteroaryl, and 4-6 membered heterocycloalkyl; wherein said phenyl, 5-6 membered heteroaryl, C$_{3-7}$ cycloalkyl, and 4-6 membered heterocycloalkyl are each optionally substituted with 1, 2 or 3 independently selected C$_{1-4}$ alkylene-R$^{12}$ or R$^{12}$ groups; and each R$^g$ is independently selected from OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino.

2. The compound of claim 1, or a pharmaceutically acceptable salt thereof, wherein:

X is N or CR$^1$;

Y is N or CR$^2$;

Z is N or CR$^3$;

R$^1$, R$^2$, and R$^3$ are each independently selected from H, halo, CN, NO$_2$, C$_{1-6}$ alkyl, C$_{2-6}$ alkenyl, C$_{2-6}$ alkynyl, C$_{1-6}$ haloalkyl, Cy$^2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^b$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$; wherein said C$_{1-6}$ alkyl, C$_{2-6}$ alkenyl, and C$_{2-6}$ alkynyl are each optionally substituted with 1, 2 or 3 independently selected R$^{10}$ groups; or alternatively, $R^1$ and $R^2$, taken together with the carbon atoms to which they are attached, form a phenyl or a 5-6-membered heteroaryl ring, which is optionally substituted by 1, 2, or 3 independently selected $R^{11}$ groups; or alternatively, $R^2$ and $R^3$, taken together with the carbon atoms to which they are attached, form a phenyl or a 5-6-membered heteroaryl ring, which is optionally substituted by 1, 2, or 3 independently selected $R^{11}$ groups;

A is O or S;

$R^4$, $R^5$, and $R^6$ are each independently selected from H, OH, $NO_2$, CN, halo, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

W is Cy;

Cy is phenyl, naphthyl, 5-10 membered heteroaryl, or 4-10 membered heterocycloalkyl, each of which is optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $Cy^1$, —($C_{1-4}$ alkylene)-$Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^{10}$ is independently selected from halo, CN, $NO_2$, $Cy^2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

each $R^{11}$ is independently selected from halo, CN, $NO_2$, $C_{1-6}$ alkyl, $C_{2-6}$ alkenyl, $C_{2-6}$ alkynyl, $C_{1-6}$ haloalkyl, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2 or 3 independently selected $R^{12}$ groups;

each $R^{12}$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^a$, $R^c$, and $R^d$ is independently selected from H, $C_{1-6}$ alkyl, $C_{2-6}$ alkenyl, $C_{2-6}$ alkynyl, $C_{1-4}$ haloalkyl, $Cy^1$, and —($C_{1-4}$ alkylene)-$Cy^1$; wherein said $C_{1-6}$ alkyl, $C_{2-6}$ alkenyl, and $C_{2-6}$ alkynyl are each optionally substituted with 1, 2, 3, or 4 independently selected $R^g$ groups;

each $R^b$ is independently selected from $C_{1-6}$ alkyl, $C_{2-6}$ alkenyl, $C_{2-6}$ alkynyl, $C_{1-4}$ haloalkyl, $Cy^1$, and —($C_{1-4}$ alkylene)-$Cy^1$; wherein said $C_{1-6}$ alkyl, $C_{2-6}$ alkenyl, and $C_{2-6}$ alkynyl are each optionally substituted with 1, 2, 3, or 4 independently selected $R^g$ groups; or alternatively, any $R^c$ and $R^d$ attached to the same N atom, together with the N atom to which they are attached, form a 4-6 membered heterocycloalkyl group or a 5-6 membered heteroaryl group, each optionally substituted with 1, 2, or 3 independently selected $R^g$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^{a1}$, $R^{c1}$, and $R^{d1}$ are independently selected from H, $C_{1-6}$ alkyl, $C_{2-6}$ alkenyl, $C_{2-6}$ alkynyl, $C_{1-4}$ haloalkyl, and $Cy^3$; wherein said $C_{1-6}$ alkyl, $C_{2-6}$ alkenyl, and $C_{2-6}$ alkynyl are each optionally substituted with 1, 2 or 3 independently selected $R^{12}$ groups;

each $R^{b1}$ is independently selected from $C_{1-6}$ alkyl, $C_{2-6}$ alkenyl, $C_{2-6}$ alkynyl, $C_{1-4}$ haloalkyl, and $Cy^3$; wherein said $C_{1-6}$ alkyl, $C_{2-6}$ alkenyl, and $C_{2-6}$ alkynyl are each optionally substituted with 1, 2 or 3 independently selected $R^{12}$ groups; or alternatively, any $R^{c1}$ and $R^{d1}$ attached to the same N atom, together with the N atom to which they are attached, form a 4-, 5-, 6- or 7-membered heterocycloalkyl group optionally substituted with 1, 2 or 3 independently selected $R^{12}$ groups;

each $R^{a2}$, $R^{c2}$, and $R^{d2}$ is independently selected from H, $C_{1-6}$ alkyl, $C_{2-6}$ alkenyl, $C_{2-6}$ alkynyl, and $C_{1-4}$ haloalkyl; wherein said $C_{1-6}$ alkyl, $C_{2-6}$ alkenyl, and $C_{2-6}$ alkynyl are each optionally substituted with 1, 2 or 3 independently selected $R^{12}$ groups;

each $R^{b2}$ is independently selected from $C_{1-6}$ alkyl, $C_{2-6}$ alkenyl, $C_{2-6}$ alkynyl, and $C_{1-4}$ haloalkyl; wherein said $C_{1-6}$ alkyl, $C_{2-6}$ alkenyl, and $C_{2-6}$ alkynyl are each optionally substituted with 1, 2 or 3 independently selected $R^{12}$ groups; or alternatively, any $R^{c2}$ and $R^{d2}$ attached to the same N atom, together with the N atom to which they are attached, form a 4-, 5-, 6- or 7-membered heterocycloalkyl group optionally substituted with 1, 2 or 3 independently selected $R^{12}$ groups;

each $Cy^1$ is independently selected from phenyl, 5-6 membered heteroaryl, $C_{3-7}$ cycloalkyl, and 4-6 membered heterocycloalkyl, each optionally substituted by 1, 2, 3, or 4 independently selected $R^g$ groups;

each $Cy^2$ is independently selected from phenyl, $C_{3-7}$ cycloalkyl, 5-6 membered heteroaryl, and 4-6 membered heterocycloalkyl; wherein said phenyl, 5-6 membered heteroaryl, $C_{3-7}$ cycloalkyl, and 4-6 membered heterocycloalkyl are each optionally substituted with 1, 2 or 3 independently selected $R^{11}$ groups;

each $Cy^3$ is independently selected from phenyl, $C_{3-7}$ cycloalkyl, 5-6 membered heteroaryl, and 4-6 membered heterocycloalkyl; wherein said phenyl, 5-6 membered heteroaryl, $C_{3-7}$ cycloalkyl, and 4-6 membered heterocycloalkyl are each optionally substituted with 1, 2 or 3 independently selected $C_{1-4}$ alkylene-$R^{12}$ or $R^{12}$ groups; and each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

3. The compound of claim 1, or a pharmaceutically acceptable salt thereof, wherein $R^1$ is H, methyl, ethyl, cyclopropyl, phenyl, or a tetrahydrofuran ring.

4. The compound of claim 1, or a pharmaceutically acceptable salt thereof, wherein $R^2$ is H, methyl, propyl, or phenyl.

5. The compound of claim 1, or a pharmaceutically acceptable salt thereof, wherein $R^1$ and $R^2$, together with the carbon atoms to which they are attached, form a phenyl ring or cyclohexene group, which is optionally substituted by 1, 2, or 3 independently selected $R^{11}$ groups.

6. The compound of claim 1, or a pharmaceutically acceptable salt thereof, wherein $R^1$ and $R^2$, together with the carbon atoms to which they are attached, form a phenyl ring, which is optionally substituted by 1, 2, or 3 $R^{11}$ groups independently selected from halo, $C_{1-6}$ alkyl, and $C_{1-6}$ haloalkyl.

7. The compound of claim 1, or a pharmaceutically acceptable salt thereof, wherein $R^3$ is H.

8. The compound of claim 1, or a pharmaceutically acceptable salt thereof, wherein $R^4$, $R^5$, and $R^6$ are each H.

9. The compound of claim 1, wherein Cy is a pyridine ring, which is optionally substituted by 1, 2, 3, or 4 substituents independently selected from halo, $C_{1-6}$ alkyl, $C_{1-6}$ haloalkyl, CN, $OR^a$, $NR^cR^d$, $NR^cC(O)R^b$, $NR^cS(O)_2R^b$, $NR^cS(O)_2NR^cR^d$, $S(O)_2R^b$, and $S(O)_2NR^cR^d$.

10. The compound of claim 1, or a pharmaceutically acceptable salt thereof, wherein

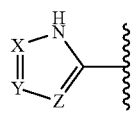

is

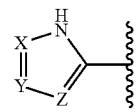

11. The compound of claim 1, or a pharmaceutically acceptable salt thereof, wherein

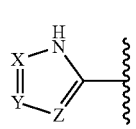

is

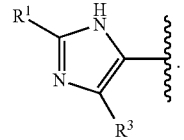

12. The compound of claim 1, or a pharmaceutically acceptable salt thereof, wherein

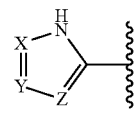

is

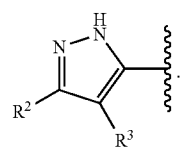

13. The compound of claim 1, or a pharmaceutically acceptable salt thereof, wherein

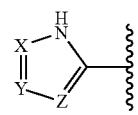

is

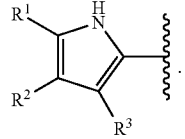

14. The compound of claim 1, or a pharmaceutically acceptable salt thereof, where A is O.

15. The compound of claim 1, or a pharmaceutically acceptable salt thereof, where A is S.

16. The compound of claim 1, or a pharmaceutically acceptable salt thereof, wherein:

is:

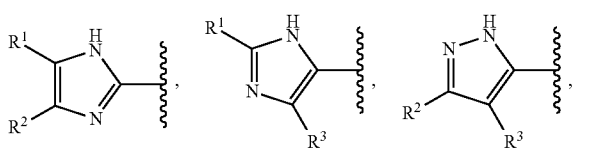

or

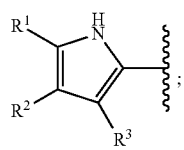

A is O or S;
R¹ and R² are each independently selected from H, OR$^{a1}$, NO₂, CN, halo, C$_{1-6}$ alkyl, C$_{1-6}$ haloalkyl, and Cy²;
R³ is H, methyl, or ethyl;
or R¹ and R², together with the carbon atoms to which they are attached, form a phenyl ring, which is optionally substituted by 1, 2, or 3 independently selected R¹¹ groups;
R⁴, R⁵, and R⁶ are each H;
W is Cy;
Cy is 6-membered heteroaryl, which is optionally substituted by 1, 2, or 3 substituents independently selected from halo, C$_{1-6}$ alkyl, C$_{2-6}$ alkenyl, C$_{2-6}$ alkynyl, C$_{1-6}$ haloalkyl, Cy¹, —(C$_{1-4}$ alkylene)-Cy¹, CN, NO₂, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)₂R$^b$, NR$^c$S(O)₂NR$^c$R$^d$, S(O)R$^b$, S(O)NR$^c$R$^d$, S(O)₂R$^b$, and S(O)₂NR$^c$R$^d$;
each Cy² is independently selected from phenyl, C$_{3-7}$ cycloalkyl, 5-6 membered heteroaryl, and 4-6 membered heterocycloalkyl;
each R¹¹ is independently selected from halo, C$_{1-6}$ alkyl, and C$_{1-6}$ haloalkyl;
each R$^{a1}$ is independently selected from H, C$_{1-6}$ alkyl, and C$_{14}$ haloalkyl;
each R$^a$, R$^c$, and R$^d$ is independently selected from H, C$_{1-6}$ alkyl, C$_{2-6}$ alkenyl, C$_{2-6}$ alkynyl, C$_{1-4}$ haloalkyl, Cy¹, and —(C$_{1-4}$ alkylene)-Cy¹; wherein said C$_{1-6}$ alkyl, C$_{2-6}$ alkenyl, and C$_{2-6}$ alkynyl are each optionally substituted with 1, 2, 3, or 4 independently selected R$^g$ groups;
each R$^b$ is independently selected from C$_{1-6}$ alkyl, C$_{2-6}$ alkenyl, C$_{2-6}$ alkynyl, C$_{1-4}$ haloalkyl, Cy¹, and —(C$_{1-4}$ alkylene)-Cy¹; wherein said C$_{1-6}$ alkyl, C$_{2-6}$ alkenyl, and C$_{2-6}$ alkynyl are each optionally substituted with 1, 2, 3, or 4 independently selected R$^g$ groups;
or any R$^c$ and R$^d$ together with the N atom to which they are attached form a 4-6 membered heterocycloalkyl group or a 5-6 membered heteroaryl group, each optionally substituted with 1, 2, or 3 independently selected R$^g$ groups;
each R$^e$ is independently selected from H and C$_{1-6}$ alkyl;
each Cy¹ is independently selected from phenyl, 5-6 membered heteroaryl, C$_{3-7}$ cycloalkyl, and 4-6 membered heterocycloalkyl, each optionally substituted by 1, 2, 3, or 4 independently selected R$^g$ groups; and each R$^g$ is independently selected from OH, NO₂, CN, halo, C$_{1-6}$ alkyl, C$_{2-6}$ alkenyl, C$_{2-6}$ alkynyl, C$_{1-6}$ haloalkyl, cyano-C$_{1-3}$ alkyl, HO—C$_{1-3}$ alkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino.

17. The compound of claim 1, or a pharmaceutically acceptable salt thereof, wherein:

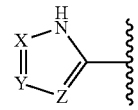

is:

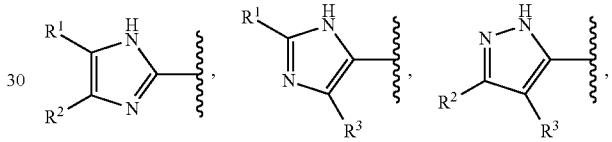

or

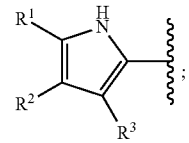

A is O or S;
R¹ is H, methyl, ethyl, cyclopropyl, phenyl, or a tetrahydrofuran ring;
R² is H, methyl, propyl, or phenyl; or
R¹ and R², together with the carbon atoms to which they are attached, form a phenyl ring or cyclohexene ring, which is optionally substituted by 1 or 2 independently selected R¹¹ groups;
R³ is H;
R⁴, R⁵, and R⁶ are each H;
W is Cy;
Cy is a phenyl ring, a piperazine ring, a pyridine ring, a pyrimidine ring, an imidazole ring, an indazole ring, or a 1H-pyrazolo[4,3-b]pyridine ring, each of which is optionally substituted by 1 or 2 substituents independently selected from halo, C$_{1-6}$ alkyl, C$_{1-6}$ haloalkyl, Cy¹, —(C$_{1-2}$ alkylene)-Cy¹, CN, OR$^a$, P(O)R$^a$R$^b$, NR$^c$R$^d$, NR$^c$C(O)R$^b$, NR$^c$C(O)NR$^c$R$^d$, NR$^c$S(O)₂R$^b$, NR$^c$S(O)₂NR$^c$R$^d$, S(O)₂R$^b$, and S(O)₂NR$^c$R$^d$;
each R¹¹ is independently selected from halo, C$_{1-6}$ alkyl, and C$_{1-6}$ haloalkyl;
each R$^a$ is independently selected from H and C$_{1-6}$ alkyl; wherein said C$_{1-6}$ alkyl is optionally substituted with 1, 2, 3, or 4 independently selected R$^g$ groups;

each $R^c$ and $R^d$ is independently selected from H, $C_{1-6}$ alkyl, and $Cy^1$; wherein said $C_{1-6}$ alkyl is optionally substituted with 1, 2, 3, or 4 independently selected $R^g$ groups;

each $R^b$ is independently selected from $C_{1-6}$ alkyl and $Cy^1$; wherein said $C_{1-6}$ alkyl is optionally substituted with 1, 2, 3, or 4 independently selected $R^g$ groups;

each $Cy^1$ is independently selected from phenyl and 6-membered heterocycloalkyl, each optionally substituted by 1 or 2 independently selected $R^g$ groups; and each $R^g$ is, independently, OH, $C_{1-6}$ alkyl, $C_{1-4}$ haloalkyl, halo, or carboxy.

18. The compound of claim 1, or a pharmaceutically acceptable salt thereof, having Formula II:

II or a pharmaceutically acceptable salt thereof.

19. The compound of claim 1, or a pharmaceutically acceptable salt thereof, having Formula III:

III or a pharmaceutically acceptable salt thereof.

20. The compound of claim 1, or a pharmaceutically acceptable salt thereof, having Formula V:

V or a pharmaceutically acceptable salt thereof.

21. The compound of claim 1, or a pharmaceutically acceptable salt thereof, having Formula VI:

VI or a pharmaceutically acceptable salt thereof.

22. The compound of claim 1, or a pharmaceutically acceptable salt thereof, having Formula VII:

VII or a pharmaceutically acceptable salt thereof.

23. The compound of claim 1, or a pharmaceutically salt thereof, having Formula IIa, IIb, IIIa, or VIIa:

IIa

IIb

IIIa

VIIa or a pharmaceutically acceptable salt thereof.

24. The compound of claim 1, selected from:
2-(1H-imidazol-2-yl)-6-(5-methoxypyridin-3-yl)benzo[d]oxazole;
2-(1H-imidazol-5-yl)-6-(5-methoxypyridin-3-yl)benzo[d]oxazole;
6-(5-methoxypyridin-3-yl)-2-(1H-pyrrol-2-yl)benzo[d]oxazole;
2-(1H-benzo[d]imidazol-2-yl)-6-(5-methoxypyridin-3-yl)benzo[d]oxazole;
2-(1H-indol-2-yl)-6-(5-methoxypyridin-3-yl)benzo[d]oxazole;
2-(1H-benzo[d]imidazol-2-yl)-6-(5-methoxypyridin-3-yl)benzo[d]thiazole;
2-(6-bromo-1H-benzo[d]imidazol-2-yl)-6-(5-methoxypyridin-3-yl)benzo[d]oxazole;
2-(5-fluoro-1H-benzo[d]imidazol-2-yl)-6-(5-methoxypyridin-3-yl)benzo[d]oxazole;
6-(5-methoxypyridin-3-yl)-2-(5-methyl-1H-benzo[d]imidazol-2-yl)benzo[d]oxazole;
6-(5-methoxypyridin-3-yl)-2-(4-methyl-1H-benzo[d]imidazol-2-yl)benzo[d]oxazole;
5-(2-(1H-benzo[d]imidazol-2-yl)benzo[d]oxazol-6-yl)pyridin-3-ol;
2-(1H-benzo[d]imidazol-2-yl)-6-(5-isopropoxypyridin-3-yl)benzo[d]oxazole;
2-(1H-benzo[d]imidazol-2-yl)-6-(5-(difluoromethoxy)pyridin-3-yl)benzo[d]oxazole;
N-(5-(2-(1H-benzo[d]imidazol-2-yl)benzo[d]oxazol-6-yl)pyridin-3-yl)-4-fluorobenzenesulfonamide;
N-(5-(2-(1H-benzo[d]imidazol-2-yl)benzo[d]oxazol-6-yl)pyridin-3-yl)ethanesulfonamide;
N-(5-(2-(1H-benzo[d]imidazol-2-yl)benzo[d]oxazol-6-yl)pyridin-3-yl)-3-fluorobenzenesulfonamide;
N-(5-(2-(1H-benzo[d]imidazol-2-yl)benzo[d]oxazol-6-yl)pyridin-3-yl)piperidine-1-sulfonamide;
N'-{5-[2-(1H-benzimidazol-2-yl)-1,3-benzoxazol-6-yl]-pyridin-3-yl}-N,N-dimethylsulfamide;
N'-{5-[2-(1H-benzimidazol-2-yl)-1,3-benzoxazol-6-yl]-2-methylpyridin-3-yl}-N,N-dimethylsulfamide;
N'-{5-[2-(1H-benzimidazol-2-yl)-1,3-benzoxazol-6-yl]-2-fluoropyridin-3-yl}-N,N-dimethylsulfamide;
N-(5-(2-(1H-benzo[d]imidazol-2-yl)benzo[d]oxazol-6-yl)pyridin-3-yl)propane-2-sulfonamide;
N-(5-(2-(1H-benzo[d]imidazol-2-yl)benzo[d]oxazol-6-yl)-2-methylpyridin-3-yl)ethanesulfonamide;
N-(5-(2-(1H-benzo[d]imidazol-2-yl)benzo[d]oxazol-6-yl)-2-chloropyridin-3-yl)ethanesulfonamide;
N-(5-(2-(1H-benzo[d]imidazol-2-yl)benzo[d]oxazol-6-yl)-2-fluoropyridin-3-yl)ethanesulfonamide;
N-(5-(2-(1H-benzo[d]imidazol-2-yl)benzo[d]oxazol-6-yl)-2-methylpyridin-3-yl)-4-fluorobenzenesulfonamide;
N-(5-(2-(1H-benzo[d]imidazol-2-yl)benzo[d]oxazol-6-yl)-2-chloropyridin-3-yl)-4-fluorobenzenesulfonamide;
N-(5-(2-(1H-benzo[d]imidazol-2-yl)benzo[d]oxazol-6-yl)-2-fluoropyridin-3-yl)-4-fluorobenzenesulfonamide;
N-(5-(2-(1H-benzo[d]imidazol-2-yl)benzo[d]oxazol-6-yl)pyridin-3-yl)-4-methylpiperazine-1-sulfonamide;
N-(5-(2-(1H-benzo[d]imidazol-2-yl)benzo[d]oxazol-6-yl)-2-fluoropyridin-3-yl)-4-methylpiperazine-1-sulfonamide;
N-(5-(2-(1H-benzo[d]imidazol-2-yl)benzo[d]oxazol-6-yl)pyridin-3-yl)acetamide;
5-(2-(1H-benzo[d]imidazol-2-yl)benzo[d]oxazol-6-yl)-N,N-dimethylpyridin-3-amine;
5-(2-(1H-benzo[d]imidazol-2-yl)benzo[d]oxazol-6-yl)nicotinonitrile;
2-(1H-benzo[d]imidazol-2-yl)-6-(5-(methylsulfonyl)pyridin-3-yl)benzo[d]oxazole;
5-[2-(1H-benzimidazol-2-yl)-1,3-benzoxazol-6-yl]-N,N-dimethylpyridine-3-sulfonamide;
2-(1H-benzo[d]imidazol-2-yl)-6-(5-(morpholinosulfonyl)pyridin-3-yl)benzo[d]oxazole;
N-(5-(2-(1H-imidazol-2-yl)benzo[d]oxazol-6-yl)pyridin-3-yl)-4-fluorobenzenesulfonamide;
N-(5-(2-(1H-imidazol-2-yl)benzo[d]oxazol-6-yl)pyridin-3-yl)ethanesulfonamide;
N'-{5-[2-(1H-imidazol-2-yl)-1,3-benzoxazol-6-yl]pyridin-3-yl}-N,N-dimethylsulfamide;
2-(2-cyclopropyl-1H-imidazol-5-yl)-6-(5-methoxypyridin-3-yl)benzo[d]oxazole;
6-(5-methoxypyridin-3-yl)-2-(2-(tetrahydrofuran-3-yl)-1H-imidazol-5-yl)benzo[d]oxazole;
6-(5-methoxypyridin-3-yl)-2-(2-phenyl-1H-imidazol-5-yl)benzo[d]oxazole;
2-(2-ethyl-1H-imidazol-5-yl)-6-(5-methoxypyridin-3-yl)benzo[d]oxazole;
6-(5-methoxypyridin-3-yl)-2-(3-methyl-1H-pyrazol-5-yl)benzo[d]oxazole;
6-(5-methoxypyridin-3-yl)-2-(3-phenyl-1H-pyrazol-5-yl)benzo[d]oxazole;
or a pharmaceutically acceptable salt of any of the aforementioned.

25. The compound of claim 1, selected from:
2-(1H-Benzimidazol-2-yl)-6-(1-benzyl-1H-pyrazol-4-yl)-1,3-benzoxazole;
2-(1H-Benzimidazol-2-yl)-6-(1H-indazol-5-yl)-1,3-benzoxazole;
2-(1H-Benzimidazol-2-yl)-6-(3-methyl-1H-indazol-5-yl)-1,3-benzoxazole;
2-(1H-Benzimidazol-2-yl)-6-(3,4-difluorophenyl)-1,3-benzoxazole;
6-[1-(Ethylsulfonyl)-1H-indazol-6-yl]-2-(1H-benzimidazol-2-yl)-1,3-benzoxazole;
2-(1H-Benzimidazol-2-yl)-6-(2-ethyl-2H-indazol-6-yl)-1, 3-benzoxazole;
2-(1H-Benzimidazol-2-yl)-6-(1-ethyl-1H-indazol-6-yl)-1, 3-benzoxazole;
2-(1H-Benzimidazol-2-yl)-6-(4-benzylpiperazin-1-yl)-1, 3-benzoxazole;
5-[2-(1H-Benzimidazol-2-yl)-1,3-benzoxazol-6-yl]-3-(trifluoromethyl)pyridin-2-amine;
6-[2-(1H-Benzimidazol-2-yl)-1,3-benzoxazol-6-yl]-1-ethyl-1H-pyrazolo[4,3-b]pyridine;
1-({5-[2-(1H-Benzimidazol-2-yl)-1,3-benzoxazol-6-yl]pyridin-3-yl}sulfonyl)pyrrolidin-3-ol;
5-[2-(1H-Benzimidazol-2-yl)-1,3-benzoxazol-6-yl]-N-ethylpyridine-3-sulfonamide;
N-{5-[2-(1H-Benzimidazol-2-yl)-1,3-benzoxazol-6-yl]-2-fluorophenyl}ethanesulfonamide;
1-(5-(2-(1H-Imidazol-2-yl)benzo[d]oxazol-6-yl)pyridin-3-yl)-2, 2,2-trifluoroethanol;
2-(4, 5-Dimethyl-1H-imidazol-2-yl)-6-(5-(methylsulfonyl)pyridin-3-yl)benzo[d]oxazole;
N-(5-(2-(4,5-Dimethyl-1H-imidazol-2-yl)benzo[d]oxazol-6-yl)pyridin-3-yl)ethanesulfonamide;
N-(5-(2-(5-Methyl-4-propyl-1H-imidazol-2-yl)benzo[d]oxazol-6-yl)pyridin-3-yl)ethanesulfonamide;
N-(5-(2-(4,5-Dimethyl-1H-imidazol-2-yl)benzo[d]oxazol-6-yl)-2-methoxypyridin-3-yl)ethanesulfonamide;

N-(2-Methoxy-5-(2-(4,5,6,7-tetrahydro-1H-benzo[d]imidazol-2-yl)benzo[d]oxazol-6-yl)pyridin-3-yl)ethanesulfonamide;

1-(5-(2-(4,5-Dimethyl-1H-imidazol-2-yl)benzo[d]oxazol-6-yl)pyridin-3-yl)-2,2,2-trifluoroethanol;

2,2,2-Trifluoro-1-(5-(2-(4,5,6,7-tetrahydro-1H-benzo[d]imidazol-2-yl)benzo[d]oxazol-6-yl)pyridin-3-yl)ethanol;

2-(1H-Benzo[d]imidazol-2-yl)-6-(6-fluoro-5-methoxypyridin-3-yl)benzo[d]oxazole;

2-(1H-Benzo[d]imidazol-2-yl)-6-(2-fluoropyrimidin-5-yl)benzo[d]oxazole;

2-(5-(2-(1H-Benzo[d]imidazol-2-yl)benzo[d]oxazol-6-yl)pyridin-3-yl)acetic acid;

2-(1H-Benzo[d]imidazol-2-yl)-6-(5-(dimethylphosphoryl)pyridin-3-yl)benzo[d]oxazole;

N-(5-(2-(1H-Benzo[d]imidazol-2-yl)benzo[d]oxazol-6-yl)pyridin-3-yl)-N-methylethanesulfonamide;

1-(5-(2-(1H-Benzo[d]imidazol-2-yl)benzo[d]oxazol-6-yl)pyridin-3-yl)-2,2,2-trifluoroethanol;

N-(5-(2-(1H-Benzo[d]imidazol-2-yl)benzo[d]oxazol-6-yl)-2-fluoropyridin-3-yl)-2,2,2-trifluoroethanesulfonamide;

N-(5-(2-(1H-Benzo[d]imidazol-2-yl)benzo[d]oxazol-6-yl)-2-methylpyridin-3-yl)-2,2,2-trifluoroethanesulfonamide;

N-(5-(2-(1H-Benzo[d]imidazol-2-yl)benzo[d]oxazol-6-yl)pyridin-3-yl)-2,2,2-trifluoroethanesulfonamide;

N-(2-(2-(1H-Benzo[d]imidazol-2-yl)benzo[d]oxazol-6-yl)-5-fluoropyridin-4-yl)ethanesulfonamide;

N-(5-(2-(1H-Benzo[d]imidazol-2-yl)benzo[d]oxazol-6-yl)-2-methoxypyridin-3-yl)ethanesulfonamide; and N-(5-(2-(1H-Benzo[d]imidazol-2-yl)benzo[d]oxazol-6-yl)-3-fluoro-2-methoxyphenyl)ethanesulfonamide;

or a pharmaceutically acceptable salt of any of the aforementioned.

26. A pharmaceutical composition comprising a compound of claim 1, or a pharmaceutically acceptable salt thereof, and a pharmaceutically acceptable carrier.

\* \* \* \* \*

UNITED STATES PATENT AND TRADEMARK OFFICE
CERTIFICATE OF CORRECTION

PATENT NO. : 9,586,949 B2
APPLICATION NO. : 15/019144
DATED : March 7, 2017
INVENTOR(S) : Ge Zou, Andrew P. Combs and Andrew W. Buesking It is certified that error appears in the above-identified patent and that said Letters Patent is hereby corrected as shown below:

On the Title Page

Item (56), Column 2, Line 4, delete "Highy" and insert -- Highly --.

In the Claims

Column 111, Line 46, Claim 16, delete "$C_{14}$" and insert -- $C_{1-4}$ --.

Signed and Sealed this
Twenty-sixth Day of May, 2020

Andrei Iancu
*Director of the United States Patent and Trademark Office*